United States Patent
Leung et al.

(10) Patent No.: US 12,227,570 B2
(45) Date of Patent: *Feb. 18, 2025

(54) ANTI-CEACAM6 ANTIBODIES AND METHODS OF USE

(71) Applicants: Singapore Health Services PTE LTD, Singapore (SG); AGENCY FOR SCIENCE, TECHNOLOGY AND RESEARCH, Singapore (SG)

(72) Inventors: Hau Wan Leung, Singapore (SG); Andre Boon Hwa Choo, Singapore (SG); Mei Yee Vanessa Ding, Singapore (SG); Shao Weng Daniel Tan, Singapore (SG); Narayanan Gopalakrishna Iyer, Singapore (SG)

(73) Assignees: Singapore Health Services PTE LTD, Singapore (SG); Agency for Science, Technology and Research, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 18/383,043

(22) Filed: Oct. 23, 2023

(65) Prior Publication Data

US 2024/0254221 A1 Aug. 1, 2024

Related U.S. Application Data

(63) Continuation of application No. 17/560,232, filed on Dec. 22, 2021, now Pat. No. 11,820,821, which is a continuation of application No. 16/341,052, filed as application No. PCT/SG2017/050509 on Oct. 10, 2017, now Pat. No. 11,236,160.

(30) Foreign Application Priority Data

Oct. 10, 2016 (SG) .......................... 10201608481W

(51) Int. Cl.
| | |
|---|---|
| *C07K 16/28* | (2006.01) |
| *A61K 39/00* | (2006.01) |
| *A61K 47/64* | (2017.01) |
| *A61K 47/68* | (2017.01) |
| *A61K 51/10* | (2006.01) |
| *A61P 35/00* | (2006.01) |
| *C07K 16/30* | (2006.01) |
| *C07K 16/44* | (2006.01) |
| *G01N 33/574* | (2006.01) |

(52) U.S. Cl.
CPC ...... *C07K 16/2803* (2013.01); *A61K 47/6415* (2017.08); *A61K 47/68031* (2023.08); *A61K 47/6857* (2017.08); *A61K 51/1048* (2013.01); *A61P 35/00* (2018.01); *C07K 16/30* (2013.01); *C07K 16/44* (2013.01); *G01N 33/57473* (2013.01); *A61K 2039/505* (2013.01); *A61K 2039/55* (2013.01); *C07K 2317/732* (2013.01)

(58) Field of Classification Search
CPC .... C07K 16/2803; C07K 16/30; C07K 16/44; C07K 2317/732; A61K 47/6415; A61K 47/6857; A61K 51/1048; A61K 2039/505; A61K 2039/55; A61P 35/00; G01N 33/57473

See application file for complete search history.

(56) References Cited

U.S. PATENT DOCUMENTS 11,236,160 B2 * 2/2022 Leung ................ A61K 47/6803

FOREIGN PATENT DOCUMENTS

| EP | 3276005 A1 * | 1/2018 | ......... C07K 14/4728 |
|---|---|---|---|
| WO | 2000029004 A1 | 5/2000 | |
| WO | 2011163401 A2 | 12/2011 | |
| WO | 2012040824 A1 | 4/2012 | |
| WO | 2016150899 A2 | 9/2016 | |
| WO | WO-2017112829 A1 * | 6/2017 | ........... A61K 39/395 |

OTHER PUBLICATIONS

Product Guide for Cyanine Dyes (Cy Dyes), Tocris Bioscience, 2023, 3 pages.
Schozel et al., American Journal of Pathology, 156:595-605, 2000, 11 pages.

(Continued)

*Primary Examiner* — Julie Wu
*Assistant Examiner* — Sydney Van Druff
(74) *Attorney, Agent, or Firm* — Womble Bond Dickinson (US) LLP

(57) ABSTRACT

The present invention relates to an antigen-binding protein, or an antigen-binding fragment thereof which binding to CEACAM6, comprising (i) a heavy chain variable domain comprising a VHCDR1 having the amino acid sequence GNTFTSYVMH; a VHCDR2 having the amino acid sequence YINPYNDGTKYNEKFKG; and a VHCDR3 having the amino acid sequence STARATPYFYAMDY and (ii) a light chain variable domain comprising a VLCDR1 having the amino acid sequence KSSQSLLWSVNQNSYLS, a VLCDR2 having the amino acid sequence GASIRES, and a VLCDR3 having the amino acid sequence QHNHGSFLPYT. The present invention also relates to compositions comprising the antigen-binding protein, or antigen-binding fragment thereof, methods of use of the antigen-binding protein, or antigen-binding fragment thereof for cancer treatment, prevention or detection and a kit comprising the antigen-binding protein, or antigen-binding fragment thereof.

12 Claims, 54 Drawing Sheets

Specification includes a Sequence Listing.

(56) References Cited

OTHER PUBLICATIONS

Creative Biolabs, "Tandem Diabody (TandAb)", downloaded Jun. 22, 2021, https://www.creativebiolabs.net/tandem-diabody-tandab.htm, 7 pages.

Ausubel et al., "Current Protocols in Molecular Biology," Dec. 4, 2003, pp. 1-25, 2072-2271, and 4481-4568, John Wiley & Sons Inc., 313 pages.

Chiang et al., "Carcinoembryonic antigen-related cell adhesion molecule 6 (CEACAM6) promotes EGF receptor signaling of oral squamous cell carcinoma metastasis via the complex N-glycosylation," Oncogene, Sep. 11, 2017, pp. 116-127, vol. 37, Macmillan Publishers, 12 pages.

Dolezal, S.J., "A Unique Glycan is a Specific Marker for Pancreatic Adenocarcinoma," May 2015, Athens, Georgia, 142 pages.

Holderness et al., "Abstract 2485: Novel monoclonal antibody targeting cancer stem cells," AACR 106th Annual Meeting, Apr. 18-22, 2015, Philadelphia, Pennsylvania, 3 pages.

Pierce et al., "Teams of the Alliance Synopsis," National Cancer Institute Division of Cancer Prevention, Athens, Geogia, 3 pages.

Sambrook et al., Molecular Cloning A Laboratory Manual, 1989, 2nd Ed., Cold Springs Harbor Laboratory Press, USA, 426 pages.

Sato et al., "Generation of a monoclonal antibody recognizing the CEACAM glycan structure and inhibiting adhesion using cancer tissue-originated spheroid", 15 pages.

Wu, et al., "N-acetylglucosaminyltransferase 5 (Mgat5) mediated N.-glycosylation of carcinoembryonic antigen-related cell adhesion molecule 6 (CEACAM6) enhances EGFT signaling of cell invasion and metastasis in head and neck cancer," European Journal of Cancer, 2016, vol. 61, 1 page.

Zhang, et al., "A Pentavalent Single-domain Antibody Approach to Tumor Antigen Discovery and the Development of Novel Proteomics Reagents," Journal of Molecular Biology, 2004, pp. 161-169, vol. 341, Elsevier Ltd., Ontario, Canada, 9 pages.

The extended European Search Report for European Application No. 17859752.2 mailed May 13, 2020, 8 pages.

The International Preliminary Report on Patentability for PCT Application No. PCT/SG2017/050509 mailed Jan. 16, 2018, 7 pages.

Kohls, et al., "Mab-Zap: A Tool for Evaluating Antibody Efficacy for Use in an Immunotoxin," BioTechniques, Jan. 2000, pp. 162-165, vol. 28, No. 1, 4 pages.

Tuominen, et al., "ImmunoRatio: a publicly available web application for quantitative image analysis of estrogen receptor (ER) progesterone receptor (PR), and Ki-67," Breast Cancer Research, 2010, Bio Med Central, 12 pages.

The first Written Opinion for Singaporean Application No. 11201903178Q mailed Mar. 16, 2020, 7 pages.

Cuzick, et al., "Tamoxifen for prevention of breast cancer: extended long-term follow-up of the IBIS-I breast cancer prevention trial," Lancet Oncology, Jan. 2015; 16(1) 67-75, 20 pages.

Shah, et al. World J Clin Oncol Aug. 10, 2014; 5(3): 283-298, 17 pages.

PCT International Search Report for PCT/SG2017/050509, mailed Jan. 26, 2018, 6 pages.

PCT Written Opinion of the International Searching Authority for PCT/SG2017/050509 mailed Jan. 26, 2018, 6 pages.

Non-Final Office Action for U.S. Appl. No. 16/341,052, mailed on Apr. 28, 2021, 14 pages.

Notice of Allowance for U.S. Appl. No. 16/341,052, mailed on Sep. 17, 2021, 8 pages.

Holliger and Hudson, Nature Biotechnology, Oct. 2005, vol. 23, No. 9, 1126-1136, 12 pages.

Notice of Reasons for Refusal, dated Sep. 15, 2021, issued in connection with Japanese Patent Application No. 2019-540505 [original document in Japanese and English language translation], 9 pages.

Sato et al., "Generation of a monoclonal antibody recognizing the CEACAM glycan structure and inhibiting adhesion using cancer tissue-originated spheroid as an antigen," Sci Rep 6:24823 (2016), 15 pages.

Written Opinion, dated Dec. 24, 2021, issued in connection with Japanese Patent Application No. 2019-540505 [original document in Japanese and English language translation], 10 pages.

Decision to Grant a Patent, dated Jan. 14, 2022, issued in connection with Japanese Patent Application No. 2019-540505 [original document in Japanese and English language translation], 5 pages.

Intention to Grant, dated Jun. 29, 2023, issued in connection with European Patent Application No. EP 17859752, 5 pages.

Non-Final Office Action for U.S. Appl. No. 17/560,232, mailed on Mar. 15, 2023, 10 pages.

Notice of Allowance for U.S. Appl. No. 17/560,232, mailed on Jul. 14, 2023, 8 pages.

First Office Action, dated Aug. 1, 2022, issued in connection with Chinese Patent Application No. 201780073296.1 [original document in Chinese and English language translation], 12 pages.

Notification to Grant Patent Right, dated Jan. 16, 2023, issued in connection with Chinese Patent Application No. 201780073296.1 [original document in Chinese and English language translation], 3 pages.

Written Opinion, dated Mar. 10, 2023, issued in connection with Korean Patent Application No. 20197012959 [original document in Korean and English language translation], 21 pages.

Written Decision on Registration, dated Jun. 19, 2023, issued in connection with Korean Patent Application No. 20197012959 [original document in Korean and English language translation], 6 pages.

\* cited by examiner

FIG. 3A

| Gefitinib sensitivity | Cell Line | Live (% binding) |
|---|---|---|
| Sensitive | PC-9 | ++++ |
| Acquired resistance | CL75 | +++ |
| Acquired resistance | CL86 | ++++ |
| Acquired resistance | CL131 | +++ |
| Acquired resistance | PC-9 GR | ++++ |

Legend:
-: <8%
+/-: 8 – 15%
+: 15 – 25%
++: 25 – 50%
+++: 50 – 75%
++++: 75 – 100%

FIG. 3B

| Gefitinib sensitivity | Cell Line | Live (% binding) |
|---|---|---|
| Resistant | A549 | + |
| Resistant | H1299 | - |
| Partially sensitive | Calu-3 | + |
| Sensitive | HCC827 | +/- |

FIG. 3C

| Gefitinib sensitivity | Cell Line | Live (% binding) |
|---|---|---|
| Sensitive | HCC827 | +/- |
| Acquired resistance | GR 1 | - |
| Acquired resistance | GR 2 | +++ |
| Acquired resistance | GR 3 | - |
| Acquired resistance | GR 4 | - |
| Acquired resistance | GR 5 | ++ |
| Acquired resistance | GR 6 | - |

FIG. 3D

| TNBC status | Cell line | Live (% binding) |
|---|---|---|
| HER+ | HCC1954 | +++ |
| HER+ | SKBR3 | - |
| HER+/PR+/ER+ | T47D | - |
| HER+/PR+/ER+ | MCF7 | - |
| HER+/PR+/ER+ | Cama-1 | - |
| HER+/PR+/ER+ | BT474 | ++++ |
| Triple-negative line | HCC1937 | + |
| Triple-negative line | BT20 | - |
| Triple-negative line | MB-231 | - |
| Triple-negative line | BT549 | - |
| Triple-negative line | Hs578T | - |
| Triple-negative line | MB-453 | - |
| Triple-negative line | HCC1395 | - |

Legend:
- : <8%
+/- : 8 – 15%
+ : 15 – 25%
++ : 25 – 50%
+++ : 50 – 75%
++++ : 75 – 100%

FIG. 3E

| Cell line | Live (% binding) |
|---|---|
| COLO205 | - |
| HT29 | +++ |

FIG. 3F

| Cell Type | Cell Line | Live (% binding) |
|---|---|---|
| Fibroblast | hFF | - |
| Fibroblast | MRC-5 | - |
| Embryonic | HEK293 | - |
| Stem Cell | aMSC | - |
| Endothelial | HUVEC | - |
| Endothelial | B4G12 | - |
| Epithelial | HME1 | - |
| Epithelial | MCF10a | - |
| Epithelial | HPNE | - |
| PBMC |  | - |

Legend:
- -: <8%
- +/-: 8-15%
- +: 15-25%
- ++: 25-50%
- +++: 50-75%
- ++++: 75-100%

FIG. 4B

Variable heavy chain (translated sequence, CDR underlined) (SEQ ID NO: 1)

```
-  S  G  P  E  L  V  K  P  G  A  S  V  K  M  S  C
K  A  S  G  N  T  F  T  S  Y  V  M  H  W  V  K
Q  K  P  G  Q  G  L  E  W  I  G  Y  I  N  P  Y
N  D  G  T  K  Y  N  E  K  F  K  G  K  A  T  L
T  S  D  K  S  S  S  T  A  Y  M  E  L  S  S  L
T  S  E  D  S  A  V  Y  Y  C  A  R  S  T  A  R
A  T  P  Y  F  Y  A  M  D  Y  W  G  Q  G  T  S
V  T  V  S  S
```

Variable light chain (translated sequence, CDR underlined) (SEQ ID NO: 2)

```
-  D  I  L  M  T  Q  S  P  S  S  L  A  V  T  A  G
E  K  V  T  M  R  C  K  S  S  Q  S  L  L  W  S
V  N  Q  N  S  Y  L  S  W  Y  Q  L  K  Q  G  Q
P  P  K  L  L  L  Y  G  A  S  I  R  E  S  W  V
P  D  R  F  T  G  S  G  S  G  T  D  F  T  L  T
I  S  N  V  H  V  E  D  L  A  V  Y  Y  C  Q  H
N  H  G  S  F  L  P  Y  T  F  G  G  G  T  K  L
E  I  K
```

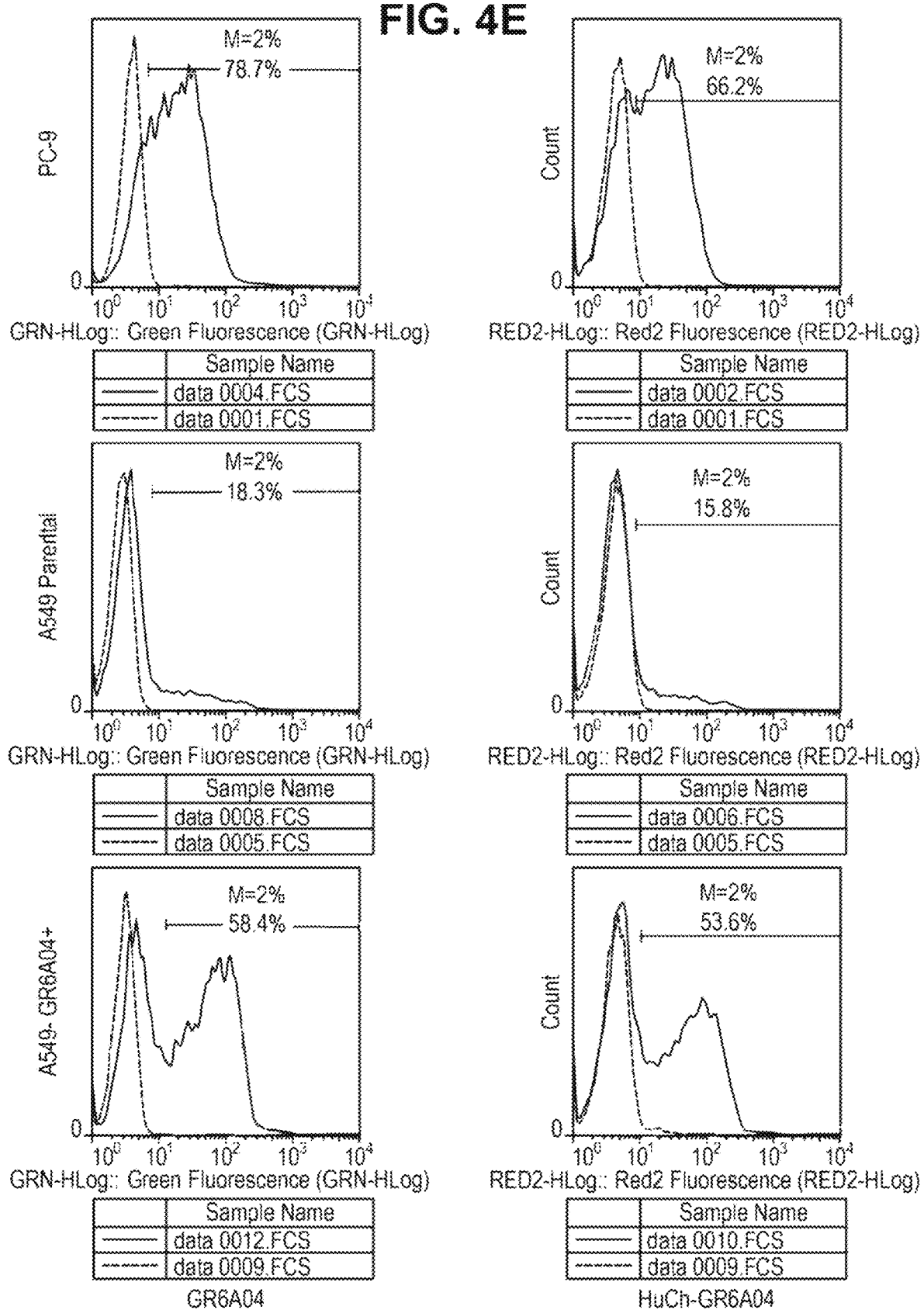

FIG. 6A

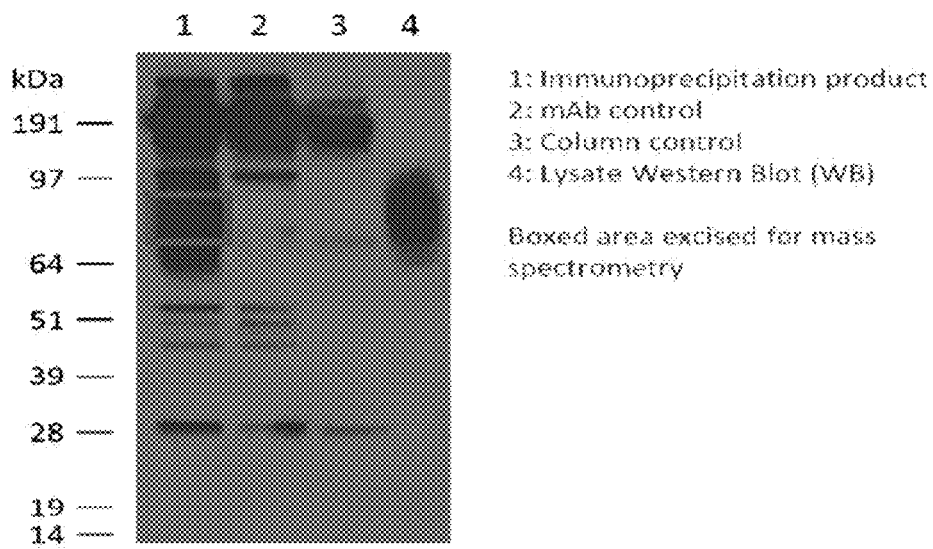

1: Immunoprecipitation product
2: mAb control
3: Column control
4: Lysate Western Blot (WB)

Boxed area excised for mass spectrometry

FIG. 6B

| Accession | Description | Score | Coverage | # Proteins | # Unique Peptides | # Peptides | # PSMs | # AAs | MW (kDa) | calc. pI |
|---|---|---|---|---|---|---|---|---|---|---|
| P11021 | 78 kDa glucose-regulated protein OS=Homo sapiens GN=HSPA5 PE=1 SV=2 - [GRP78_HUMAN] | 88.55 | 40.52 | 1 | 19 | 21 | 31 | 654 | 72.3 | 5.16 |
| P40199 | Carcinoembryonic antigen-related cell adhesion molecule 6 OS=Homo sapiens GN=CEACAM6 PE=1 SV=3 - [CEAM6_HUMAN] | 55.69 | 23.84 | 1 | 6 | 6 | 18 | 344 | 37.2 | 5.82 |
| P27824 | Calnexin OS=Homo sapiens GN=CANX PE=1 SV=2 - [CALX_HUMAN] | 45.65 | 26.35 | 2 | 12 | 12 | 15 | 592 | 67.5 | 4.60 |
| P40939 | Trifunctional enzyme subunit alpha, mitochondrial OS=Homo sapiens GN=HADHA PE=1 SV=2 - [ECHA_HUMAN] | 37.27 | 23.46 | 1 | 14 | 14 | 14 | 763 | 82.9 | 9.04 |
| O95202 | LETM1 and EF-hand domain-containing protein 1, mitochondrial OS=Homo sapiens GN=LETM1 PE=1 SV=1 - [LETM1_HUMAN] | 35.44 | 17.73 | 1 | 10 | 10 | 12 | 739 | 83.3 | 6.70 |

FIG. 8A

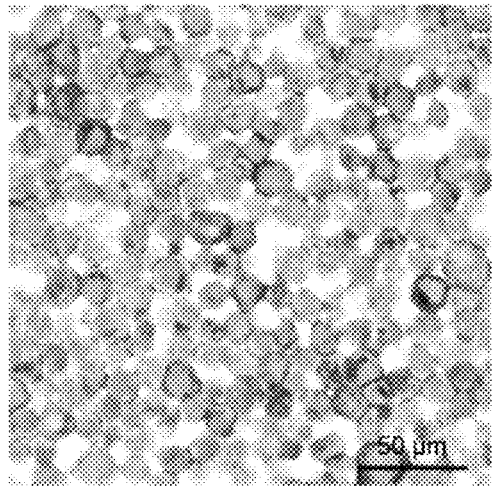

FIG. 8B

| | | | | | | | |
|---|---|---|---|---|---|---|---|
| | AGS Gastric Adenocarcinoma | H1299 Non-Small Cell Lung Cancer | MET-1 Skin Squamous Cell Carcinoma | HeLa Cervical Adeno carcinoma | HEK 293 (-) Embryonal Kidney, Normal | HES 3 (+) hESC | A-498 Kidney Epithelial Carcinoma |
| | 0/1+ | 0/1+ | 0/1+ | 0/1+ | 0/1+ | 0/1+ | 0/1+ |
| | PANC-1 Pancreatic Epithelioid Carcinoma | SJCRH30 Rhabdomyo sarcoma | LS 174T Colorectal Adeno carcinoma | OVCAR-3 Ovarian Adeno carcinoma | HFF-1 (-) Human Foreskin Fibroblast | NEB-1 (-) Keratinocyte/ fibroblast mix | MCF-7 Breast Cancer |
| | 0/1+ | 0/1+ | 2+ | 0/1+ | 0/1+ | 0/1+ | 0/1+ |
| | A549 Lung Cancer | MET-2 Skin cancer, SCC | SSC-12 Skin Squamous Cell Carcinoma | SNU-16 Stomach Cancer | 786-0 Kidney Cancer | T-24 Bladder Cancer | Hep G2 Liver Cancer |
| | 2+ | 0/1+ | 0/1+ | 3+ | 0/1+ | 0/1+ | 0/1+ |
| | TR-146 Buccal Cancer | HaCaT(-) Keratinocyte Normal | HEY A8 Ovarian Cancer | SCC 13 Skin Squamous Cell Carcinoma | A172 Glioblastoma | MNNG P5 Osteosarcoma | KEB 7 Keratinocyte |
| | 0/1+ | 0/1+ | 0/1+ | 0/1+ | 0/1+ | 0/1+ | 0/1+ |
| | BxPC3 Pancreatic Cancer | COLO 205 Colon Cancer | MET-4 Skin Squamous Cell Carcinoma | MDA-231 Breast Cancer | SW 1353 Chondrosarco ma | PLC-PRF-5 Hepatoma | 2102 EP Testicular Embryonal Carcinoma |
| | 2+ | 2+ | 0/1+ | 0/1+ | 0/1+ | 0/1+ | 0/1+ |
| | Saos-2C Osteosarcoma | J-82 Bladder Cancer | U-87MG Glioblastoma | IMR90 (-) Lung, Normal | HFF Stem Cells | Saos-2 Osteosarcoma | ACHN Kidney Renal Cell Carcinoma |
| | 0/1+ | 0/1+ | 0/1+ | 0/1+ | 0/1+ | 0/1+ | 0/1+ |

FIG. 9
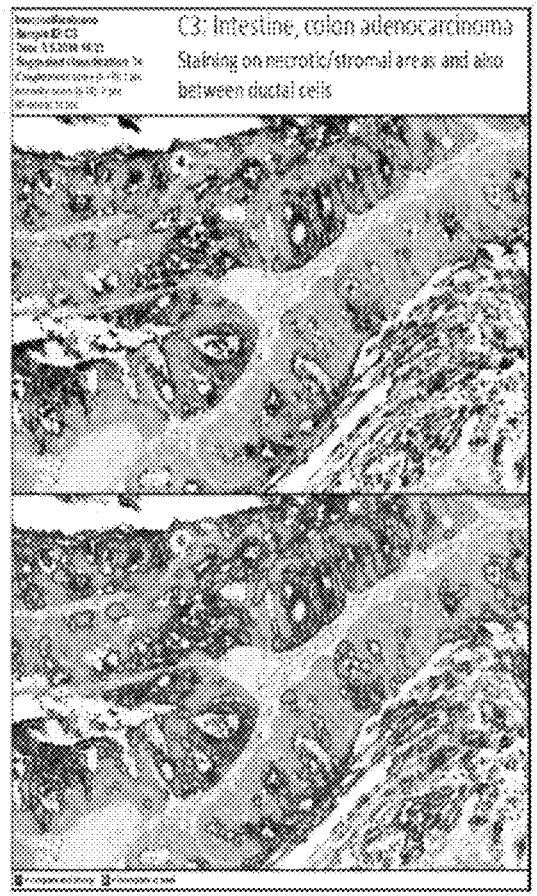
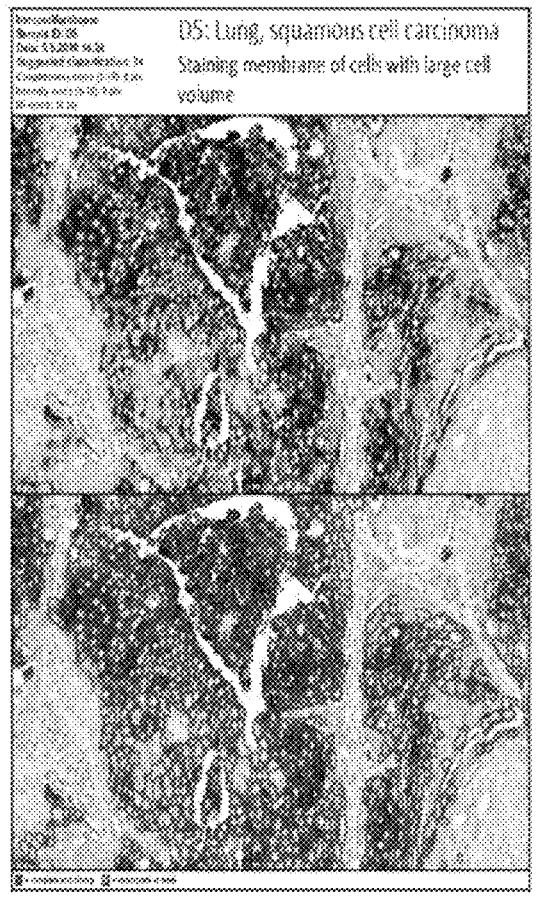

FIG. 10

| | 1 | 2 | 3 | 4 | 5 | 6 | 7 | 8 |
|---|---|---|---|---|---|---|---|---|
| A | Bladder, urinary Transitional cell carcinoma Gr II, T4N0M0 | Breast Invasive ductal carcinoma, tubular type Gr I-II, T3N0M0 | Lung Small cell carcinoma T2N1M0 | Esophagus Squamous cell carcinoma Gr II, T2N1M0 | Intestine, colon Adeno carcinoma Gr II, T3N1M0 | Liver Hepato cellular carcinoma Gr I-II, T2N0M0 | Ovary Endometrioid adeno carcinoma Gr III, T2N0M0 | Prostate Hyperplasia |
| | 0/1+ | 0/1+ | 0/1+ | | | 0/1+ | 0/1+ | 0/1+ |
| B | Bladder, urinary Transitional cell carcinoma Gr II, T3N0M0 | Breast Invasive lobular carcinoma Gr I, T3N1M0 | Lung Squamous cell carcinoma Gr II-III, T2N0M0 | Esophagus Squamous cell carcinoma Gr I-II, T3N0M0 | Intestine, colon Adeno carcinoma Gr II, T3N1M0 | Liver Hepato cellular carcinoma Gr II, T4N0M0 | Ovary Serous cystadeno carcinoma Gr I-II, T2N0M0 | Prostate Adeno carcinoma Gr I-II, T2N0M0 |
| | 0/1+ | 0/1+ | 0/1+ | | | 0/1+ | 0/1+ | 0/1+ |
| C | Bladder, urinary Transitional cell carcinoma Gr I-II, T2N0M0 | Breast Invasive ductal carcinoma Gr II, T3N1M0 | Lung Squamous cell carcinoma Gr II, T2N1M0 | Stomach Adeno carcinoma Gr II, T3N2M0 | Intestine, colon Adeno carcinoma Gr III, T3N2M0 | Liver Hepato cellular carcinoma Gr III, T3N0M0 | Ovary Adeno carcinoma Gr II, T2N0M0 | Skin Normal |
| | 0/1+ | 0/1+ | 0/1+ | 0/1+ | 0/1+ | 0/1+ | 0/1+ | 0/1+ |
| D | Uterus, cervix Squamous cell carcinoma Gr III, T1N1M0 | Breast Invasive ductal carcinoma Gr I, T4N1M0 | Lung Adeno carcinoma Gr II-III, T3N1M0 | Stomach Adeno carcinoma Gr II-III, T3N2M0 | Intestine, rectum Adeno carcinoma Gr II, T2N0M0 | Kidney Clear cell carcinoma T1N0M0 | Uterus, endometrium Adeno carcinoma Gr II, T1N0M0 | Skin Squamous cell carcinoma Gr I-II, T1N0M0 |
| | 0/1+ | 0/1+ | | 0/1+ | | 0/1+ | 0/1+ | 0/1+ |
| E | Uterus, cervix Squamous cell carcinoma Gr II-III, T2N0M0 | Breast Invasive ductal carcinoma Gr III, T2N1M0 | Lung Adeno carcinoma Gr III, T2N1M0 | Stomach Adeno carcinoma Gr II, T3N2M0 | Intestine, rectum Adeno carcinoma Gr II, T2N0M0 | Kidney Clear cell carcinoma T1N0M0 | Uterus, endometrium Adeno carcinoma Gr I-II, T2N0M0 | Lympyh node, inguinal Metastatic melanoma |
| | 0/1+ | 0/1+ | 0/1+ | 0/1+ | | 0/1+ | | 0/1+ |
| F | Uterus, cervix Squamous cell carcinoma Gr III, T1N0M0 | Breast Invasive ductal carcinoma Gr III, T3N0M0 | Lung Adeno carcinoma Gr II-III, T3N0M0 | Intestine, small intestine Adeno carcinoma Gr I, T3N2M0 | Intestine, rectum Adeno carcinoma Gr II, T2N0M0 | Kidney Clear cell carcinoma T2N0M0 | Uterus, endometrium Adeno carcinoma Gr III, T1N0M0 | Tonsil Tonsillitis |
| | 0/1+ | 0/1+ | 0/1+ | | | 0/1+ | 0/1+ | 0/1+ |

FIG. 10 (cont'd)
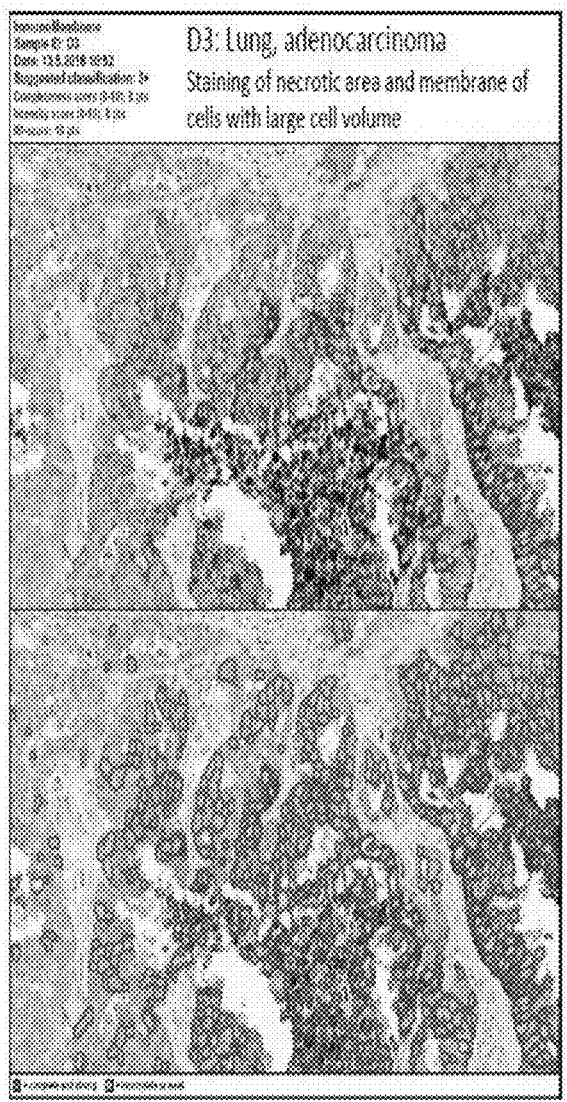
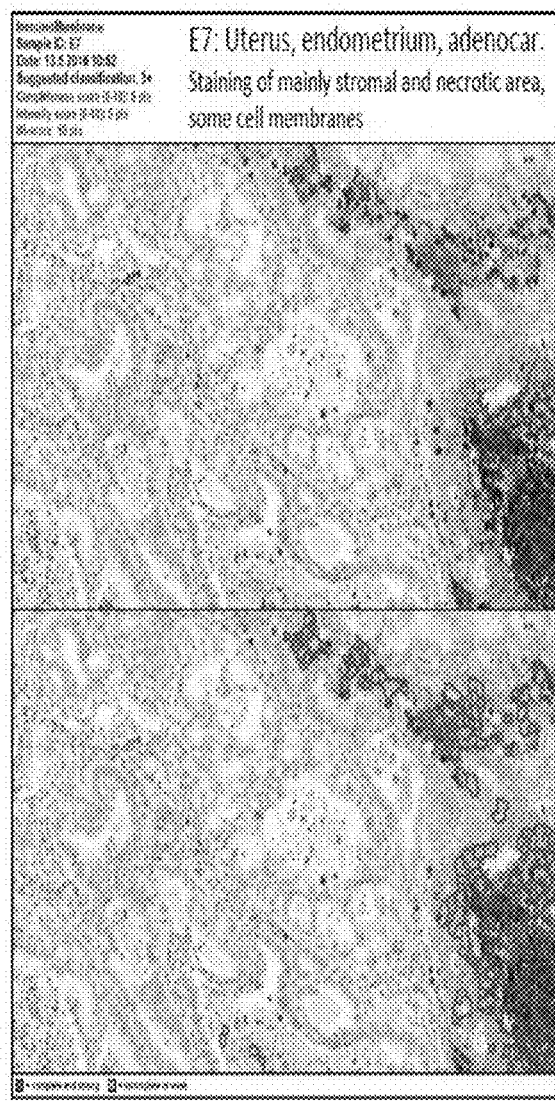

FIG. 10 (cont'd)
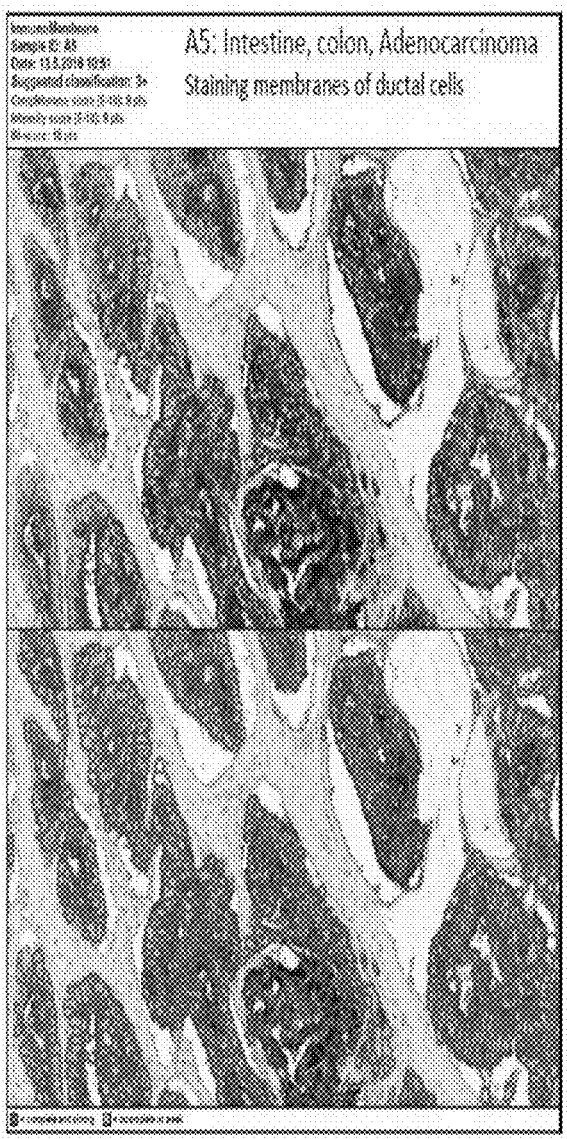
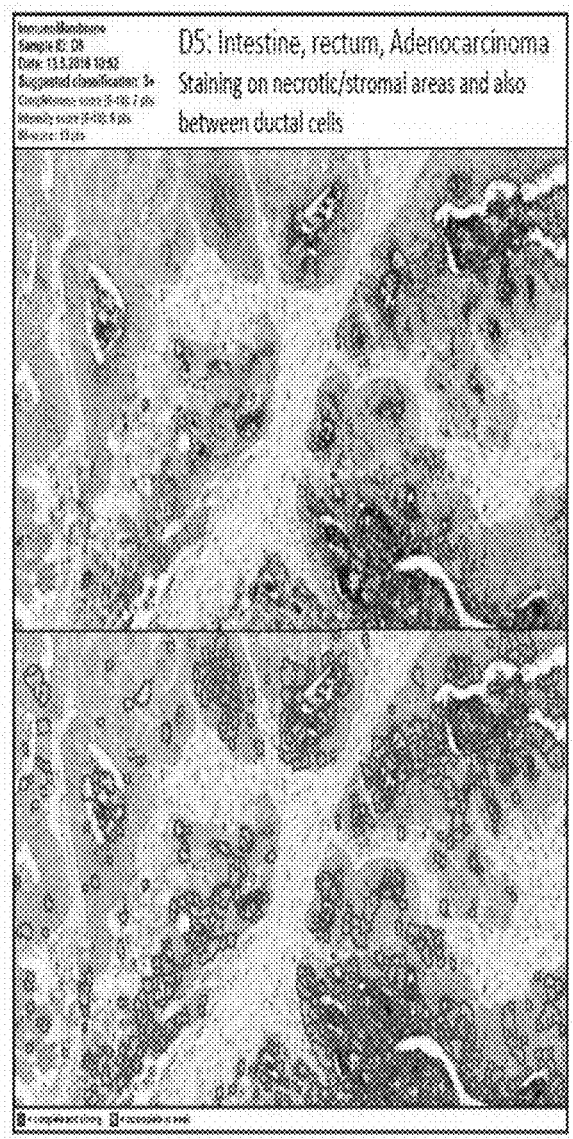

FIG. 10 (cont'd)
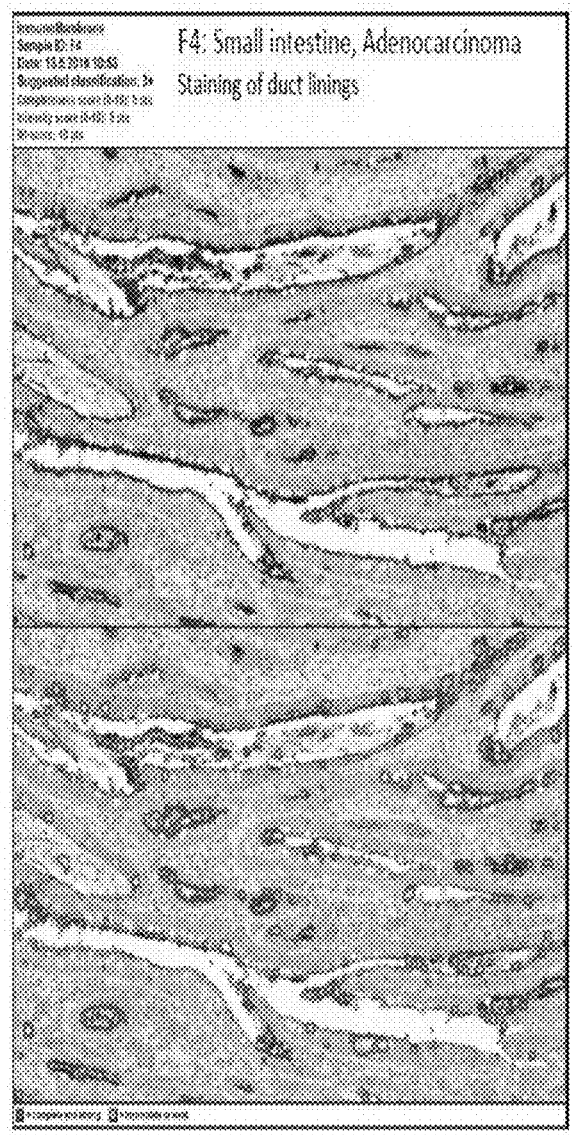

FIG. 11A

| | 1 | 2 | 3 | 4 | 5 | 6 | 7 | 8 | 9 | 10 | 11 | 12 |
|---|---|---|---|---|---|---|---|---|---|---|---|---|
| A | Adrenal gland | Adrenal gland | Adrenal gland | Bladder, urinary | Bladder, urinary | Bladder, urinary | Breast | Breast | Breast | Breast | Breast | Breast |
| Diagnosis | Normal, hyperplasia | Adenoma, cortical | Adreno cortical carcinoma | Normal | Transitional cell carcinoma | Transitional cell carcinoma | Normal | Fibro adenoma | Fibro adenoma | Invasive ductal carcinoma | Invasive ductal carcinoma | Invasive ductal carcinoma |
| Grade | | | | | I | I | | | | II | II | II |
| TMN | | | T2N0M0 | | T1N0M0 | T1N0M0 | | | | T2N1M0 | T2N0M0 | T4N1M0 |
| Score | 0/1+ | 0/1+ | 0/1+ | 0/1+ | 0/1+ | 0/1+ | 0/1+ | 0/1+ | 0/1+ | 0/1+ | 2+ | 0/1+ |
| B | Bone, tibia | Bone, scapula | Brain, cerebellum | Brain, cerebellum | Brain, cerebellum | Brain | Brain | Brain | Esophagus | Esophagus | Esophagus | Esophagus |
| Diagnosis | Osteo sarcoma | Chondro sarcoma | Normal | Meningioma, fibroblastic | Malignant meningioma | Normal | Meningioma, fibroblastic | Astrocytoma | Normal | Squamous cell carcinoma | Squamous cell carcinoma | Squamous cell carcinoma |
| Grade | | | | | | | | II | | I | II | III |
| TMN | | | | | | | | | | T2N0M0 | T3N1M0 | T2N1M0 |
| Score | 0/1+ | 0/1+ | 0/1+ | 0/1+ | 0/1+ | 0/1+ | 0/1+ | 2+ | 0/1+ | 0/1+ | 0/1+ | 2+ |
| C | Stomach | Stomach | Stomach | Stomach | Intestine, small intestine | Intestine, small intestine | Intestine, small intestine | Intestine, colon | Intestine, colon | Intestine, colon | Intestine, colon | Intestine, colon |
| Diagnosis | Normal | Adeno carcinoma | Adeno carcinoma | Adeno carcinoma | Normal | Adenoma | Adeno carcinoma | Normal | Adenoma | Adeno carcinoma | Adeno carcinoma | Adeno carcinoma |
| Grade | | I | II | III | | | II | | I | II | III |
| TMN | | T2N0M0 | T3N1M0 | T3N2M0 | | | T2N0M0 | | | T3N0M0 | T2N0M0 | T3N0M0 |
| Score | 0/1+ | 3+ | 0/1+ | 0/1+ | 0/1+ | 0/1+ | 0/1+ | 0/1+ | 2+ | 3+ | 2+ |
| D | Intestine, rectum | Intestine, rectum | Intestine, rectum | Intestine, rectum | Kidney | Kidney | Kidney | Liver | Liver | Liver | Liver | Liver |
| Diagnosis | Normal | Adeno carcinoma | Adeno carcinoma | Adeno carcinoma | Normal cortex | Clear cell carcinoma | Clear cell carcinoma | Normal | Hepato cellular carcinoma | Hepato cellular carcinoma | Hepato cellular carcinoma | Hepato cellular carcinoma |
| Grade | | I | II | III | | | | | I | II | I | III |
| TMN | | T3N0M0 | T3N1M0 | T3N1M0 | | T1N0M0 | T1N0M0 | | T2N0M0 | T2N0M0 | T2N0M0 | T2N0M0 |
| Score | 2+ | 3+ | 2+ | 3+ | 0/1+ | 0/1+ | 0/1+ | 0/1+ | 0/1+ | 0/1+ | 0/1+ | 0/1+ |

FIG. 11A (cont'd)

| | 1 | 2 | 3 | 4 | 5 | 6 | 7 | 8 | 9 | 10 | 11 | 12 |
|---|---|---|---|---|---|---|---|---|---|---|---|---|
| E | Lung | Lung | Lung | Lung | Lung | Lymph node | Lymph node, neck | Lymph node, axillary | Lymph node, neck | Head and neck, | Head and neck, | Head and neck, |
| Diagnosis | Normal | Squamous cell carcinoma | Squamous cell carcinoma | Adeno carcinoma | Small cell carcinoma | Reactive | Lymphoma, Hodgkin lymphoma | Lymphoma, non-Hodgkin B-cell lymphoma | Lymphoma, anaplastic large cell lymphoma | Adeno carcinoma | Squamous cell carcinoma | Naso pharyngeal carcinoma, NPC |
| Grade | | II | II-III | III | | | | | | III-IV | II | III |
| TMN | | T2N2M0 | T2N0M0 | T2N2M0 | T3N0M0 | | | | | | T2N0M0 | T2N0M0 |
| Score | 2+ (false+) | 0/1+ | 0/1+ | 0/1+ | 0/1+ | 0/1+ | 0/1+ | 0/1+ | 0/1+ | 0/1+ | 2+ | 0/1+ |
| F | Ovary | Ovary | Ovary | Ovary | Pancreas | Pancreas | Prostate | Prostate | Prostate | Head and neck, | Head and neck, | Head and neck, |
| Diagnosis | Normal | Granulosa cell tumor | Adeno carcinoma | Endometrioid adeno carcinoma | Normal | Adeno carcinoma | Normal, hyperplasia | Adeno carcinoma | Adeno carcinoma | Normal | Pleo morphic adenoma | Adenoid cystic carcinoma |
| Grade | | | III | III | | II | | II | III | | | I-II |
| TMN | | | T2N0M0 | T1N0M0 | | T3N1M1 | | T2N0M0 | T3N0M0 | | | T1N0M0 |
| Score | 0/1+ | 0/1+ | 0/1+ | 0/1+ | 0/1+ | 0/1+ | 0/1+ | 0/1+ | 0/1+ | 0/1+ | 0/1+ | 0/1+ |
| G | Skin | Skin, trunk | Head and neck, | Testis | Testis | Testis | Thyroid | Thyroid | Thyroid | Thyroid | Thyroid | Thyroid |
| Diagnosis | Normal | Squamous cell carcinoma | Melanoma | Normal | Seminoma | Seminoma | Normal | Adenoma | Adenoma | Adenoma | Follicular carcinoma | Follicular papillary adeno carcinoma |
| Grade | | II | | | | | | | | | | |
| TMN | | T2N0M0 | | | | | | | | | T3N1M0 | T2N1M0 |
| Score | 0/1+ | 0/1+ | 0/1+ | 0/1+ | 0/1+ | 0/1+ | 0/1+ | 0/1+ | 0/1+ | 2+ (false+) | 0/1+ | |
| H | Uterus, cervix | Uterus, cervix | Uterus, cervix | Uterus, endometrium | Uterus, endometrium | Uterus, endometrium | Liver | Lung | Lymph node | Ovary | Lymph node | |
| Diagnosis | Normal | Squamous cell carcinoma | Squamous cell carcinoma | Normal | Adeno carcinoma | Adeno carcinoma | Metastatic colon adeno carcinoma | Metastatic cancers, from gastro intestinal site? | Metastatic breast invasive ductal carcinoma | Metastatic colon signet ring cell carcinoma | Metastatic esophagus squamous cell carcinoma | |
| Grade | | III | III | | I-II | II-III | | | | | | |
| TMN | | T3N0M0 | T1N1M0 | | T2N0M0 | T1N1M0 | | | | | | |
| Score | 0/1+ | 0/1+ | 2+ | 0/1+ | 2+ | 0/1+ | 3+ | 0/1+ | 0/1+ | 2+ | 0/1+ | |

FIG. 11A (cont'd)

| Cancer tissue type | Cores stained |
|---|---|
| Breast | 1/5 |
| Gastro-intestinal | 8/15 |
| Head & neck | 1/6 |
| Uterus | 2/4 |
| Metastatic secondary | 2/5 |

FIG. 11B
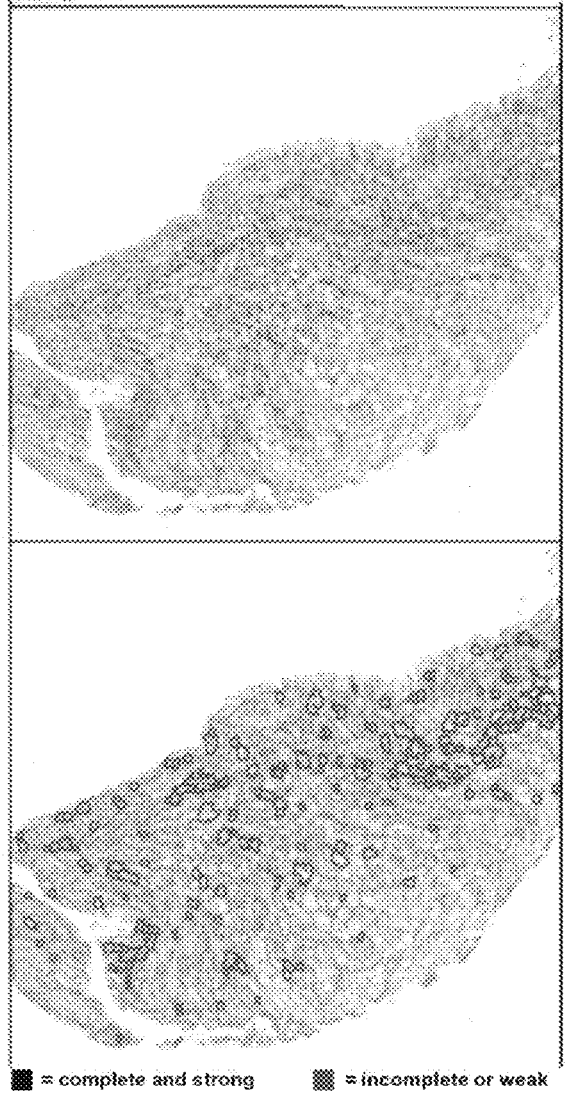
B09: Esophageal, Normal
Weak spotty staining between cells
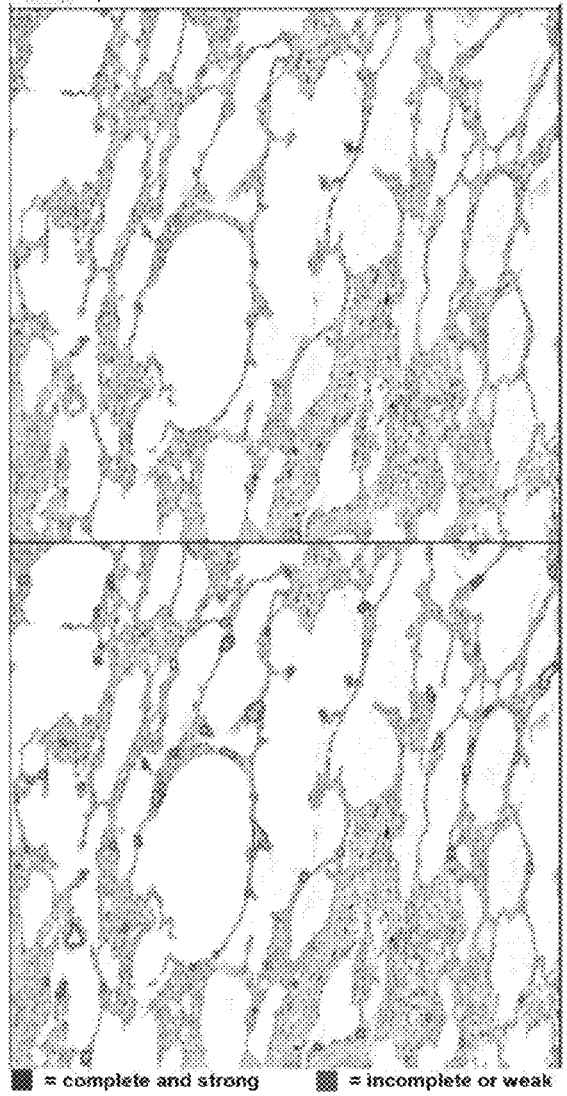
E01: Lung, Normal
False positive scoring by ImmunoMembrane

FIG. 12

| | 1 | 2 | 3 | 4 | 5 | 6 | 7 | 8 | 9 | 10 |
|---|---|---|---|---|---|---|---|---|---|---|
| A | Squamous cell carcinoma | Pulmonary edema | Squamous cell carcinoma | Cancer adjacent lung tissue | Squamous cell carcinoma | Cancer adjacent lung tissue | Squamous cell carcinoma with necrosis (sparse) | Cancer adjacent lung tissue | Squamous cell carcinoma | Cancer adjacent lung tissue |
| Grade | 1 | - | 1 | - | 2 | - | 2 | - | 2 | - |
| Stage | I | - | I | - | I | - | I | - | II | - |
| TMN | T2N0M0 | - | T2N0M0 | - | T2N0M0 | - | T2N0M0 | - | T2N1M0 | - |
| Type | Malignant | AT | Malignant | AT | Malignant | AT | Malignant | AT | Malignant | AT |
| Score | 0/1+ | 0/1+ | 0/1+ | 0/1+ | 0/1+ | 0/1+ | 0/1+ | 0/1+ | 0/1+ | 0/1+ |
| B | Squamous cell carcinoma and cartilage tissue | Lung congestion | Squamous cell carcinoma | Pulmonary alveolus interstitial fibroplasia | Squamous cell carcinoma with necrosis | Cancer adjacent lung tissue | Squamous cell carcinoma with necrosis | Cancer adjacent lung tissue | Squamous cell carcinoma | Cancer adjacent lung tissue |
| Grade | 2 | - | 3 | - | 2 | - | 3 | - | 2 | - |
| Stage | I | - | I | - | II | - | IIIA | - | II | - |
| TMN | T2N0M0 | - | T2N0M0 | - | T2N1M0 | - | T3N0M0 | - | T2N1M0 | - |
| Type | Malignant | AT | Malignant | AT | Malignant | AT | Malignant | AT | Malignant | AT |
| Score | 0/1+ | 0/1+ | 0/1+ | 0/1+ | 2+ | 3+ Focal +1 | 0/1+ | 0/1+ | 0/1+ | 0/1+ |
| C | Squamous cell carcinoma | Cancer adjacent lung tissue | Squamous cell carcinoma | Cancer adjacent lung tissue | Squamous cell carcinoma | Cancer adjacent lung tissue | Squamous cell carcinoma | Cancer adjacent lung tissue | Squamous cell carcinoma | Cancer adjacent lung tissue |
| Grade | 2 | - | 2 | - | - | - | 2 | - | 2 | - |
| Stage | IIIA | - | I | - | II | - | II | - | IV | - |
| TMN | T2N0M0 | - | T2N0M0 | - | T2N1M0 | - | T2N1M0 | - | T2N1M1 | - |
| Type | Malignant | AT | Malignant | AT | Malignant | AT | Malignant | AT | Malignant | AT |
| Score | 0/1+ | 0/1+ | 2+ | 0/1+ | 0/1+ | 0/1+ | 0/1+ | 0/1+ | 0/1+ | 0/1+ |
| D | Squamous cell carcinoma | Cancer adjacent lung tissue | Squamous cell carcinoma | Cancer adjacent lung tissue | Squamous cell carcinoma | Cancer adjacent lung tissue | Squamous cell carcinoma | Cancer adjacent lung tissue | Squamous cell carcinoma | Cancer adjacent lung tissue |
| Grade | - | - | 3 | - | - | - | 3 | - | 3 | - |
| Stage | IIA | - | IIB | - | I | - | IIIA | - | I | - |
| TMN | T2N0M0 | - | T2N0M0 | - | T2N0M0 | - | T2N2M0 | - | T2N0M0 | - |
| Type | Malignant | AT | Malignant | AT | Malignant | AT | Malignant | AT | Malignant | AT |
| Score | 0/1+ | 0/1+ | 0/1+ | 0/1+ | 2+ | 0/1+ | 0/1+ | 0/1+ | 2+ | 0/1+ |
| E | Squamous cell carcinoma | Cancer adjacent lung tissue | Squamous cell carcinoma | Pulmonary alveolus interstitial fibroplasia | Squamous cell carcinoma | Cancer adjacent lung tissue | Squamous cell carcinoma | Cancer adjacent lung tissue | Squamous cell carcinoma | Cancer adjacent lung tissue |
| Grade | 2 | - | 3 | - | - | - | 3 | - | 3 | - |
| Stage | I | - | II | - | IIIB | - | II | - | II | - |
| TMN | T2N0M0 | - | T2N1M0 | - | T4N1M0 | - | T2N1M0 | - | T2N1M0 | - |
| Type | Malignant | AT | Malignant | AT | Malignant | AT | Malignant | AT | Malignant | AT |
| Score | 0/1+ | 0/1+ | 0/1+ | 0/1+ | 0/1+ | 0/1+ | 0/1+ | 0/1+ | 0/1+ | 0/1+ |

FIG. 12 (cont'd)

| | 1 | 2 | 3 | 4 | 5 | 6 | 7 | 8 | 9 | 10 |
|---|---|---|---|---|---|---|---|---|---|---|
| F | Squamous cell carcinoma | Cancer adjacent lung tissue | Adenosqua mous carcinoma | Cancer adjacent lung tissue | Mucinous adenocarcin oma | Cancer adjacent lung tissue | Adenocarcin oma | Cancer adjacent lung tissue | Adenocarcin oma | Cancer adjacent lung tissue |
| Grade | 3 | - | - | - | 1 | - | 2 | - | 2 | - |
| Stage | I | - | II | - | IIIA | - | IIIA | - | I | - |
| TMN | T2N0M0 | - | T2N1M0 | - | T2N0M0 | - | T3N0M0 | - | T2N0M0 | - |
| Type | Malignant | AT | Malignant | AT | Malignant | AT | Malignant | AT | Malignant | AT |
| Score | 0/1+ | 0/1+ | 0/1+ | 0/1+ | 0/1+ | 0/1+ | 0/1+ | 0/1+ | 3+ | 0/1+ |
| G | Adenocarcin oma | Cancer adjacent lung tissue | Adenocarcin oma | Cancer adjacent lung tissue | Mucinous adenocarcin oma | Cancer adjacent lung tissue | Adenocarcin oma | Cancer adjacent lung tissue | Adenocarcin oma | Cancer adjacent lung tissue |
| Grade | 2 | - | 2 | - | 1 | - | 2 | - | 2 | - |
| Stage | I | - | II | - | IIIA | - | I | - | II | - |
| TMN | T2N0M0 | - | T2N1M0 | - | T3N0M0 | - | T2N0M0 | - | T2N0M0 | - |
| Type | Malignant | AT | Malignant | AT | Malignant | AT | Malignant | AT | Malignant | AT |
| Score | 2+ | 0/1+ | 2+ | 0/1+ | 2+ | 0/1+ | 0/1+ | 0/1+ | 2+ | 0/1+ |
| H | Adenocarcin oma | Cancer adjacent lung tissue | Adenocarcin oma | Cancer adjacent lung tissue | Adenocarcin oma | Cancer adjacent lung tissue | Papillary adenocarcin oma | Cancer adjacent lung tissue | Papillary adenocarcin oma | Cancer adjacent lung tissue |
| Grade | 2 | - | 2 | - | 2 | - | 2 | - | 2 | - |
| Stage | II | - | II | - | I | - | I | - | IIIA | - |
| TMN | T2N1M0 | - | T2N1M0 | - | T2N0M0 | - | T2N0M0 | - | T2N1M0 | - |
| Type | Malignant | AT | Malignant | AT | Malignant | AT | Malignant | AT | Malignant | AT |
| Score | 0/1+ | 0/1+ | 0/1+ | 0/1+ | 2+ | 0/1+ | 0/1+ | 0/1+ | 3+ | 0/1+ |
| I | Adenocarcin oma | Cancer adjacent lung tissue | Adenocarcin oma | Cancer adjacent lung tissue | Adenocarcin oma | Cancer adjacent lung tissue | Adenocarcin oma | Cancer adjacent lung tissue | Adenocarcin oma | Cancer adjacent lung tissue |
| Grade | 2 | - | 3 | - | 3 | - | 3 | - | 3 | - |
| Stage | II | - | I | - | I | - | II | - | I | - |
| TMN | T2N1M0 | - | T2N0M0 | - | T2N0M0 | - | T2N1M0 | - | T2N0M0 | - |
| Type | Malignant | AT | Malignant | AT | Malignant | AT | Malignant | AT | Malignant | AT |
| Score | 0/1+ | 0/1+ | 2+ | 0/1+ | 0/1+ | 0/1+ | 0/1+ | 0/1+ | 2+ | 0/1+ |
| J | Lung tissue | Lung tissue | Lung tissue | Lung tissue | Lung tissue | Lung tissue | Lung tissue | Lung tissue | Lung tissue | Lung tissue |
| Grade | - | - | - | - | - | - | - | - | - | - |
| Stage | - | - | - | - | - | - | - | - | - | - |
| TMN | - | - | - | - | - | - | - | - | - | - |
| Type | Normal | Normal | Normal | Normal | Normal | Normal | Normal | Normal | Normal | Normal |
| Score | 0/1+ | 0/1+ | 0/1+ | 0/1+ | 0/1+ | 0/1+ | 0/1+ | 0/1+ | 0/1+ | 0/1+ |

FIG. 14

| | 1 | 2 | 3 | 4 | 5 | 6 | 7 | 8 | 9 | 10 | 11 | 12 |
|---|---|---|---|---|---|---|---|---|---|---|---|---|
| A | Adrenal gland* Normal 0/1+ | Adrenal gland* Normal 0/1+ | Adrenal gland* Normal 0/1+ | Bladder Normal 0/1+ | Bladder Normal 0/1+ | Bladder Normal 0/1+ | Bone marrow* Normal 0/1+ | Eye* Normal 0/1+ | Eye* Normal 0/1+ | Breast Normal 0/1+ | Breast Normal 0/1+ | Breast Normal 0/1+ |
| B | Cerebellum* Normal 0/1+ | Cerebellum* Normal 0/1+ | Cerebellum* Normal 0/1+ | Cerebral cortex* Normal 0/1+ | Cerebral cortex* Normal 0/1+ | Cerebral cortex* Normal 0/1+ | Fallopian tube Normal 0/1+ | Fallopian tube Normal 0/1+ | Fallopian tube Normal 0/1+ | GI-Esophagus Normal 0/1+ | GI-Esophagus Normal 0/1+ | GI-Esophagus Normal 0/1+ |
| C | GI-Stomach Normal 0/1+ | GI-Stomach Normal 0/1+ | GI-Stomach Normal 0/1+ | GI-Small intestine Normal 0/1+ | GI-Small intestine Normal 0/1+ | GI-Small intestine Normal 0/1+ | GI-Colon Normal 0/1+ | GI-Colon Normal 2+ | GI-Colon Normal 2+ | GI-Rectum Normal 0/1+ | GI-Rectum Normal 0/1+ | GI-Rectum Normal 0/1+ |
| D | Heart* Normal 0/1+ | Heart* Normal 0/1+ | Heart* Normal 0/1+ | Kidney Normal 0/1+ | Kidney Normal 0/1+ | Kidney Normal 0/1+ | Kidney Normal 0/1+ | Kidney Normal 0/1+ | Liver Normal 0/1+ | Liver Normal (cell swelling) 0/1+ | Liver Normal 0/1+ | |
| E | Lung Normal 0/1+ | Lung Normal 0/1+ | Lung Normal 0/1+ | Ovary Normal 0/1+ | Ovary Normal 0/1+ | Ovary Normal 0/1+ | Pancreas* Normal 0/1+ | Pancreas* Normal 0/1+ | Pancreas* Normal 0/1+ | Parathyroid Adenoma 0/1+ | Pituitary gland* Normal 0/1+ | Pituitary gland* Normal 0/1+ |
| F | Placenta Normal 0/1+ | Placenta Normal 0/1+ | Placenta Normal 0/1+ | Prostate Normal 2+ | Prostate Normal 0/1+ | Prostate Normal 0/1+ | Skin Normal 0/1+ | Skin Normal 0/1+ | Spinal cord* Normal 0/1+ | Spinal cord* Normal 0/1+ | Spleen Normal 0/1+ | Spleen Normal 0/1+ |
| G | Striated muscle* Normal 0/1+ | Striated muscle* Normal 0/1+ | Striated muscle* Normal 0/1+ | Testis Normal 0/1+ | Testis Normal 0/1+ | Testis Normal 0/1+ | Thymus* Normal 0/1+ | Thymus* Normal 0/1+ | Thymus* Normal 0/1+ | Thyroid Normal 0/1+ | Thyroid Normal 0/1+ | Thyroid Normal 0/1+ |
| H | Tonsil Normal 0/1+ | Tonsil Normal 0/1+ | Tonsil Normal 0/1+ | Ureter Normal 0/1+ | Ureter Normal 0/1+ | Ureter Normal 0/1+ | Uterus-cervix Normal 0/1+ | Uterus-cervix Normal 0/1+ | Uterus-cervix Normal 0/1+ | Uterus-endometrium Normal 0/1+ | Uterus-endometrium Normal 0/1+ | Uterus-endometrium Normal 0/1+ |

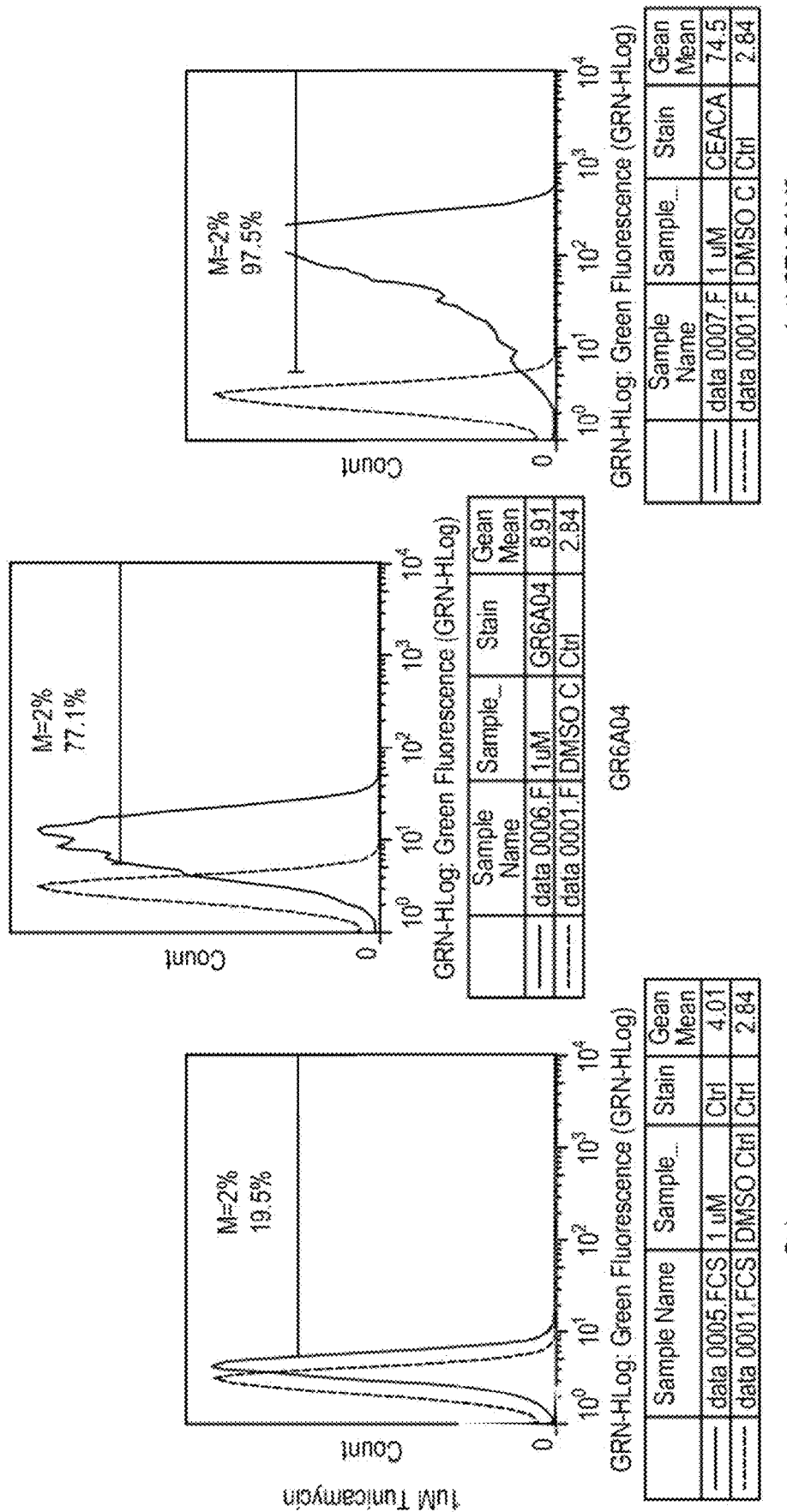

FIG. 15D
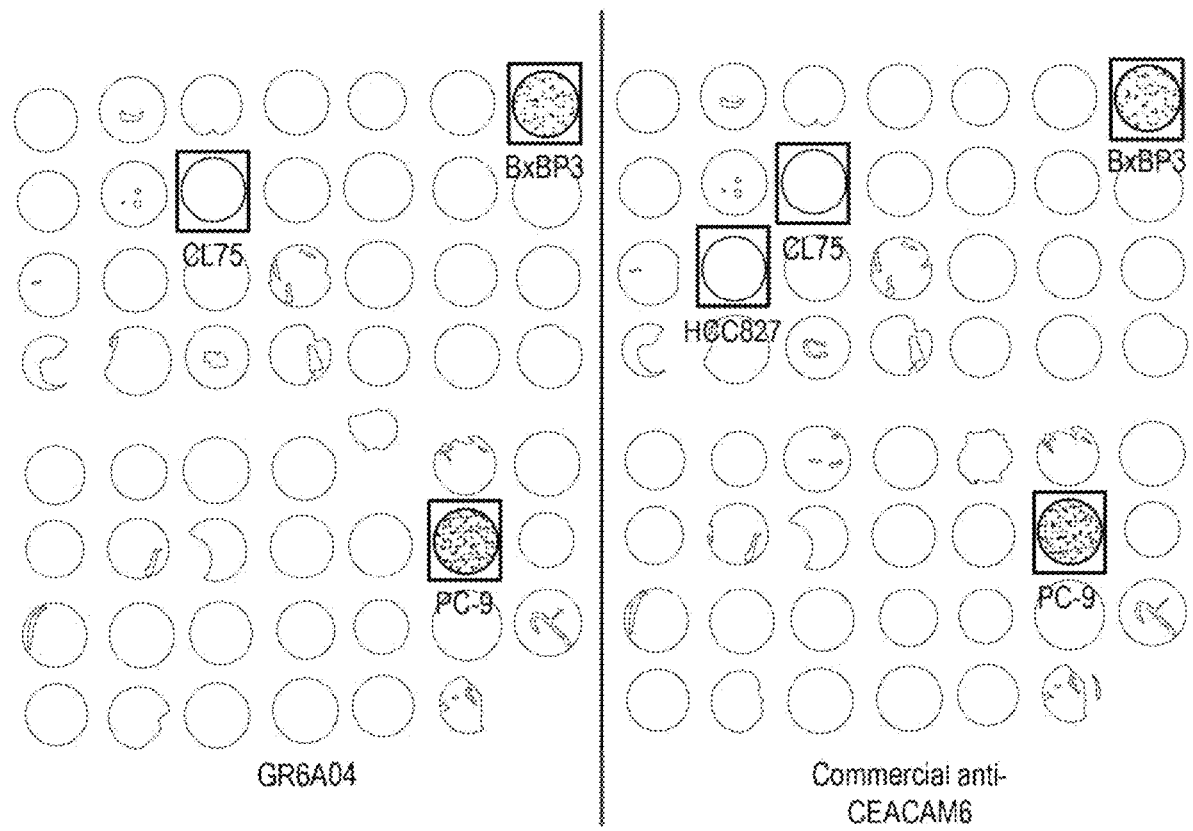
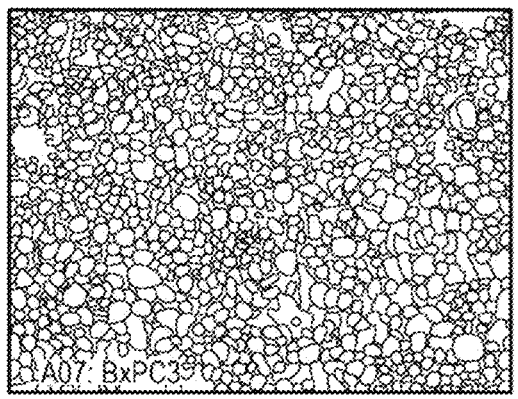
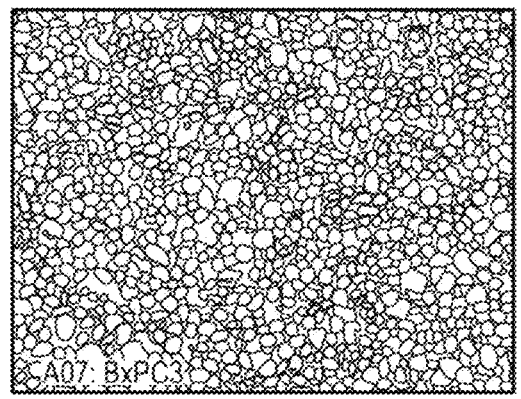

FIG. 16

|   | 1 | 2 | 3 | 4 | 5 | 6 | 7 | 8 | 9 | 10 | 11 | 12 |
|---|---|---|---|---|---|---|---|---|---|---|---|---|
| A | Adrenal gland[2] Normal 0/1+ | Adrenal gland[3] Normal 0/1+ | Adrenal gland[3] Normal 0/1+ | Bladder Normal 0/1+ | Bladder Normal 0/1+ | Bladder Normal 0/1+ | Bone marrow[5] Normal 0/1+ | Eye[4] Normal 0/1+ | Eye[4] Normal 0/1+ | Breast Normal 0/1+ | Breast Normal 0/1+ | Breast Normal 0/1+ |
| B | Cerebellum[4] Normal 0/1+ | Cerebellum[4] Normal 0/1+ | Cerebellum[4] Normal 0/1+ | Cerebral cortex[4] Normal 0/1+ | Cerebral cortex[4] Normal 0/1+ | Cerebral cortex[4] Normal 0/1+ | Fallopian tube Normal 0/1+ | Fallopian tube Normal 0/1+ | Fallopian tube Normal 0/1+ | GI-Esophagus Normal 2+ | GI-Esophagus Normal 2+ | GI-Esophagus Normal 2+ |
| C | GI-Stomach Normal 0/1+ | GI-Stomach Normal 0/1+ | GI-Stomach Normal 0/1+ | GI-Small intestine Normal 0/1+ | GI-Small intestine Normal 0/1+ | GI-Small intestine Normal 0/1+ | GI-Colon Normal 0/1+ | GI-Colon Normal 0/1+ | GI-Colon Normal 0/1+ | GI-Rectum Normal 0/1+ | GI-Rectum Normal 0/1+ | GI-Rectum Normal 0/1+ |
| D | Heart[4] Normal 0/1+ | Heart[4] Normal 0/1+ | Heart[4] Normal 0/1+ | Kidney Normal 0/1+ | Kidney Normal 0/1+ | Kidney Normal 0/1+ | Kidney Normal 0/1+ | Kidney Normal 0/1+ | Liver Normal 0/1+ | Liver Normal (cell swelling) 0/1+ | Liver Normal 0/1+ | |
| E | Lung Normal 2+ | Lung Normal 2+ | Lung Normal 2+ | Ovary Normal 0/1+ | Ovary Normal 0/1+ | Ovary Normal 0/1+ | Pancreas[3] Normal 0/1+ | Pancreas[3] Normal 0/1+ | Pancreas[3] Normal 0/1+ | Parathyroid Adenoma 0/1+ | Pituitary gland[5] Normal 0/1+ | Pituitary gland[4] Normal 0/1+ |
| F | Placenta Normal 0/1+ | Placenta Normal 0/1+ | Placenta Normal 0/1+ | Prostate Normal 0/1+ | Prostate Normal 0/1+ | Prostate Normal 0/1+ | Skin Normal 0/1+ | Skin Normal 0/1+ | Spinal cord[5] Normal 0/1+ | Spinal cord[5] Normal 0/1+ | Spleen Normal 2+ | Spleen Normal 2+ |
| G | Striated muscle[4] Normal 0/1+ | Striated muscle[4] Normal 0/1+ | Striated muscle[4] Normal 0/1+ | Testis Normal 0/1+ | Testis Normal 0/1+ | Testis Normal 2+ | Thymus[4] Normal 2+ | Thymus[4] Normal 2+ | Thymus[4] Normal 0/1+ | Thyroid Normal 0/1+ | Thyroid Normal 0/1+ | Thyroid Normal 0/1+ |
| H | Tonsil Normal 0/1+ | Tonsil Normal 0/1+ | Tonsil Normal 2+ | Ureter Normal 0/1+ | Ureter Normal 0/1+ | Ureter Normal 0/1- | Uterus-cervix Normal 0/1+ | Uterus-cervix Normal 0/1+ | Uterus-cervix Normal 0/1+ | Uterus-endometrium Normal 0/1+ | Uterus-endometrium Normal 0/1+ | Uterus-endometrium Normal 0/1+ |

ANTI-CEACAM6 ANTIBODIES AND METHODS OF USE

CROSS-REFERENCE TO RELATED APPLICATIONS

This patent application is a continuation of U.S. application Ser. No. 17/560,232, filed Dec. 22, 2021, which is a continuation of U.S. application Ser. No. 16/341,052, filed Apr. 10, 2019, which is a US National Phase Application under 35 U.S.C. § 371 of International Application No. PCT/SG2017/050509, filed Oct. 10, 2017, which claims the benefit of priority of Singapore application No. 10201608481W, filed 10 Oct. 2016, the contents of which were incorporated by reference in its entirety for all purposes.

INCORPORATION BY REFERENCE OF SEQUENCE LISTING PROVIDED ELECTRONICALLY

This patent application incorporates by reference the material (i.e., Sequence Listing) in the ASCII txt file named 105148P003C2_Sequence_Listing_txt created on Oct. 23, 2023 having a file size of 3,842 bytes. A substitute Sequence Listing is filed electronically herewith, the contents of which are incorporated by reference in their entirety. The electronic file was created on Jan. 23, 2024, is 12 kilobytes in size, and is titled 105148P003SEQ.xml.

FIELD OF THE INVENTION

The present invention relates generally to antibodies. Specifically, the invention relates to anti-CEACAM6 monoclonal antibodies and uses thereof.

BACKGROUND OF THE INVENTION

Carcinoembryonic antigen-related cell adhesion molecule 6 (CEACAM6) belongs to the carcinoembryonic antigen (CEA) family. CEACAM6 is a glycosyl phosphatidyl inositol (GPI) anchored cell surface glycoprotein that has been observed to be overexpressed in a variety of cancers including breast, pancreatic, colonic and non-small cell lung carcinoma. CEACAM6 acts as an oncogene in tumors and promotes cancer invasion, metastasis, anoikis resistance and chemoresistance, and inhibits differentiation.

To date, there are a very limited number of anti-CEACAM6 monoclonal antibodies that could be used for antibody therapy or as antibody-drug conjugates for cancer treatment. There is therefore a need to develop novel antibodies against CEACAM6 that can be used for antibody therapy or as antibody-drug conjugates for cancer treatment.

SUMMARY

In one aspect, there is provided an antigen-binding protein, or an antigen-binding fragment thereof, comprising (i) a heavy chain variable domain comprising a VHCDR1 having the amino acid sequence GNTFTSYVMH (SEQ ID NO: 3); a VHCDR2 having the amino acid sequence YINPYNDGTKYNEKFKG (SEQ ID NO: 4) and a VHCDR3 having the amino acid sequence STARATPYFYAMDY (SEQ ID NO: 5); and (ii) a light chain variable domain comprising a VLCDR1 having the amino acid sequence KSSQSLLWSVNQNSYLS (SEQ ID NO: 6), a VLCDR2 having the amino acid sequence GASIRES (SEQ ID NO: 7), and a VLCDR3 having the amino acid sequence QHNHGSFLPYT (SEQ ID NO: 8).

In another aspect, there is provided a composition comprising a physiologically acceptable carrier and a therapeutically effective amount of the antigen-binding protein, or an antigen-binding fragment thereof as disclosed herein.

In another aspect, there is provided a use of an antigen-binding protein, or an antigen-binding fragment thereof as disclosed herein, or composition as disclosed herein in the manufacture of a medicament for treating or preventing cancer.

In another aspect, there is provided an antigen-binding protein, or an antigen-binding fragment thereof as disclosed herein, or composition as disclosed herein for use in treating or preventing cancer.

In another aspect, there is provided a method of treating or preventing cancer comprising administering an antigen-binding protein, or an antigen-binding fragment thereof as disclosed herein, or composition as disclosed herein to a subject in need thereof.

In another aspect, there is provided a method for detecting cancer in a subject, the method comprising: contacting a sample obtained from the subject with an antigen-binding protein, or an antigen-binding fragment thereof as disclosed herein in vitro; detecting the binding of the antigen-binding protein, or an antigen-binding fragment thereof in the sample; correlating the binding with a level of binding in a control sample to determine the level of binding in the sample, wherein an increase in the level of binding in the sample relative to the control sample is indicative of cancer.

In another aspect, there is provided a method for identifying a subject susceptible to cancer the method comprising: contacting a sample obtained from the subject with an antigen-binding protein, or an antigen-binding fragment thereof as disclosed herein in vitro; detecting the binding of the antigen-binding protein, or an antigen-binding fragment thereof in the sample; correlating the binding with a level of binding in a control sample to determine the level of binding in the sample, wherein an increase in the level of binding in the sample relative to the control sample indicates that the subject is susceptible to cancer.

In one aspect, there is provided a kit when used in the method as disclosed herein, comprising an antigen-binding protein, or antigen-binding fragment thereof as disclosed herein, together with instructions for use.

DEFINITIONS

The following are some definitions that may be helpful in understanding the description of the present invention. These are intended as general definitions and should in no way limit the scope of the present invention to those terms alone, but are put forth for a better understanding of the following description.

The term "antigen binding protein" as used herein refers to antibodies, antibody fragments and other protein constructs, such as domains, which are capable of binding to CEACAM6.

The term "antibody" is used herein in the broadest sense to refer to molecules with an immunoglobulin-like domain and includes monoclonal, recombinant, polyclonal, chimeric, humanised, bispecific and heteroconjugate antibodies; a chimeric antigen receptor (CAR), a single variable domain, a domain antibody, antigen binding fragments, immunologically effective fragments, single chain Fv, diabodies, Tandabs™, etc (for a summary of alternative "antibody" formats see Holliger and Hudson, Nature Biotechnology, 2005, Vol 23, No. 9, 1126-1136).

The phrase "single variable domain" refers to an antigen binding protein variable domain (for example, $V_H$, $V_{HH}$, $V_L$) that specifically binds an antigen or epitope independently of a different variable region or domain.

A "domain antibody" or "dAb" may be considered the same as a "single variable domain" which is capable of binding to an antigen. A single variable domain may be a human antibody variable domain, but also includes single antibody variable domains from other species such as rodent (for example, as disclosed in WO 00/29004), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanised according to standard techniques available in the art, and such domains are considered to be "domain antibodies". As used herein $V_H$ includes camelid $V_{HH}$ domains.

As used herein the term "domain" refers to a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A domain can bind an antigen or epitope independently of a different variable region or domain.

An antigen binding fragment may be provided by means of arrangement of one or more CDRs on non-antibody protein scaffolds such as a domain. The domain may be a domain antibody or may be a domain which is a derivative of a scaffold selected from the group consisting of CTLA-4, lipocalin, SpA, an Affibody, an avimer, GroEl, transferrin, GroES and fibronectin/adnectin, which has been subjected to protein engineering in order to obtain binding to an antigen, such as CEACAM6, other than the natural ligand.

An antigen binding fragment or an immunologically effective fragment may comprise partial heavy or light chain variable sequences. Fragments are at least 5, 6, 8 or 10 amino acids in length. Alternatively the fragments are at least 15, at least 20, at least 50, at least 75, or at least 100 amino acids in length.

The term "specifically binds" as used throughout the present specification in relation to antigen binding proteins means that the antigen binding protein binds to CEACAM6 with no or insignificant binding to other (for example, unrelated) proteins. However, the term does not exclude the fact that the antigen binding proteins may also be cross-reactive with closely related molecules. The antigen binding proteins described herein may bind to CEACAM6 with at least 2, 5, 10, 50, 100, or 1000 fold greater affinity than they bind to closely related molecules.

The term "neutralises" as used throughout the present specification means that the biological activity of CEACAM6 is reduced in the presence of an antigen binding protein as described herein in comparison to the activity of CEACAM6 in the absence of the antigen binding protein, in vitro or in vivo. Neutralisation may be due to one or more of blocking CEACAM6 binding to its receptor, preventing CEACAM6 from activating its receptor, down regulating CEACAM6 or its receptor, or affecting effector functionality. The reduction or inhibition in biological activity may be partial or total. A neutralising antigen binding protein may neutralise the activity of CEACAM6 by at least 20%, 30% 40%, 50%, 55%, 60%, 65%, 70%, 75%, 80%, 82%, 84%, 86%, 88%, 90%, 92%, 94%, 95%, 96%, 97%, 98%, 99% or 100% relative to CEACAM6 activity in the absence of the antigen binding protein. Neutralisation may be determined or measured using one or more assays known to the skilled person or as described herein. For example, antigen binding protein binding to CEACAM6 can be assessed in a sandwich ELISA, by BIAcore™, FMAT, FORTEbio, or similar in vitro assays.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

As used herein, the term "promoter" is intended to refer to a region of DNA that initiates transcription of a particular gene.

As used herein, the term "cancerous" relates to being affected by or showing abnormalities characteristic of cancer.

As used herein, the term "biological sample" or "sample" is meant a sample of tissue or cells from a patient that has been obtained from, removed or isolated from the patient.

The term "obtained or derived from" as used herein is meant to be used inclusively. That is, it is intended to encompass any nucleotide sequence directly isolated from a biological sample or any nucleotide sequence derived from the sample.

The method as described herein is suitable for use in a sample of fresh tissue, frozen tissue, paraffin-preserved tissue and/or ethanol preserved tissue. The sample may be a biological sample. Non-limiting examples of biological samples include whole blood or a component thereof (e.g. plasma, serum), urine, saliva lymph, bile fluid, sputum, tears, cerebrospinal fluid, bronchioalveolar lavage fluid, synovial fluid, semen, ascitic tumour fluid, breast milk and pus. In one embodiment, the sample of nucleic acid is obtained from blood, amniotic fluid or a buccal smear. In a preferred embodiment, the sample is a whole blood sample.

A biological sample as contemplated herein includes cultured biological materials, including a sample derived from cultured cells, such as culture medium collected from cultured cells or a cell pellet. Accordingly, a biological sample may refer to a lysate, homogenate or extract prepared from a whole organism or a subset of its tissues, cells or component parts, or a fraction or portion thereof. A biological sample may also be modified prior to use, for example, by purification of one or more components, dilution, and/or centrifugation.

As used herein, the term "detectable label" or "reporter" refers to a detectable marker or reporter molecules, which can be attached to nucleic acids. Typical labels include fluorophores, radioactive isotopes, ligands, chemiluminescent agents, metal sols and colloids, and enzymes. Methods for labeling and guidance in the choice of labels useful for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, Greene Publishing Associates and Wiley-Intersciences (1987).

As used herein, the term "susceptible to cancer" or "susceptibility to cancer" refers to the likelihood of a subject developing cancer. The term does not indicate that a subject will develop cancer with 100% certainty. Rather, the term "susceptible to cancer" refers to an increased probability that a subject will develop cancer when compared to an individual who is not "susceptible to cancer".

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

Unless the context requires otherwise or specifically stated to the contrary, integers, steps, or elements of the invention recited herein as singular integers, steps or elements clearly encompass both singular and plural forms of the recited integers, steps or elements.

The word "substantially" does not exclude "completely" e.g. a composition which is "substantially free" from Y may be completely free from Y. Where necessary, the word "substantially" may be omitted from the definition of the invention.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

BRIEF DESCRIPTION OF THE DRAWINGS

The invention will be better understood with reference to the detailed description when considered in conjunction with the non-limiting examples and the accompanying drawings, in which:

FIGS. 3A-3F show flow cytometry screening with A) PC-9 and derived gefitinib-resistant clones, B) NSCLC lines, C) HCC827 and derived gefitinib-resistant clones, D) breast cancer lines, E) colorectal cancer lines, and F) normal cell lines.

FIGS. 4A-4E show the characterization of GR 6A04 monoclonal antibody and its derivatives. A) GR 6A04 is of mouse IgG1, κ isotype. B) Variable heavy and light chain translated sequences with the CDR underlined. C) Direct conjugation of GR6A04 and an IgG1 isotype control (MG1.45) to Monomethyl auristatin E (MMAE) to obtain GR6A04-MMAE and MG1.45 respectively (DAR:Drug-antibody ratio). Flow cytometry binding is not affected after conjugation. D) Human chimeric monoclonal antibody for GR 6A04 (Hu-GR6A04). $V_H$ and $V_L$ sequences were cloned into expression vector with human constant region backbone. Hu-GR6A04 cloned into CHO cells for expression. Coomassie staining showed expected protein size and flow cytometry binding was comparable to GR6A04.

FIGS. 6A-6B show A) immunoprecipitation with GR 6A04. Boxed area was excised for mass spectrometry. B) Mass spectrometry analysis of excised region identified the top 5 putative antigens after removal of non-specific hits found in the same region in the Column Control lane. The results showed that putative antigens are arranged based on the overall score, which is a function of the total protein coverage, and number of unique peptides found. The antigen identity was then validated by a pull-down with commercial antibodies against the target, and a cross-probe of the immunoprecipitated products with GR 6A04, and vice-versa. GRP78 was tested by cross-IP and ruled out as possible antigen for GR 6A04.

FIGS. 8A-8B show immunohistology of GR 6A04 in cancer cell lines. A) FFPE on PC-9 cell pellets show both membrane bound and cytosolic localisation of GR 6A04. B) FFPE cell line array screening scored by ImmunoMembrane across duplicate cores.

FIG. 9 shows immunohistology of GR 6A04 on tumour tissue. FFPE on tissue samples (Pantomics TMAs) using a mix of normal and tumour tissues, multiple organs (MNT241) and scored by ImmunoMembrane.

FIG. 10 shows immunohistology of GR 6A04 on tumour tissue. FFPE on tumour tissues, multiple organs (MTU481).

FIGS. 11A-11C show immunohistology of GR 6A04 on tumour tissue. A) FFPE on tumour tissue, multiple organs (MTU951) and a summary of the cores stained. B) 2+ staining on two normal cores; esophageal and lung (false positive score). C) Representative positive scoring on cancers in multiple organs.

FIG. 12 shows immunohistology of GR 6A04 on NSCLC tissue samples. Staining on lung tumour TMA with adjacent normal (LC 1001 2a) shows positive staining for 4/27 squamous and 9/18 adenocarcinoma, negative staining for paired adjacent normal tissue.

FIG. 13 shows core images from the array LC1001 2a.

FIGS. 15A-15D show the comparison of GR 6A04 with a commercially available anti-CEACAM6 antibody. A) GR6A04 affected by Tunicamycin (N-glycosylation inhibitor) and PNGase digestion, but not commercial anti-CEACAM6 (Clone 9A6). B) Differences in role of glycosylation in mAb binding also leads to differences in specificity in immunohistochemistry. Cell line array with 1 additional core scored positive (boxed).

DETAILED DESCRIPTION OF THE PRESENT INVENTION

Figure 1:
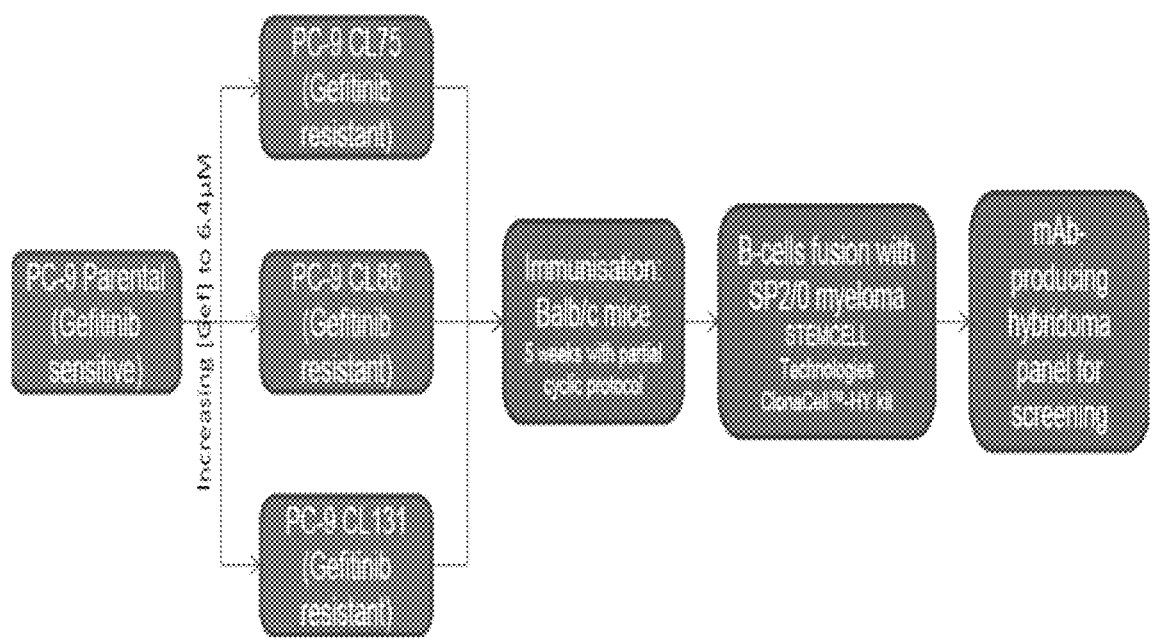
FIG. 1 is a flow diagram depicting the methodology for generating Gefitinib resistant clones from PC-9 and cell lines used for immunization and hybridoma fusion of generation of monoclonal antibody panel.

In a first aspect, there is provided an antigen-binding protein, or an antigen-binding fragment thereof, comprising (i) a heavy chain variable domain comprising a VHCDR1 having the amino acid sequence GNTFTSYVMH (SEQ ID NO: 3); a VHCDR2 having the amino acid sequence YINPYNDGTKYNEKFKG (SEQ ID NO: 4) and a VHCDR3 having the amino acid sequence STARATPYFYAMDY (SEQ ID NO: 5); and (ii) a light chain variable domain comprising a VLCDR1 having the amino acid sequence KSSQSLLWSVNQNSYLS (SEQ ID NO: 6), a VLCDR2 having the amino acid sequence GASIRES (SEQ ID NO: 7), and a VLCDR3 having the amino acid sequence QHNHGSFLPYT (SEQ ID NO: 8).

The antigen-binding protein, or antigen-binding fragment thereof, may comprise heavy and light chain CDR regions that are about 80%, about 85%, about 90%, about 95%, about 96%, about 97%, about 98% or about 99% identical to the heavy and light chain CDR regions of (i) and (ii).

In one embodiment, the heavy chain variable region comprises the amino acid sequence SGPELVKP-GASVKMSCKASGNTFTSYVMHWVKQKPGQGLEWI-GYINPYNDGTKYN EKFKGKATLTSDKSSSTAY-MELSSLTSEDSAVYYCARSTARATPYFYAMDYWG-QGT SVTVSS as set forth in SEQ ID NO:1. Alternatively, the heavy chain variable region may comprise an amino acid sequence having about 80%, about 85%, about 90%, about 95%, about 96%, about 97%, about 98% or about 99% identity to the amino acid sequence set forth in SEQ ID NO:1.

In one embodiment, the light chain variable region comprises the amino acid sequence

DILMTQSPSSLAVTAGEKVTMRCKSSQSLLWSVNQNSYLSWYQLKQGQPP

KLLLYGASIRESWVPDRFTGSGSGTDFTLTISNVHVEDLAVYYCQHNHGS

FLPYTFGGGTKLEI

K as set forth in SEQ ID NO:2. Alternatively, the antigen-binding protein, or antigen-binding fragment thereof, may comprise a light chain variable region which comprises an amino acid sequence having about 80%, about 85%, about 90%, about 95%, about 96%, about 97%, about 98% or about 99% identity to the amino acid sequence set forth in SEQ ID NO:2.

In one embodiment, the antigen-binding protein, or antigen-binding fragment thereof, as claimed in any one of claims 1 to 6, wherein the antigen binding protein is selected from the group consisting of monoclonal, recombinant, polyclonal, chimeric, humanised, bispecific and heteroconjugate antibodies; a chimeric antigen receptor (CAR), a single variable domain, a domain antibody, antigen binding fragments, immunologically effective fragments, single chain Fv, a single chain antibody, a univalent antibody lacking a hinge region, a minibody, diabodies, and Tandabs™

In one embodiment, the antigen-binding protein, or antigen-binding fragment thereof may be a monoclonal antibody. The monoclonal antibody may be GR 6A04. In one embodiment, the monoclonal antibody may be humanised. Alternatively, the monoclonal antibody may be chimeric.

In one embodiment, the antigen-binding protein, or antigen-binding fragment thereof may bind to CEACAM6. In one embodiment, the antigen-binding protein, or antigen-binding fragment thereof may bind to a glycan on CEACAM6. The antigen-binding protein, or antigen-binding fragment thereof as described herein may bind to an N-linked glycan on CEACAM6.

In another embodiment, the antigen-binding protein, or antigen-binding fragment thereof as described herein may comprise a radioisotope or a cytotoxin conjugated thereto. The antigen-binding protein, or antigen-binding fragment thereof may be conjugated with a cytotoxin selected from the group consisting of monomethyl auristatin E (MMAE), mertansine (DM-1), saporin, gemcitabine, irinotecan, etoposide, vinblastine, pemetrexed, docetaxel, paclitaxel, platinum agents (for example, cisplatin, oxaliplatin and carboplatin), vinorelbine, capecitabine, mitoxantrone, ixabepilone, eribulin, 5-fluorouracil, trifluridine and tipiracil.

In one embodiment, the antigen-binding protein, or an antigen-binding fragment as described herein may be internalized into a cell upon binding to CEACAM6.

In another embodiment, the antigen-binding protein, or an antigen-binding fragment as described herein may not be internalized into a cell upon binding to CEACAM6.

In one embodiment, the antigen-binding protein, or an antigen-binding fragment as described herein may selectively bind to a gefitinib resistant lung cancer cell, a non-small cell lung cancer cell, a breast cancer cell and/or a colorectal cancer cell.

In another aspect, there is provided a composition comprising a physiologically acceptable carrier and a therapeutically effective amount of the antigen-binding protein, or an antigen-binding fragment thereof as described herein. In one embodiment, the composition as disclosed herein may comprise one or more further therapeutic compounds.

The percentage of the the antigen-binding protein, or an antigen-binding fragment thereof, as described herein, in pharmaceutical compositions and preparations may, of course, be varied and, for example, may conveniently range from about 2% to about 90%, about 5% to about 80%, about 10% to about 75%, about 15% to about 65%; about 20% to about 60%, about 25% to about 50%, about 30% to about 45%, or about 35% to about 45%, of the weight of the dosage unit. The amount of compound in therapeutically useful compositions is such that a suitable dosage will be obtained.

The language "physiologically acceptable carrier" is intended to include solvents, dispersion media, coatings, anti-bacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated. Supplementary active compounds may also be incorporated into the compositions according to the present invention. It is especially advantageous to formulate parenteral compositions in dosage unit form for ease of administration and uniformity of dosage.

"Dosage unit form" as used herein refers to physically discrete units suited as unitary dosages for the individual to be treated; each unit containing a predetermined quantity of compound(s) is calculated to produce the desired therapeutic effect in association with the required pharmaceutical carrier. The compound(s) may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

The composition may be conveniently administered by injection, for example, subcutaneous, intravenous, and the like. The composition may also be administered parenterally or intraperitoneally. In one embodiment, the compound may be administered by injection. In the case of injectable solutions, the carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by including various anti-bacterial and/or anti-fungal agents. Suitable agents are well known to those skilled in the art and include, for example, parabens, chlorobutanol, phenol, benzyl alcohol, ascorbic acid, thimerosal, and the like. In many cases, it may be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminium monostearate and gelatin.

Sterile injectable solutions can be prepared by incorporating the analogue in the required amount in an appropriate solvent with one or a combination of ingredients enumerated above, as required, followed by filtered sterilisation. Generally, dispersions are prepared by incorporating the analogue into a sterile vehicle which contains a basic dispersion medium and the required other ingredients from those enumerated above.

Under ordinary conditions of storage and use, pharmaceutical preparations may contain a preservative to prevent the growth of microorganisms. Preferably, the pharmaceutical composition may further include a suitable buffer to minimise acid hydrolysis. Suitable buffer agent agents are well known to those skilled in the art and include, but are not limited to, phosphates, citrates, carbonates and mixtures thereof.

Single or multiple administrations of the pharmaceutical compositions according to the invention may be carried out. One skilled in the art would be able, by routine experimentation, to determine effective, non-toxic dosage levels of the compound and/or composition of the invention and an administration pattern which would be suitable for treating the diseases and/or infections to which the compounds and compositions are applicable.

Further, it will be apparent to one of ordinary skill in the art that the optimal course of treatment, such as the number of doses of the compound or composition of the invention given per day for a defined number of days, can be ascertained using convention course of treatment determination tests.

Generally, an effective dosage per 24 hours may be in the range of about 0.0001 mg to about 1000 mg per kg body weight; suitably, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight.

Alternatively, an effective dosage may be up to about 500 mg/m$^2$. For example, generally, an effective dosage is expected to be in the range of about 25 to about 500 mg/m$^2$, about 25 to about 350 mg/m$^2$, about 25 to about 300 mg/m$^2$, about 25 to about 250 mg/m$^2$, about 50 to about 250 mg/m$^2$, and about 75 to about 150 mg/m$^2$.

In another aspect, there is provided use of an antigen-binding protein, or an antigen-binding fragment thereof as disclosed herein, or the composition as disclosed herein in the manufacture of a medicament for treating or preventing cancer.

In one embodiment, the cancer may be selected from the group consisting of gefitinib resistant lung cancer, non-small cell lung cancer, breast cancer, stomach cancer, small intestine cancer, esophageal cancer and colorectal cancer.

In some embodiments, the medicament may be administered with one or more further active pharmaceutical ingredients. Alternatively, the medicament may be administered with chemotherapy. The further active pharmaceutical ingredients or chemotherapy may be administered separately, simultaneously or sequentially.

In another aspect, there is provided a method for detecting cancer in a subject, the method comprising: contacting a sample obtained from the subject with an antigen-binding protein, or an antigen-binding fragment thereof as disclosed herein in vitro; detecting the binding of the antigen-binding protein, or an antigen-binding fragment thereof in the sample; correlating the binding with a level of binding in a control sample to determine the level of binding in the sample, wherein an increase in the level of binding in the sample relative to the control sample is indicative of cancer.

In another aspect, there is provided a method for identifying a subject susceptible to cancer the method comprising: contacting a sample obtained from the subject with an antigen-binding protein, or an antigen-binding fragment thereof as disclosed herein in vitro; detecting the binding of the antigen-binding protein, or an antigen-binding fragment thereof in the sample; correlating the binding with a level of binding in a control sample to determine the level of binding in the sample, wherein an increase in the level of binding in the sample relative to the control sample indicates that the subject is susceptible to cancer.

In one embodiment, the control sample is from the same subject. Alternatively, the control sample may be from a different subject.

In one embodiment, the antigen-binding protein, or antigen-binding fragment thereof as described herein may comprise a detectable label. The detectable label may be selected from the group consisting of a fluorescent label, a chemiluminescent label, an enzymatic label and a radionuclide label.

In one embodiment, the detectable label may be selected from the group consisting of biotin, alkaline phosphatase, horseradish peroxidase, FITC, PE and Cy Dyes. The detectable label may be detected in an assay selected from flow cytometry, tissue section, immunofluorescence, immunocytochemistry or immunohistochemistry.

In one aspect, there is provided a kit when used in the method as described herein, comprising an antigen-binding protein, or antigen-binding fragment thereof as described herein, together with instructions for use.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXAMPLES

Non-limiting examples of the invention and comparative examples will be further described in greater detail by reference to specific Examples, which should not be construed as in any way limiting the scope of the invention.

Materials and Methods
Culture and Generation of Gefitinib Resistant Cell Lines

PC-9 were cultured in RPMI (Invitrogen, USA) supplemented with 10% foetal bovine serum (HyClone GE Healthscience, South America). To obtain PC-9 clones with acquired gefitinib resistance, PC-9 cultures were exposed to increasing concentration of gefitinib (Selleckchem, USA), starting from 2 nM and gradually increased with each subsequent passage to a final concentration of 6.4 μM. GR clones, CL75, CL86 and CL131, were maintained in 6.4 μM gefitinib thereafter.

A549 were cultured in DMEM (Invitrogen, USA) supplemented with 10% FBS and 20 mM L-glutamine (Invitrogen, USA). A549 has primary resistance to gefitinib, with IC50 of >10 μM.

Generation of GR mAb Panel

Immunisation of PC-9 GR lines, CL75, CL86 and CL131, was done with 5E6 cells resuspended 1:1 with Fraund's complete adjuvant. Immunisation was done once per week for the first immunisation in week 1-3 with only a single line each, and a mixed suspension of all three lines for the subsequent immunisations in week 4-5. After 5 weeks, mice were sacrificed, and the B-cells collected for fusion with Sp2/0 mouse myeloma lines using STEMCELL Technologies ClonaCell™-HY kit as per manufacturer's instructions. Single hybridoma clones were picked into 96-wells, and the culture supernatant collected for screening by flow cytometry.

Flow Cytometry

Cells were harvested as single cell suspensions using trypsin. 1E5 cells were used per sample, and incubated with 100 μl of mAb culture supernatant for 30 min. Cells were then washed with 1% bovine serum albumin in PBS, and further incubated with 100 μl of goat anti-mouse antibody fluorescein isothiocyanate (FITC)-conjugated (1:500, DAKO, Denmark) for 15 min at 4° C. in the dark. Cells were again washed and resuspended in 200 μL of 1% BSA/PBS for analysis on Guava® easy Cyte 8HT Benchtop Flow Cytometer (Merck Millipore, USA). For interrogation of intercellular binding, cells were fixed with 4% PFA/PBS (Affymetrix, USA) at room temperature for 10 min, washed in PBS, and permeabilised with 0.1% triton/PBS for 5 min at room temperature, before proceeding with incubation with mAb supernatant/primary antibody. For staining with propidium iodide, PI was added to a final concentration of 5 μg/mL for 5 min just prior to analysis by the flow cytometer.

Western Blot and Immunoprecipitation

Membrane proteins were extracted from PC-9 cell pellets using the Membrane Protein Extraction Kit (BioVision, USA). Briefly, cell pellets of 5E7 cells were resuspended in 1 mL of Homogenize Buffer and cell membranes broken in a dounce homogenizer. This was transferred into an Eppendorf tube and centrifuged at 700×g for 10 min at 4° C. to remove cell debris. The supernatant was transferred to a new Eppendorf tube and centrifuged at 12,000×g for 30 min at 4° C. to pellet the membrane. The membrane was finally resuspended in 500 μl of 1×Cell Lysis Buffer (Cell Signaling Technology, USA) containing protease inhibitors (Pierce ThermoScientific, USA). The membrane protein solution was clarified with by centrifugation at 15,000×g for 5 min at 4° C., to remove any insoluble proteins. Protein was quantified using the Pierce 660 nM Protein Assay Reagent.

Immunoprecipitation (IP) was conducted using the automated Phynexus MEA system (Phynexus Inc., USA). GR6A04 was captured onto Protein G PhyTip columns containing 5 μl of resin bed. The column was then washed with PBS to remove unbound proteins, and PC-9 membrane protein extract was introduced to bind to GR6A04 that has been captured on the column. The column was then washed with Wash Buffer II (140 mM NaCl, pH 7.4) before elution at low pH with Elution Buffer (200 mM NaH2PO4/140 mM NaCl pH 2.5) and neutralized immediately with 1 M Tris-Cl pH 9.0. The IP product is then subjected to analysis by Western blot.

PC-9 membrane protein extracts, or IP products were denatured by in protein loading dye containing SDS at a final concentration of 1%, and heated at 95° C. for 5 min. The sample was then loaded into pre-cast gradient gel (NuPAGE 4-12% gradient gel, Invitrogen), and separated by SDS-PAGE running MOPS Running Buffer (NuPAGE Invitrogen, USA). After gel electrophoresis, the resolved proteins were transferred onto a polyvinylidene fluoride (PVDF) membrane (BioRad, USA) in a transfer buffer containing 20% methanol, 10% Tris-Glycine in DI water at constant voltage of 110V for 90 min.

The membrane was then blocked with 5% milk prepared in PBS/0.1% Tween-20 (PBS-T) for 30 min at room temperature. The membrane was then washed in PBS-T, followed by overnight incubation of GR6A04 at 2 μg/mL in 2.5% milk at 4° C. Subsequently, the membrane was washed in PBS-T, before incubation with goat anti-mouse secondary antibodies horseradish peroxidase-conjugated (1:10000, Dako) for 1 hour at room temperature. After a final wash with PBS-T, the binding of HRP-conjugated secondary antibodies were visualized by ECL detection (GE Healthcare, Sweden).

Coomassie Blue Staining and Mass-Spectrometry

A parallel gel was run for the IP products, which was stained with Coomassie blue staining solution containing 0.1% Coomassie Blue R250 in 10% acetic acid, 50% methanol and 40% water for 1 hour at room temperature. The staining solution is then removed, and replaced by the de-staining solution containing 10% acetic acid, 50% methanol and 40% water. The de-staining solution is replaced with fresh solution, until the background of the gel is almost clear.

The de-stained gel is then re-hydrated in water. The gel is then compared with the Western blot of the IP products to determine the position of the antigen band on the gel. This region is then excised for LC-MS analysis.

Glycosylation Studies

PNGase digestion was carried out according to manufacturer's protocol (New England Biolabs). Briefly, 20 μg of PC-9 membrane protein extract was first denatured in 1×glycoprotein Denaturing Buffer at 95° C. for 10 minutes. Subsequently, 1×G7 Reaction Buffer and 10% NP-40 were added and incubated with PNGase F at 37° C. for 1 hour. Digested proteins were subsequently analysed by Western blotting as described above.

Inhibition of N-glycosylation of proteins during cell culture was also achieved by addition of 1 μM Tunicamycin (Sigma Aldrich, USA) in the culture media. PC-9 cells were seeded at 1E5 cells in a 6-well tissue culture place, and grown in culture media spiked with Tunicamycin, or DMSO for 3 days until confluent. The cells were then harvested for analysis by flow cytometry and Western blotting.

Immunohistochemistry Staining

TMA slides containing FFPE tissues were first heated in an oven at 60° C. for 30 min to remove any solvents. The slides were then dewaxed and re-hydrated through sequential immersion in Histoclear (2×), 100% ethanol (2×), 95% ethanol, 70% ethanol, and finally in DI water.

Heat-induced epitope retrieval was done in a solution containing 10 mM Tris Base, 1 mM EDTA, 0.05% Tween 20 at pH 9.0, and heated at 95° C. for 20 min. The container with the antigen retrieval solution and slides was then removed and allowed to cool to room temperature for an additional 20 min. The slides were then washed in DI water. Endogenous peroxidase activity was then blocked by incubation of the slides with 3% $H_2O_2$ in PBS for 30 min at room temperature. The slides were washed in DI water, followed by a blocking step with 10% normal goat serum in PBS for 30 min.

The slides were then incubated with GR6A04 at 5 μg/mL in blocking solution overnight at 4° C. The slides were then washed an incubated with a polymer-based anti-mouse secondary antibody conjugated with HRP (DAKO, USA) for 30 min at room temperature, and developed with the recommended DAB chromogen substrate solution for 2 min, and counterstained with Gill's Hematoxylin solution.

The stained slides were subsequently dehydrated through immersion in 50% ethanol, 70% ethanol, 90% ethanol, 100% ethanol (2×) and Histoclear (2×), before mounting with a glass cover slip. The slides were then imaged with the Zeiss AxioScan Digital Slide Scanner.

Enrichment of GR6A04 Binding Population from A549 Cell Line

The CELLection™ Pan Mouse IgG Kit (ThermoScientific, USA) was used for the enrichment of GR6A04− and GR6A04+ sub-populations from the A549 parental lung adenocarcinoma line, according to manufacturer's instructions. Briefly, A549 cells were harvested with trypsin to obtain a single-cell solution. Cells were incubated with GR6A04 at 10 μg/1E7 cells for 30 min at 4° C. The cells were then centrifuged at 300×g for 3 min to remove unbound GR6A04, before incubating it with the Dynabeads following kit recommendations. The cell-bead suspension was then applied on the magnetic rack, and allowed to separate. The supernatant was collected as the GR6A04− population, while the bound beads and cells were collected as the GR6A04+ population. Both fractions were washed and subjected to the magnetic rack 3 times. The bound beads and cells were finally incubated with DNase I to release the cells from the Dynabeads. Cells were seeded into T75 tissue culture flasks at a density of 2.5E6 cells per flask.

Antibody-Dependent Cell-Mediated Cytotoxicity (ADCC) Assay

ADCC activity was measured using a reporter bioassay (Promega; ADCC Reporter Bioassay, #G7010). The ADCC bioassay was carried out according to the manufacturer's protocol Briefly, PC-9 and A549 cells were seeded at 5,000 cells per well in a 96-well clear bottom black tissue culture plates (Corning; #3904) in low 4% IgG-serum (Promega; #G711A) media and allowed to attach and spread overnight. Serial dilutions of Hu-GR6A04 were incubated in triplicate wells for approximately 15 min at 37° C., 5% CO2. Following incubation, engineered effector cells were added to the wells at approximately 150,000 cells per well. After 6 hours, Bio-Glo™ Luciferase Assay Substrate (Promega; #G719A and #G720A) was added to the wells and luminescence was measured using the Infinite® 200 microplate reader (Tecan).

Proliferation-CellTiter-Glo Luminescent Cell Viability (CTG) Assay

Cells were seeded into a black coated 96 well plate (Grenier Bio-one, UK) at a range of density from 1000-5000 cells per well (depending on the cell type used) and 90 μL per well. The plate was then incubated for 24 hours at 37° C. in humidified air with 5% $CO_2$. After 24 hours, 10 μL of mAb or buffer was added to each well and the plate was again placed at 37° C. in humidified air with 5% $CO_2$ 4 days after addition of mAb or buffer, 100 μL of CTG substrate (Promega, Wisconsin, USA) was added to each well. The plate was then left in the dark for 10 minutes, with vigorous shaking. The cell viability of the samples was then quantified using Tecan I-control (Tecan, Switzerland).

Antibody Drug Conjugates (ADCs)

GR6A04 and a commercial mouse IgG1 isotype antibody (Clone MG1.45 from BioLegend) were directly conjugated with MMAE toxin (Moradec, San Diego, USA) at a DAR of 3.0 and 3.3 respectively. Dose-response curve for the conjugated mAbs were established with the CTG assay with a serial dilution range of 0 to 4.5 μg/ml. The cell viability of the cells was measure 4 days post treatment as described previously.

In Vivo Xenograft Model

Xenograft models were established using A549− GR6A04+ cells in NCr Nude mice. 5E6 cells in DMEM basal media were mixed at a 1:1 ratio with Matrigel, and injected subcutaneously at a volume of 200 μl. Tumours were allowed to form and reach a size of >150 $mm^3$, before they were randomised into 5 groups of 5 mice each. The groups were treated with mAbs as follows: (1) Buffer control; (2) GR6A04-MMAE; (3) Hu-GR6A04; (4) GR6A04; (5) MG1.45-MMAE isotype control. mAbs were injected via tail vein injection at a total volume of 100 μl. Each dose, were applicable, is at 200 μg (equivalent to 10 mg/kg), and treatment was done every 4 days, for a total of 3 doses (Day 0, 4 and 8). Tumour size was monitored over 50 days.

Results and Discussion

Generation of GR Resistant mAb Panel

GR6A04 was identified as part of a monoclonal antibody (mAb) panel generated against PC-9 lung adenocarcinoma with acquired resistance against Gefitinib, a small molecule inhibitor of epidermal growth factor (EGFR). Gefitinib resistant (GR) PC-9 clones were generated through culture in increasing concentration of Gefitinib until a stable line was obtained at a Gefitinib concentration of 6.4 μM. This was used as a surrogate for acquired resistance against Gefitinib observed in lung cancer patients undergoing treatment with the compound.

Three Gefitinib resistant PC-9 clones (CL75, CL86 and CL131) were used for immunisation in Balb/c mice in a semi-cyclic protocol (FIG. 1). The mice were sacrificed in Week 6, and the B-cells fused with Sp2/0 mouse myeloma cells using STEMCELL Technologies ClonaCell™-HY kit, and mAb-producing hybridoma clones were obtained. The mAbs from this GR panel was screened for binding to the immunising lines by flow cytometry, of which GR6A04 was identified as one of the binding lead candidates from this panel.

GR6A04 Binding on Cell Lines by Flow Cytometry

Figure 2A:
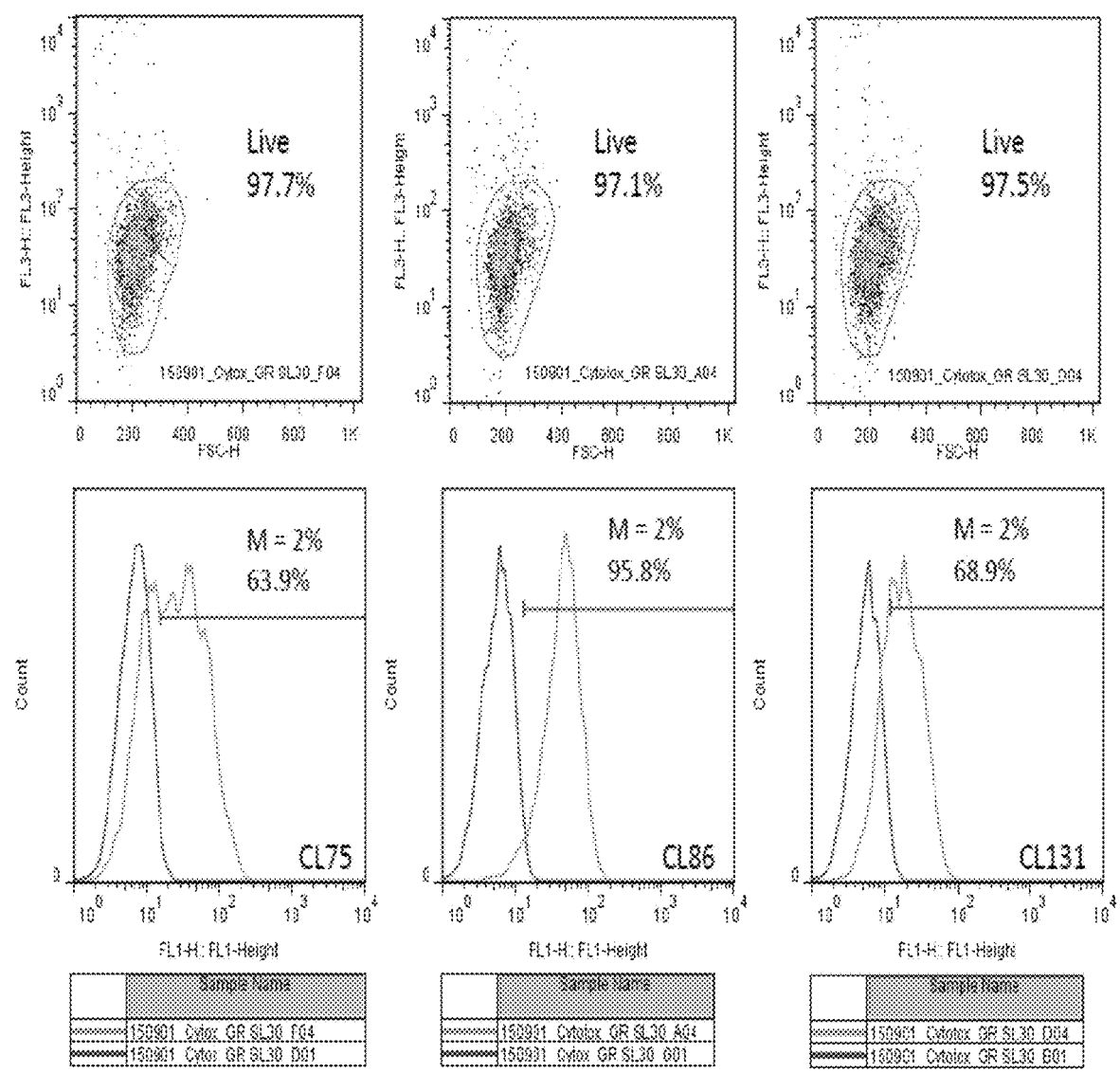
FIGS. 2A-2B show flow cytometry binding of GR6A04 on A) immunizing GR lines, CL75, CL86 and CL131, and B) parental PC-9 and another GR PC-9 line. Gating was performed at M=2% of negative control for each cell line. Absence of propidium iodide staining (FL-3) shows no inherent cytotoxicity from mAb GR 6A04 binding.
Figure 2B:
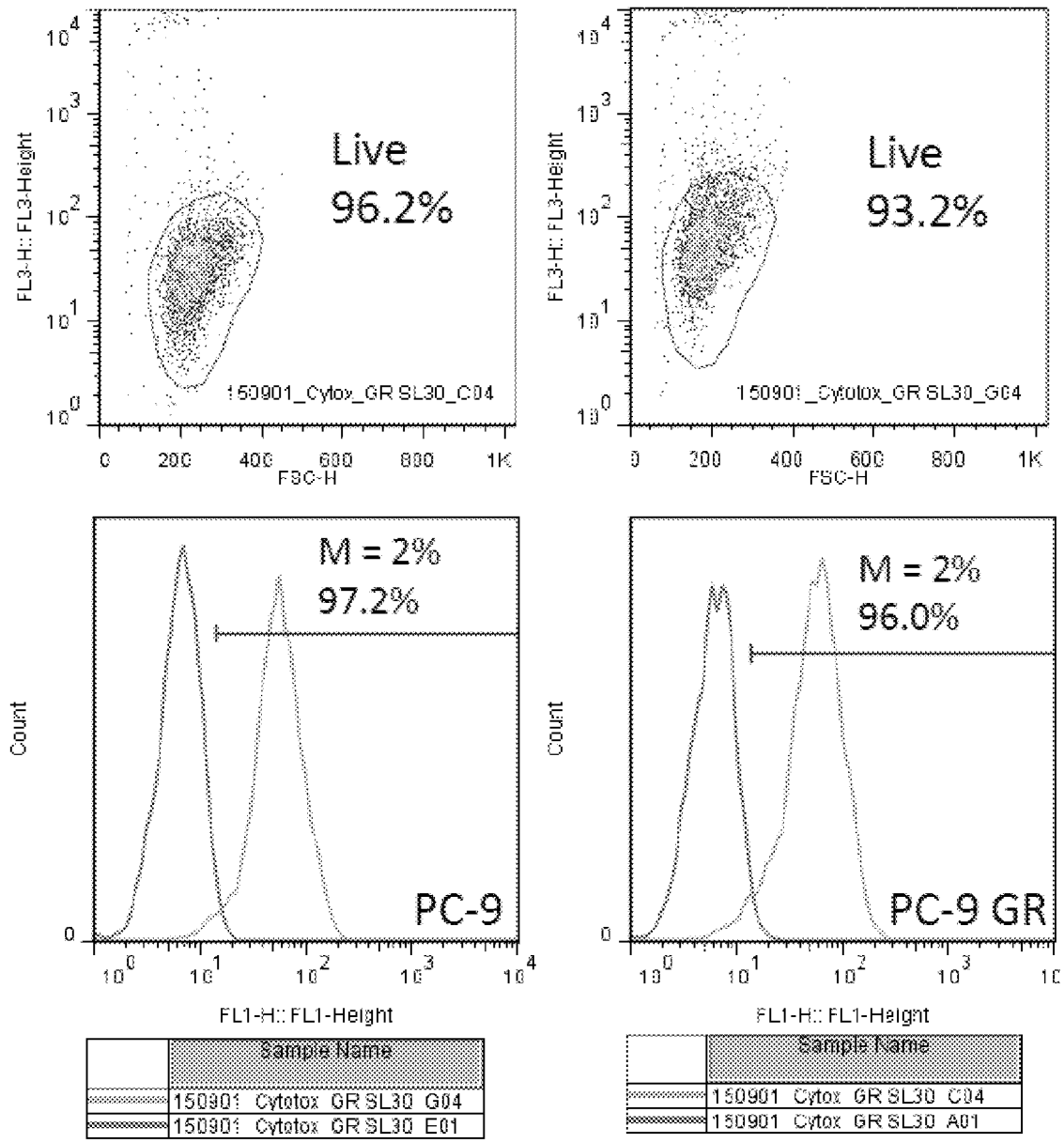

GR6A04 demonstrated strong reactivity (>50%) towards the three PC-9 Gefitinib resistant clones used for immunisation, with percentage positive-binding determined from FL-1 channel gated at 2% on the secondary-only control (FIGS. 2A-B). Propidium iodide staining on the FL-3 channel also showed no apparent cell cytotoxicity when cells were incubated with the mAb alone. GR6A04 binding was also tested on the Gefitinib sensitive parental PC-9 cell line, and on another GR PC-9 clone not used in the immunisation, with similarly high binding for both lines. This flow cytometry binding data is summarised in FIG. 3A.

Flow cytometry binding of GR6A04 was also tested in other NSCLC lines, with partial binding on 2 of 4 lines tested (A549 and Calu-3). GR clones from another lung adenocarcinoma line, HCC827, were also obtained by culturing in increasing Gefitinib concentrations. GR6A04 binding was observed for 2 of 6 of these GR HCC827 clones. In addition, binding on other cancer indications also showed GR6A04 reactivity in 3 of 13 breast cancer lines and 1 of 2 colorectal cancer lines tested. GR6A04 binding on the different cancer indications is summarised in FIG. 3B-E.

Importantly, using the same staining method, binding of GR6A04 on the cell surface of normal cells was found to be negligible (<8%) when tested with various normal cell lines including fibroblasts, endothelial and epithelial cells, and primary peripheral blood mononuclear cells (PBMCs), as summarised in FIG. 3F.

In summary, the flow cytometry binding characteristics of GR6A04 are a) GR6A04 binds to the cell surface of PC-9 and their derived gefitinib-resistant clones based on flow cytometry, b) GR6A04 demonstrates reactivity to other NSCLC, breast and colorectal cancer lines and c) there is no cross-reactivity to normal cell lines tested.

Characterisation of GR6A04 mAb and Derivatives

Figure 4A:
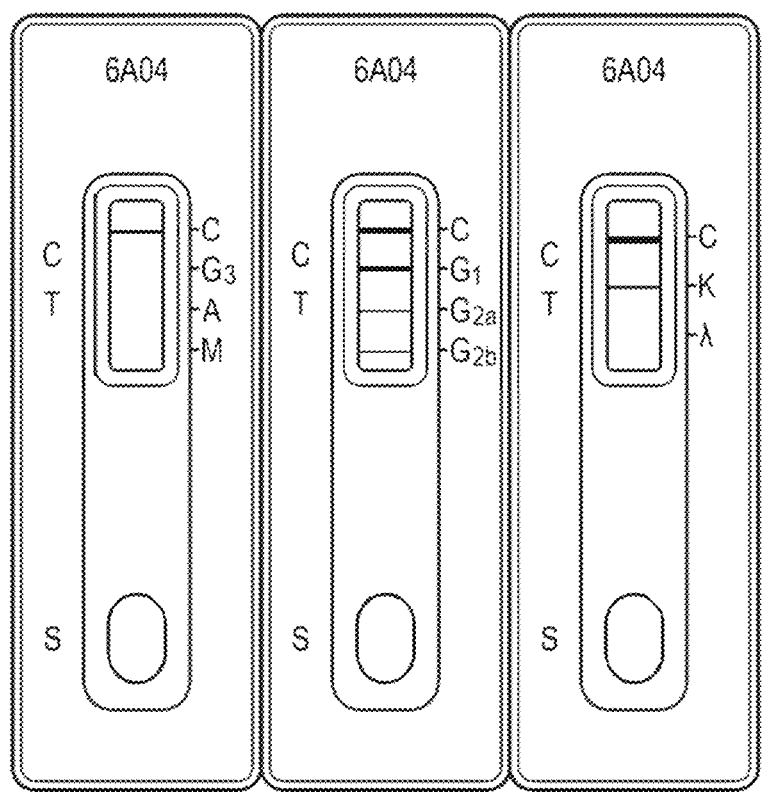

The isotype of GR6A04 mAb was determined to be of a mouse IgG1 subtype, as determined by Pierce™ Rapid Antibody Isotyping Kit in FIG. 4A. The variable heavy chain ($V_H$) and light chain ($V_L$) amino acid sequences were determined as FIG. 4B by use of degenerate primers for mouse immunoglobulins. GR6A04 was purified from hybridoma culture supernatant using CaptureSelect™ IgG-Fc (ms) Affinity Matrix with the ÄKTA avant system.

Two derivatives of GR6A04 was made and characterised: an antibody drug conjugate with monomethyl auristatin E (MMAE) (GR6A04-MMAE), and a human chimeric mAb with the $V_H$ and $V_L$ cloned into a human Ig constant region backbone (Hu-GR6A04).

Figure 4C:
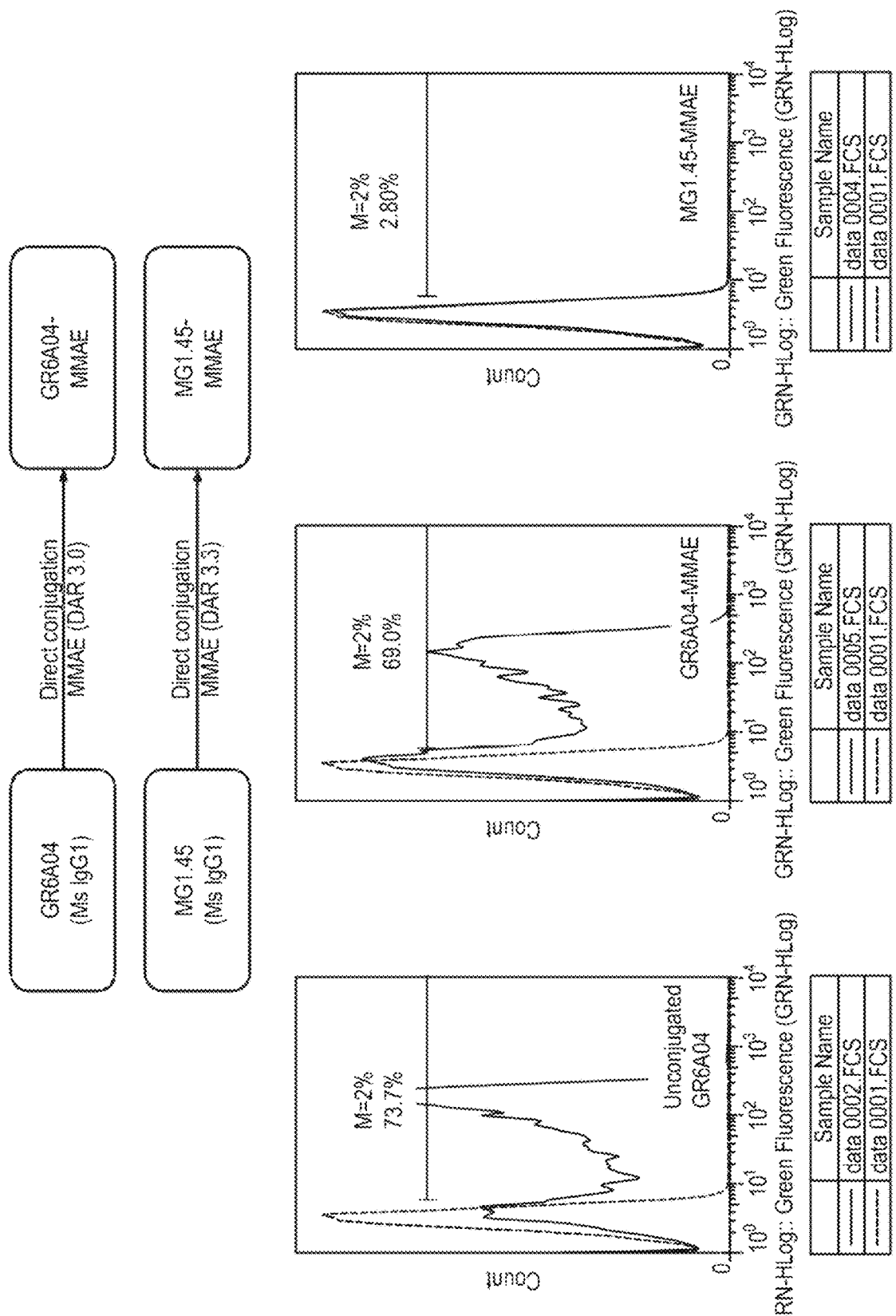

GR6A04-MMAE was conjugated with MMAE at a drug-to-antibody ratio (DAR) of 3.0, and at the same time, a commercial mouse IgG1 antibody (Clone MG1-45 from Biolegend) at a DAR of 3.3 using the same chemistry (FIG. 4C). Binding of GR6A04-MMAE on PC-9 and A549 cells was tested by flow cytometry, and found to be comparable to unconjugated GR6A04, while MG1-45-MMAE was determined to have negligible binding on these two lines.

Hu-GR6A04 was expressed in CHO cells, and the antibody purified from the culture supernatant using the same system as GR6A04. Purified Hu-GR6A04 was checked for correct protein size from the Coomassie blue stain from SDS-PAGE, with the heavy chain and light chain at the expected size of 50 kDa and 25 kDa respectively in the reducing lane, and the intact IgG at 150 kDa in the non-reducing lane. Similarly, binding of Hu-GR6A04 on PC-9 and A549 was comparable to GR6A04 on flow cytometry, shown in FIG. 4E.

GR6A04 Binds to N-Glycosylated CEACAM6

Figure 5A:
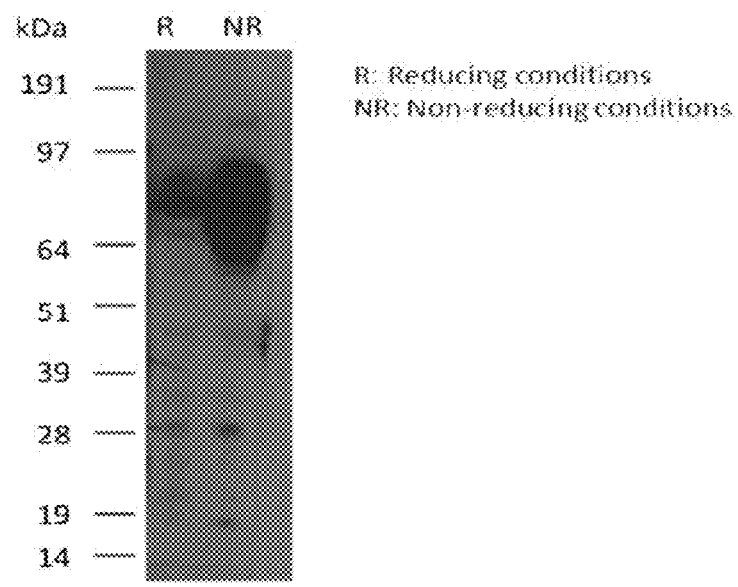
FIGS. 5A-5B show the characterization of GR 6A04 antigen. A) Western blot performed showed the antigen as a smear from 55-90 kDa. Antigen smearing reduced after treatment with β-mercaptoethanol (reducing agent). B) GR 6A04 binding is PNGase sensitive. GR 6A04's binding to the antigen is abolished with PNGase treatment (lane 3), accompanied by a drop in molecular weight indicating successful removal of N-glycans from the antigen. Anti-actin binding is not affected by the PNGase treatment. In other words, GR 6A04 binding is dependent on N-glycosylation of antigen.
Figure 5B:
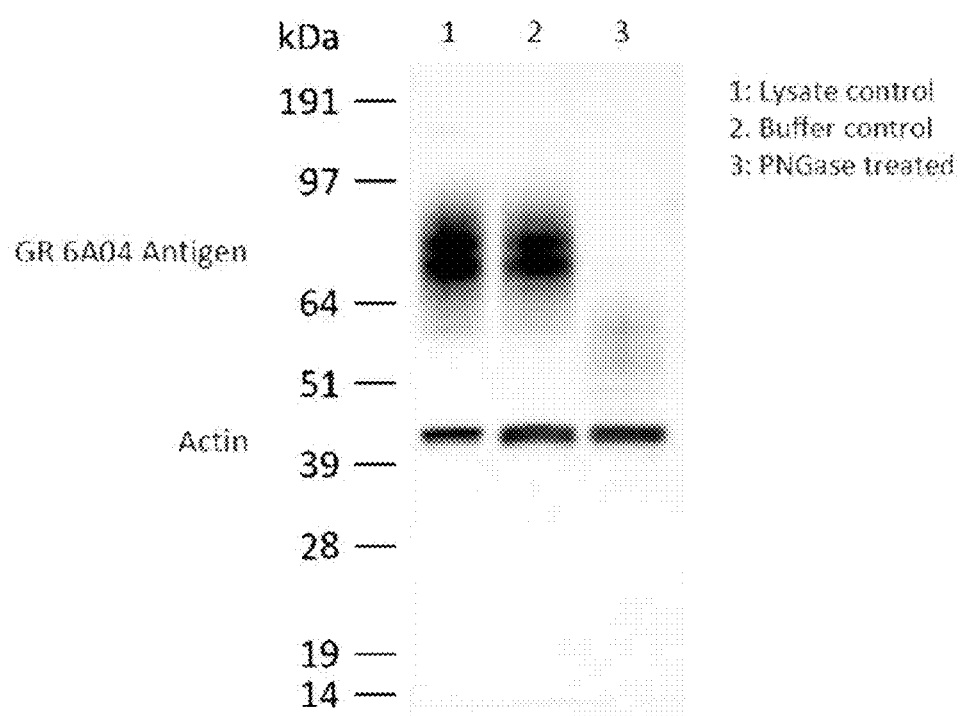

Western blotting of PC-9 cell lysates was immunoblotted with GR6A04, and found to recognise a smear of between 55-90 kDa on the non-reducing lane, shown in FIG. 5A. Antigen binding intensity was also weaker under reducing conditions. Additionally, treatment of the cell lysate by PNGase to remove N-linked glycans also abolished binding of GR6A04 to the antigen band, demonstrating the importance of N-glycosylation in the antibody recognition site.

Figure 7A:
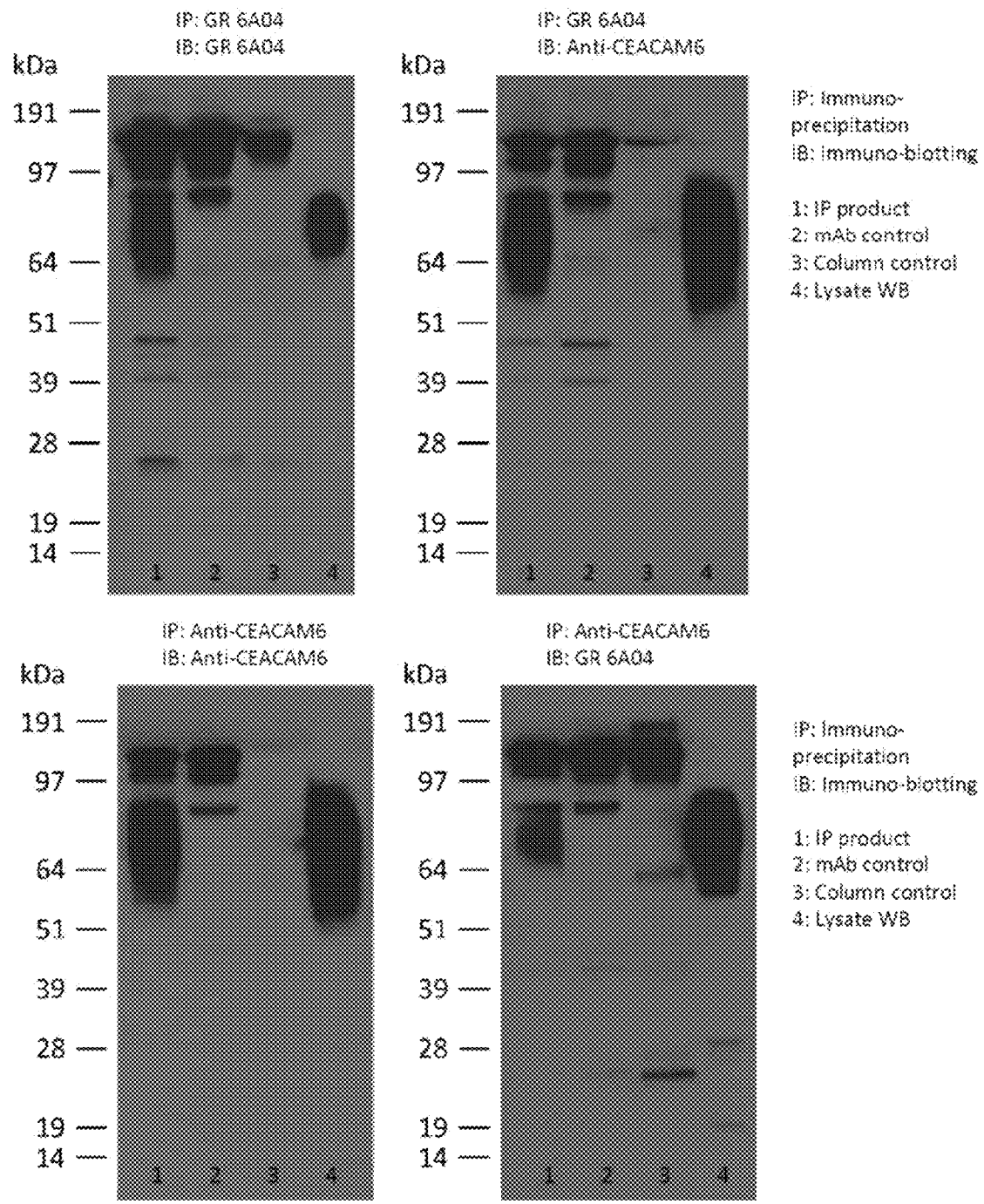
FIGS. 7A-7B show the validation of CEACAM6 as the putative antigen for GR 6A04. A) Cross-immunoprecipitation was performed with commercial anti-CEACAM6. Both the commercial anti-CEACAM6, and GR 6A04 recognised the antigen pulled-down by its counterpart. B) siRNA knock down of CEACAM6 was performed. The results showed that knockdown of the CEACAM6 expression in PC-9 cells led to a decrease in GR 6A04 binding observed in Western blot and flow cytometry.
Figure 7B:
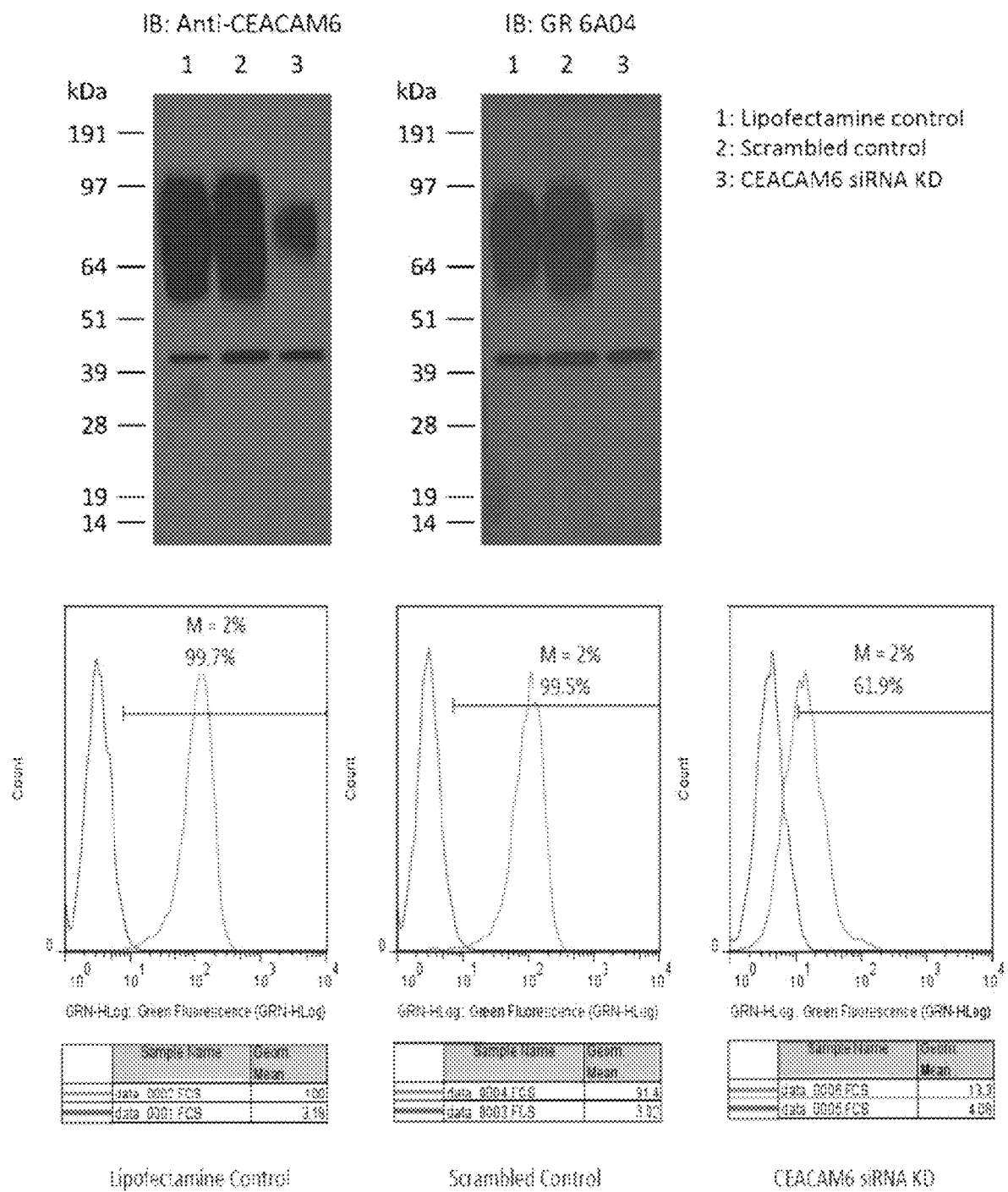
Figure 11C:
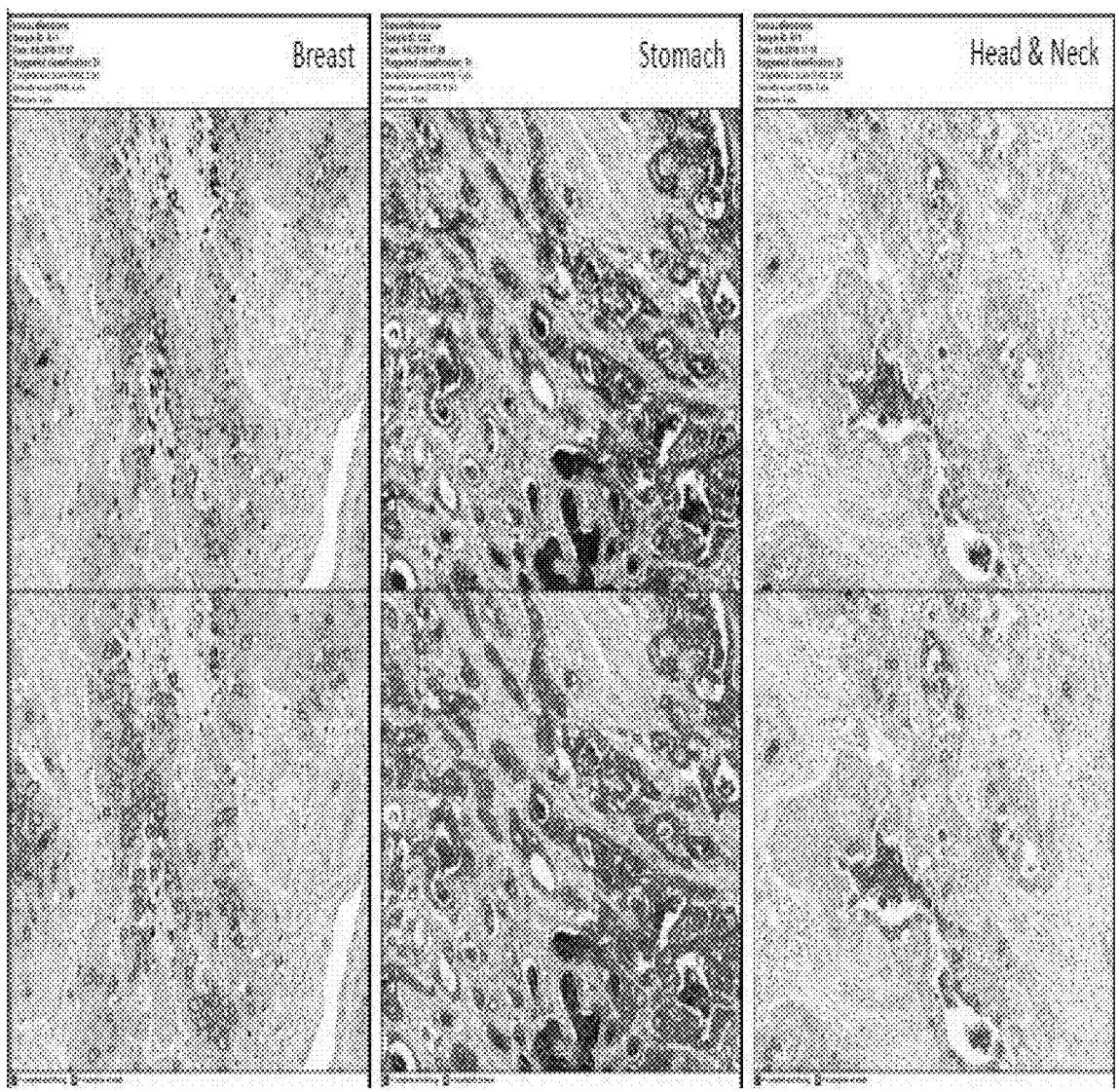
Figure 11C:
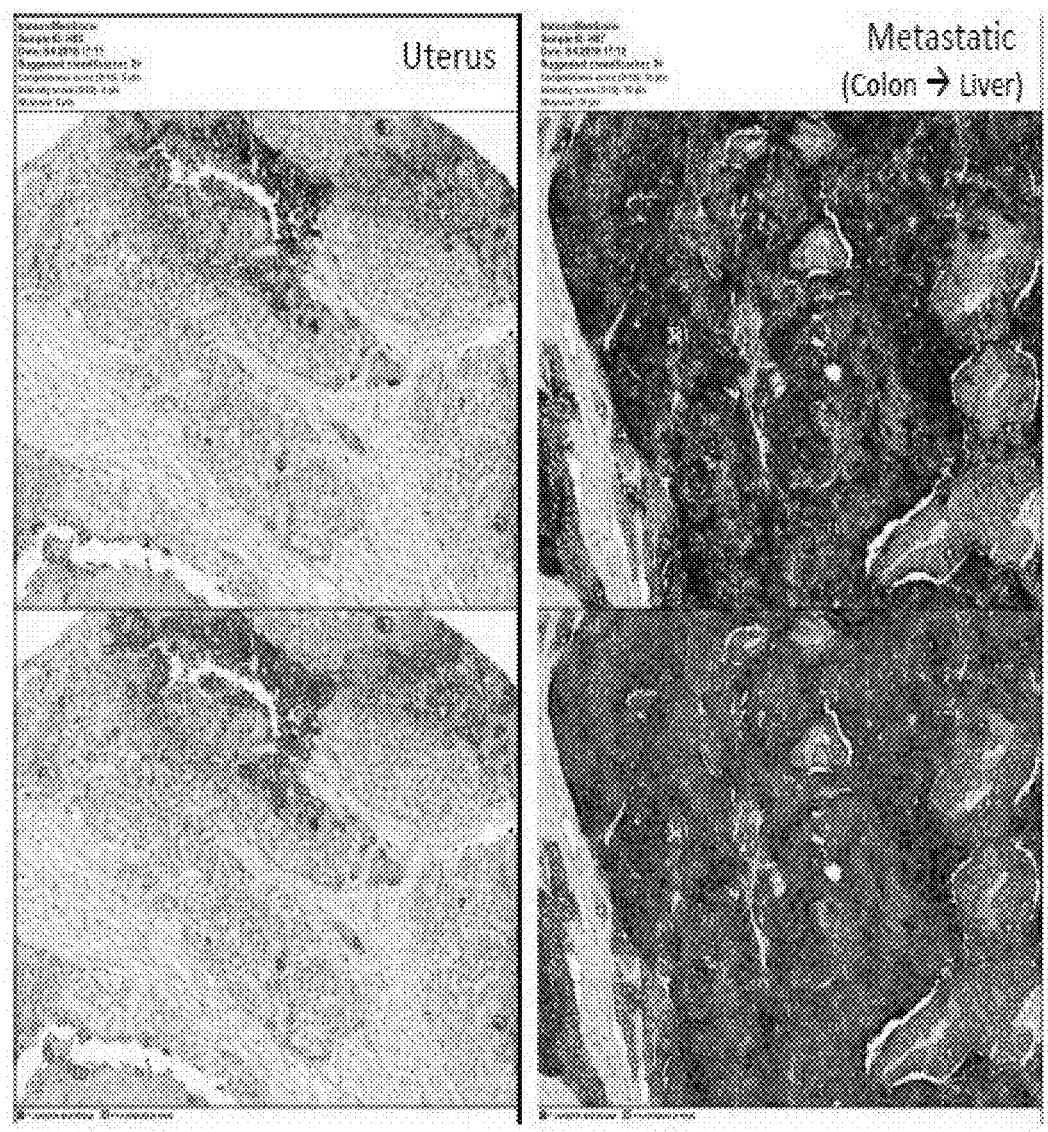

Immunoprecipitation (IP) with GR6A04 against PC-9 cell lysate enriched for the antigen, which was excised and sent for identification by mass spectrometry (FIG. 6A). The protein list was arranged by the overall score based on protein coverage and number of unique peptides found, and compared to the protein list from the column control. Top 5 putative antigens are listed in the table in FIG. 6B and validated by cross-IP with a commercial anti-CEACAM6 antibody (Clone 9A6 from Santa Cruz/Abcam) (FIG. 7A), and transient siRNA knock-down of CEACAM6 in PC-9 cells (FIG. 7B).

It can be concluded that GR6A04's antigen target is CEACAM6, whereby the N-glycan is important for antibody-antigen recognition.

GR6A04 Binding on Patient FFPE Tissue Samples

Having established that GR6A04 is specific to various cancer indications on flow cytometry, and does not bind to normal cells, we proceeded with determining GR6A04's binding on cancer patient tissue samples on formalin fixed paraffin embedded (FFPE) tissue microarrays (TMAs). Commercial FFPE TMAs were obtained from Pantomics.

Binding condition of GR6A04 for FFPE samples was optimised with FFPE cell line pellets, and determined to be at 5 μg/mL with a pH 9 antigen retrieval step. GR6A04 was observed to be localised to both the membrane and cytosol of PC-9 cells. To extend the binding profile of GR6A04 in other cancer cell lines, immunohistochemistry (IHC) staining was conducted on a FFPE cell line arrays covering larger range of cancer indications. GR6A04 was found to be reactive in gastric, lung, colorectal and pancreatic cancer cell lines (FIGS. 8A-8B).

Figure 13:
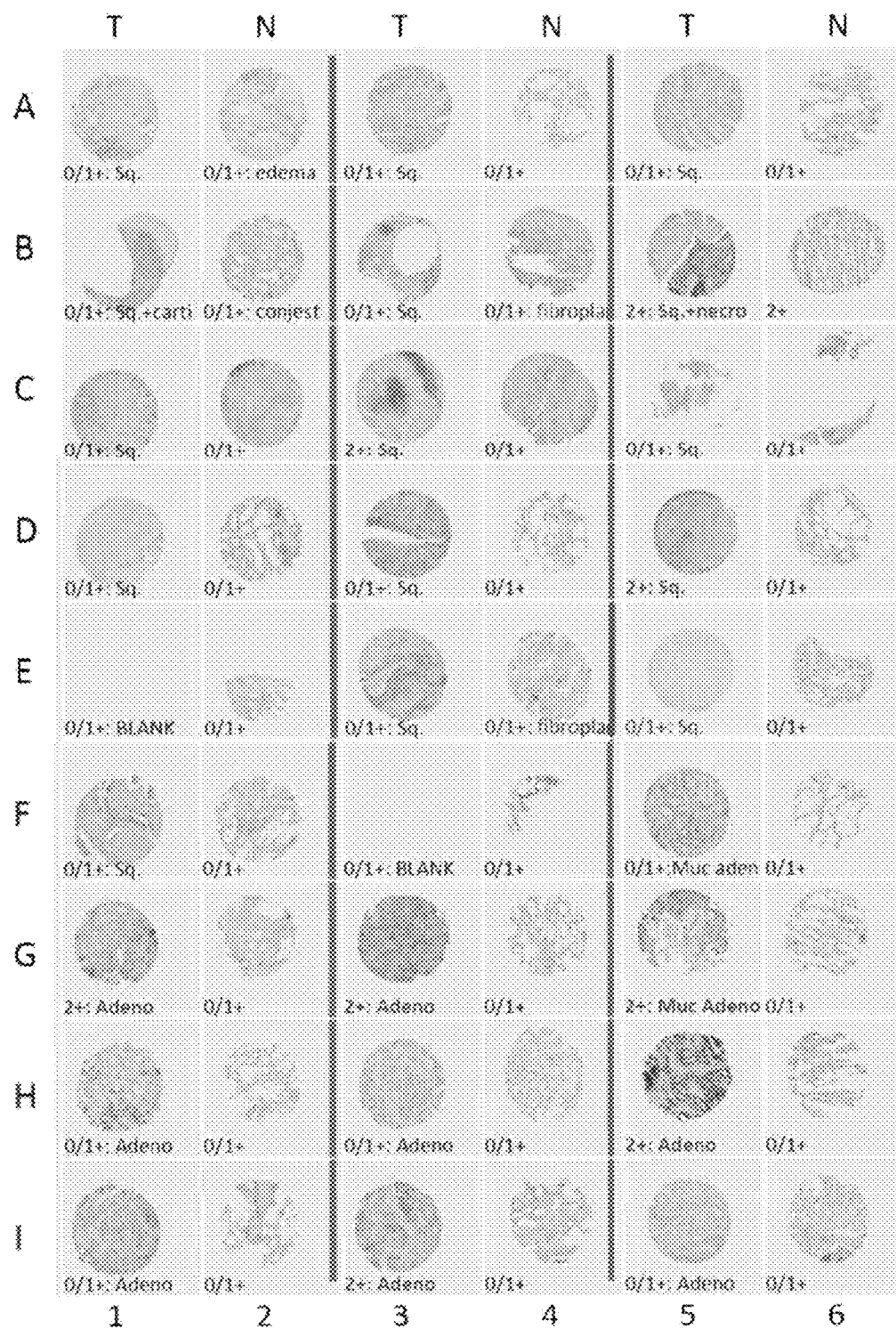
Figure 13:
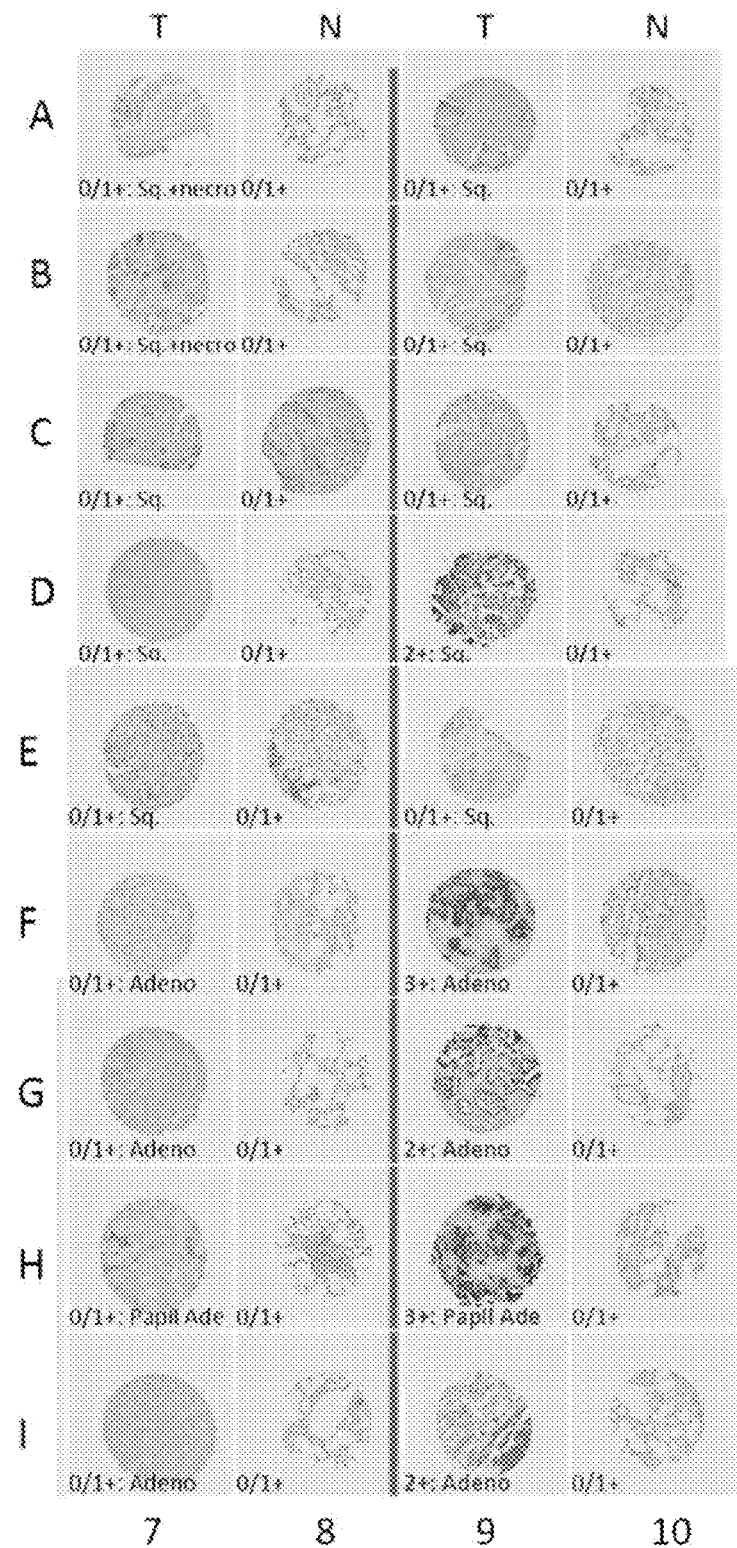

IHC staining on various FFPE TMAs covering cancer tissue samples from a wide array of organ origins were also done. GR6A04 staining was scored with the open source software: ImmunoMembrane. In a vast majority of tissue cores that was stained positive (2+ and 3+), binding was localised to the cell membrane. Some non-specific staining was also observed in necrotic regions. IHC staining on multi-tumour TMAs supported what was observed in cell line screening, whereby we observed that in addition to lung cancer, GR6A04 is also highly reactive to, but not limited to, gastro-intestinal (GI) and breast cancer (FIGS. 9, 10, and 11A-C). In a focused array for NSCLC, GR6A04 stained positive for 15% of squamous cell cancer, and 50% of lung adenocarcinoma cores represented in the TMA. Importantly, the adjacent normal tissue did not have any positive staining, demonstrating GR6A04 specificity towards cancer tissue (FIGS. 12 & 13).

Figure 14:
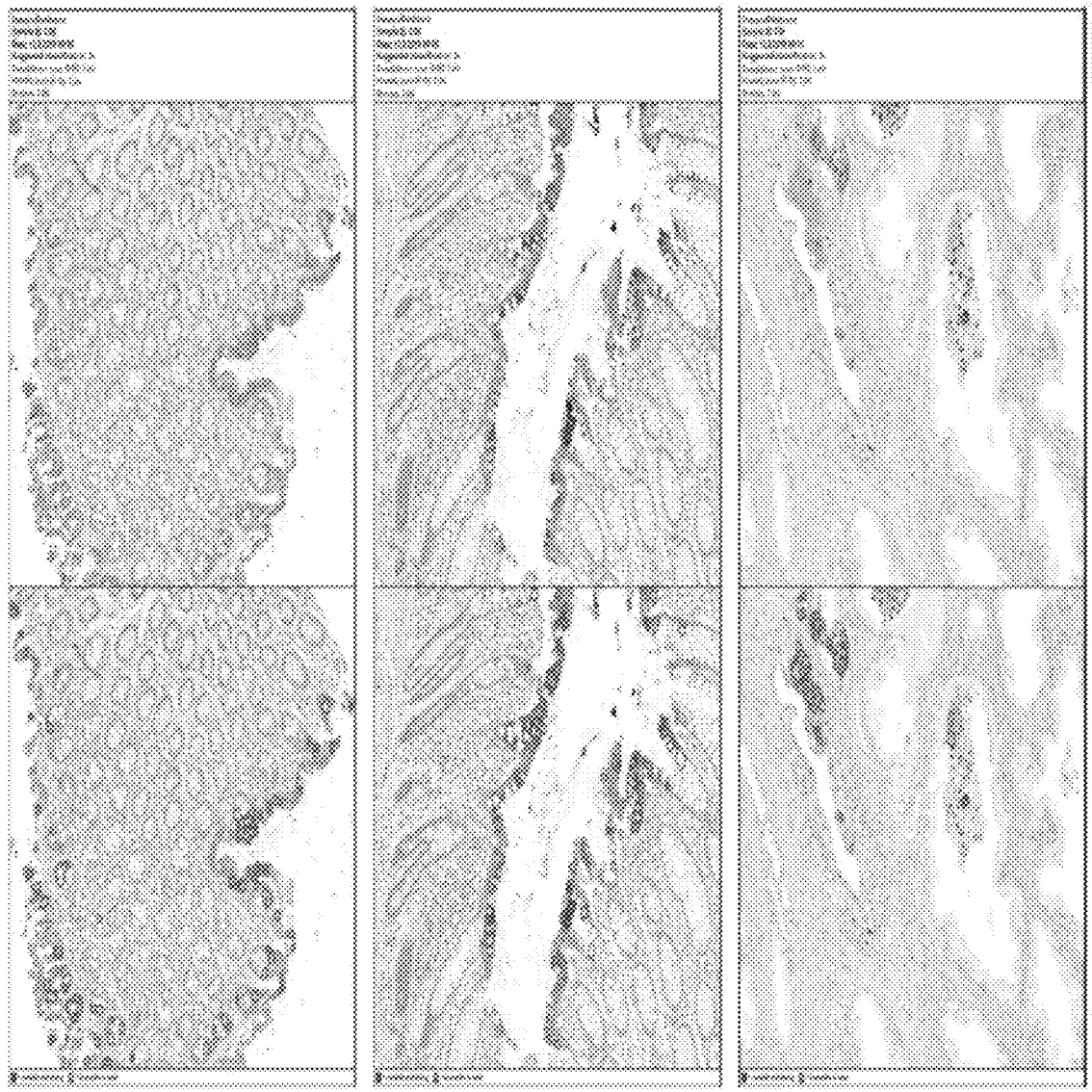
FIG. 14 shows negative staining for 93/96 of normal tissue tested (MNO961). Non-specific staining was generally found on ductal linings (edge of cores) and/or necrotic tissue.

In addition, GR6A04 was tested against FFPE normal tissues using the same staining protocol and scoring system. An FDA recommended TMA was used (MNO961), containing 35 different anatomical sites (FIG. 14). No staining of GR6A04 was observed in 93 of the 96 cores present, but 2 of 3 colon cores, and 1 of 3 prostate cores were weakly positive (2+). It should be noted that from the magnified images, the staining in these cases was mainly intracellular or in necrotic regions.

Hence, GR6A04 has demonstrated specificity towards a wide range of different cancer indications in patient tissue samples, and has negligible staining on normal tissue types, supporting our earlier binding profiles from flow cytometry and cell based screening.

Increased Specificity of GR6A04 Due to Glycan Recognition Site

Figure 15A:
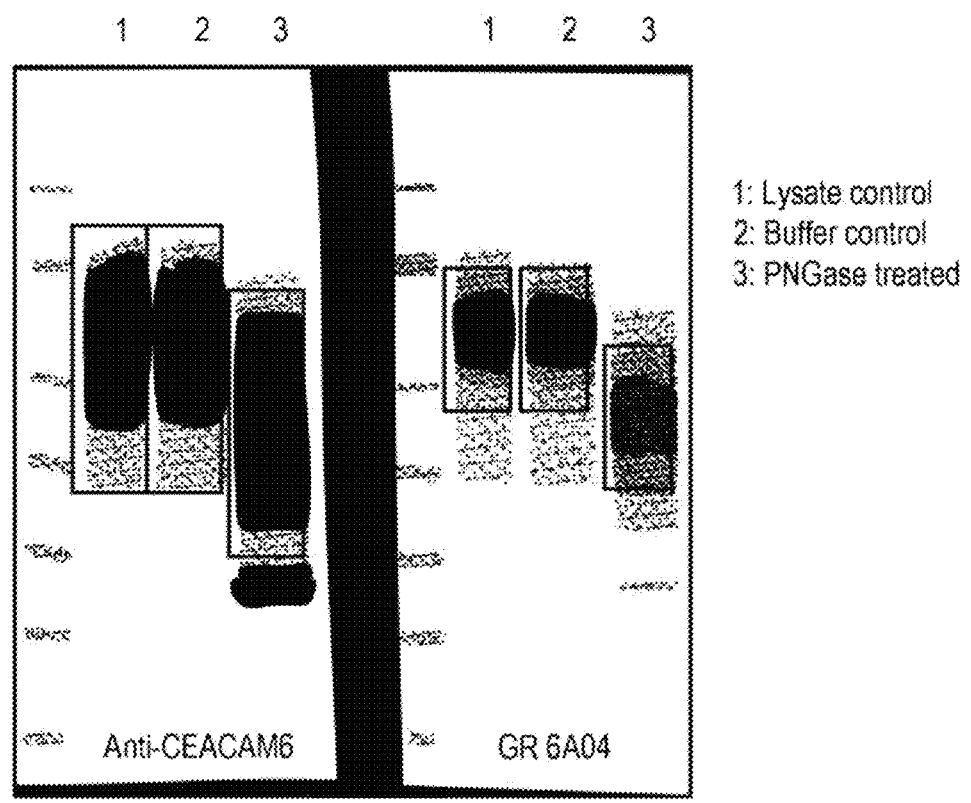
Figure 15B:
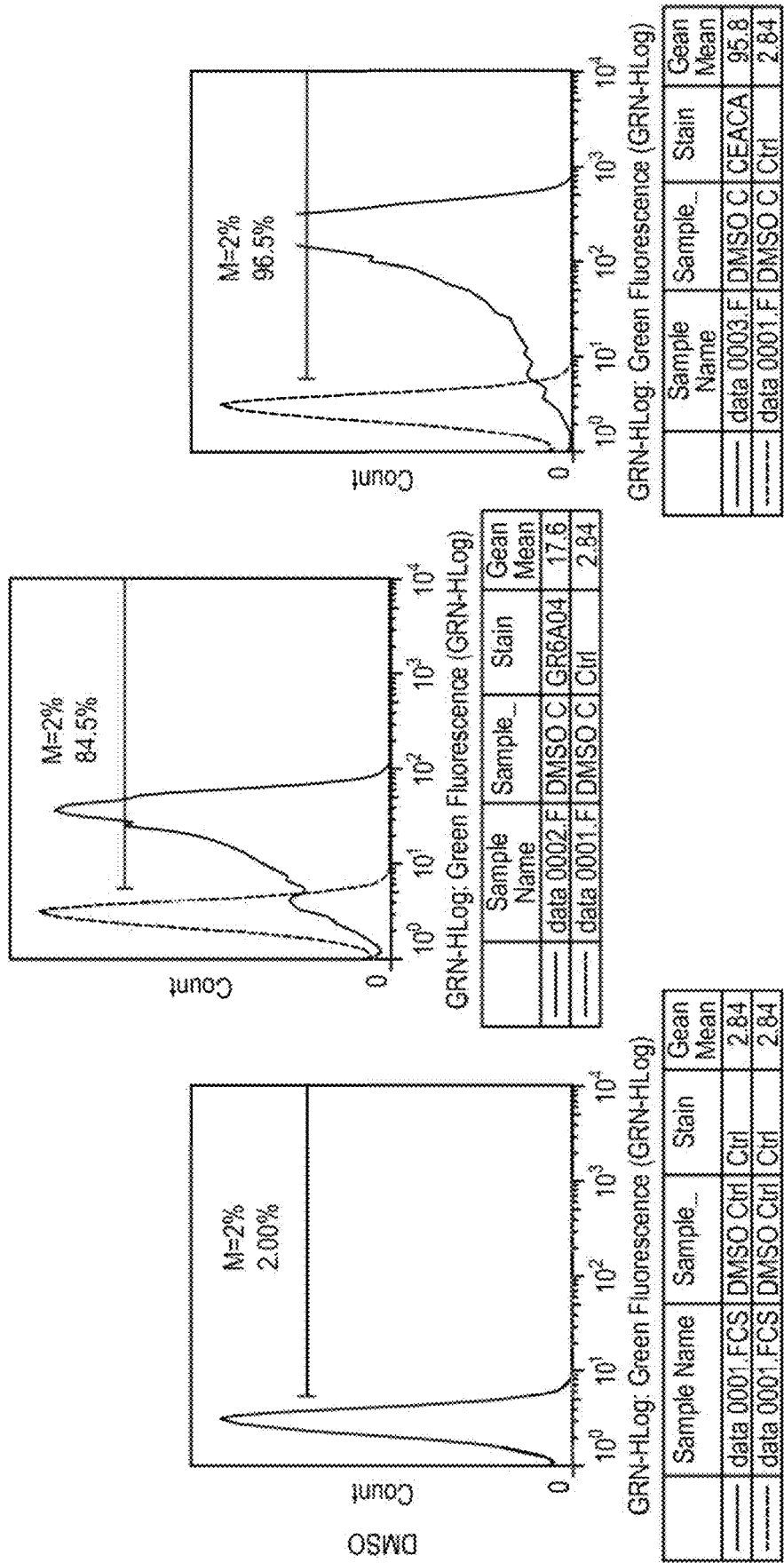

The commercial anti-CEACAM6 antibody used for the earlier validation is one that is not sensitive to changes in the glycosylation of CEACAM6 (i.e. Recognition site is not glycan dependent). This is demonstrated in FIGS. 15A-C, where the binding intensities remained unchanged after PNGase and Tunicamycin treatment, unlike GR6A04.

When the two anti-CEACAM6 (GR6A04 and commercial) were compared in an FFPE cell line microarray, while staining profiles were largely similar, the commercial antibody had one additional staining core in HCC827, while BxPC3 (pancreatic cancer line) also showed more intense and intracellular staining (15D).

Figure 16:
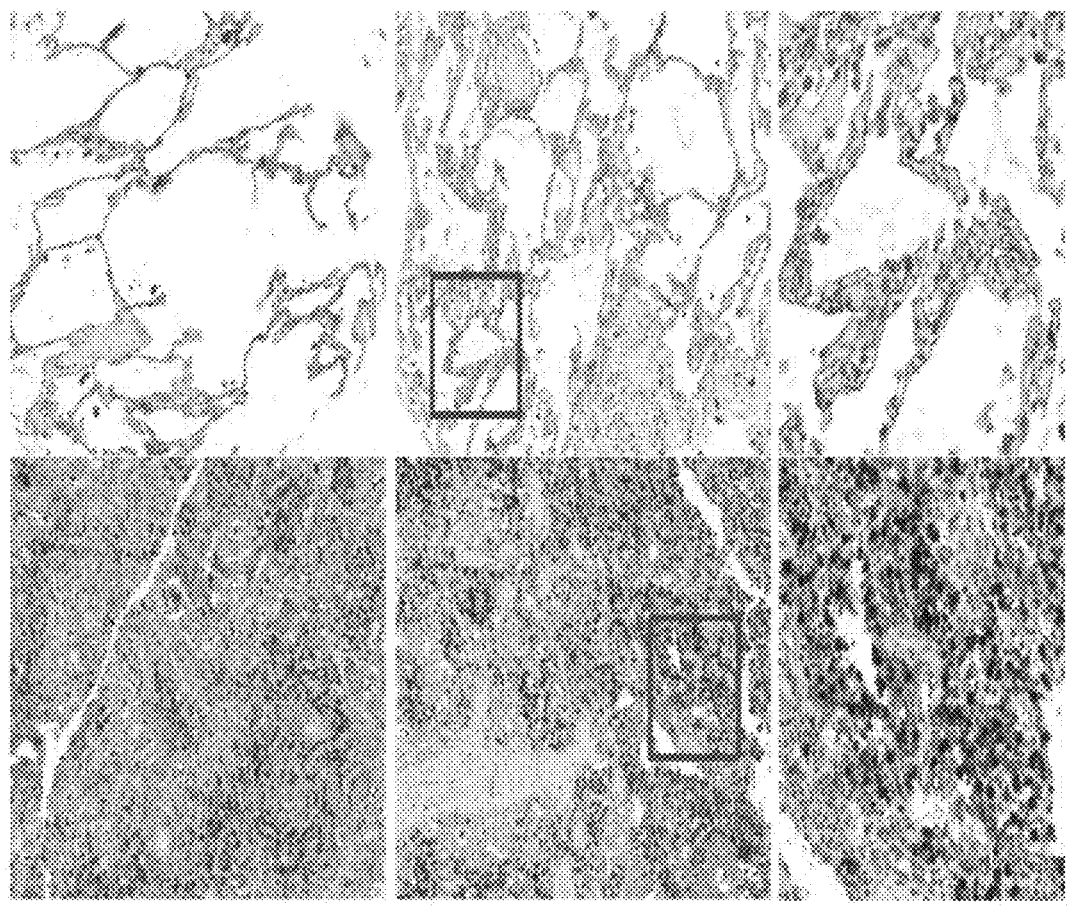
FIG. 16 shows differences in binding profiles were also observed for MNO961 (multi-normal TMA) where commercial anti-CEACAM6 has more non-specific binding, with higher staining intensity. In particular, all 3 normal lung and 2 normal spleen cores were scored positive.

This apparent non-specificity of the commercial anti-CEACAM6 was also observed in the TMA with normal tissues (MNO961), whereby 11 of 95 cores stained positive, as opposed to only 3 cores with GR6A04. Importantly, all three lung normal tissues, and 2 spleen normal tissues, showed staining on the cell membrane (FIG. 16).

The differences in staining profiles could be attributed to the differences in epitope binding sites on CEACAM6, especially that arising from the N-glycans on CEACAM6. This allowed for an extra degree of specificity in addition to binding on CEACAM6 protein alone, which leads to reduced non-specific binding on normal tissues. This is important as it provides an added level of safety if GR6A04 is to be developed for therapy.

Characteristics of GR6A04$^+$ A549 Subpopulations

Figure 17A:
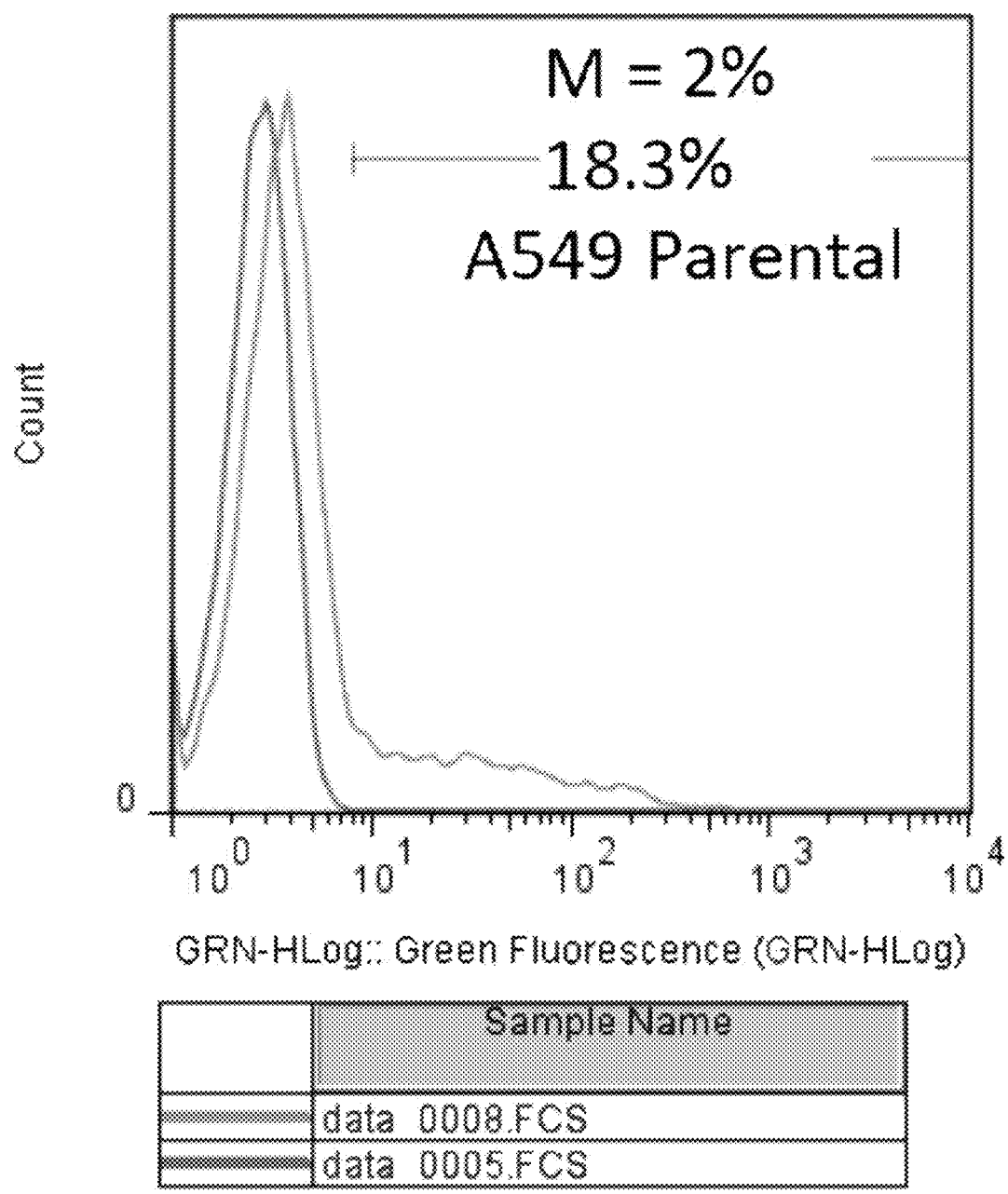
FIGS. 17A-17E show sorting of A549 cells. A) A549 lung adenocarcinoma cell line showed heterogeneous binding of GR6A04 and a positive binding tail of 15-30%. B) Sorting A549 cells with GR6A04 using Dynabeads Pan Ms-IgG beads followed by DNase bead release showed enrichment of GR6A04+ percentages at P0, but loss of binding was observed with subsequent passages (Round 1 of sorting from A549 parental cells (Positive fraction)). C) Multiple rounds of sorting established stable differential lines. D) A549-GR6A04+ single-cell (SC) clones that were generated showed improved homogeneity of GR6A04 binding. E) Differences in morphology between A549-GR6A04+ single-cell (SC) clones.
Figure 17B:
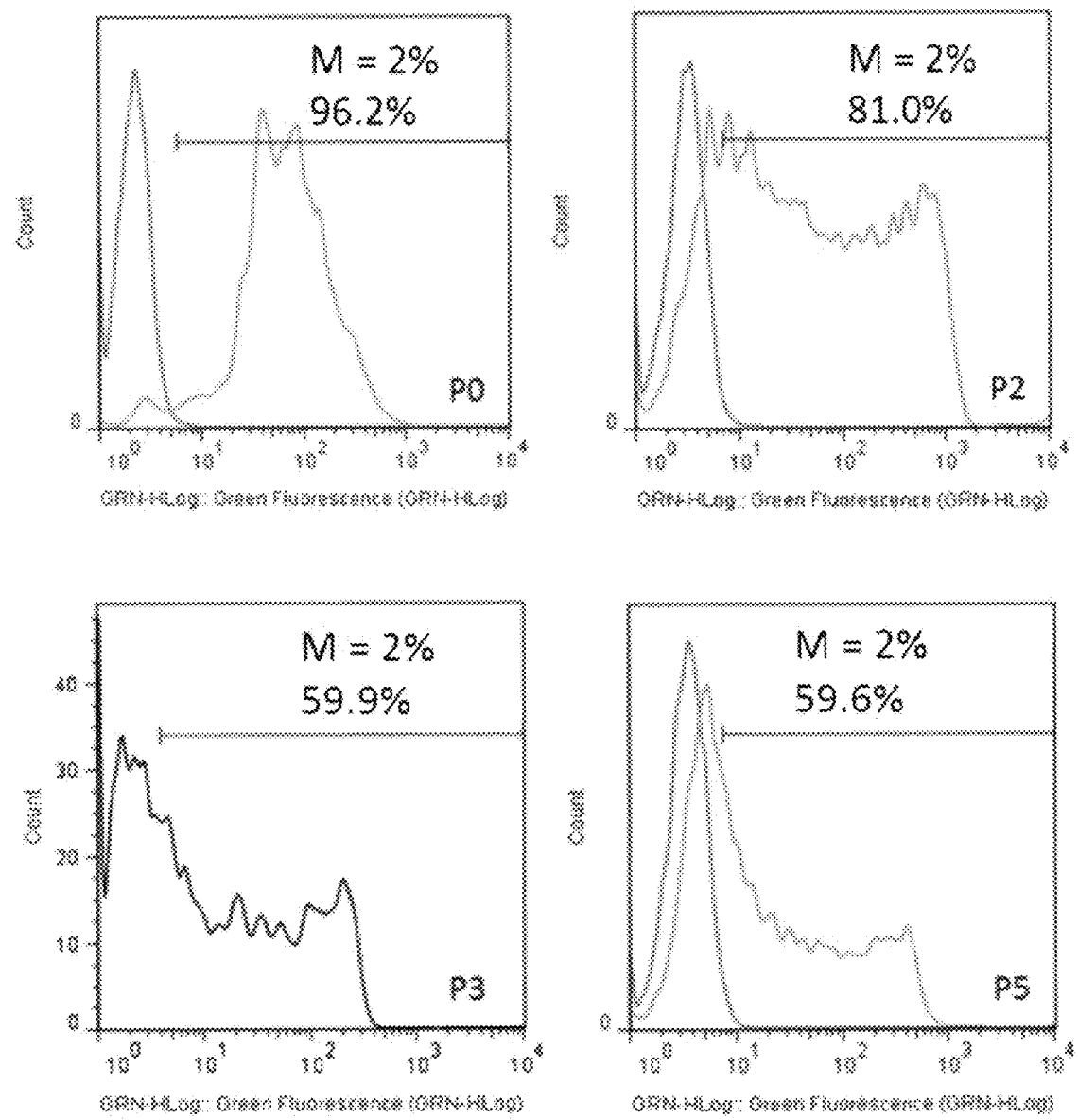
Figure 17C:
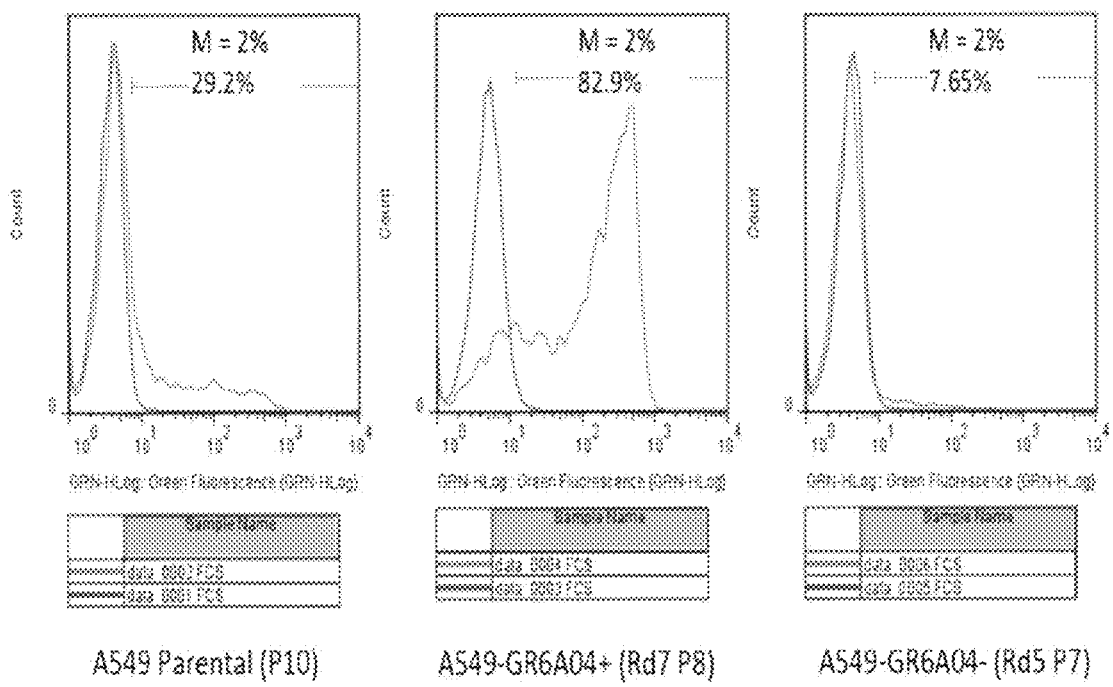
Figure 17D:
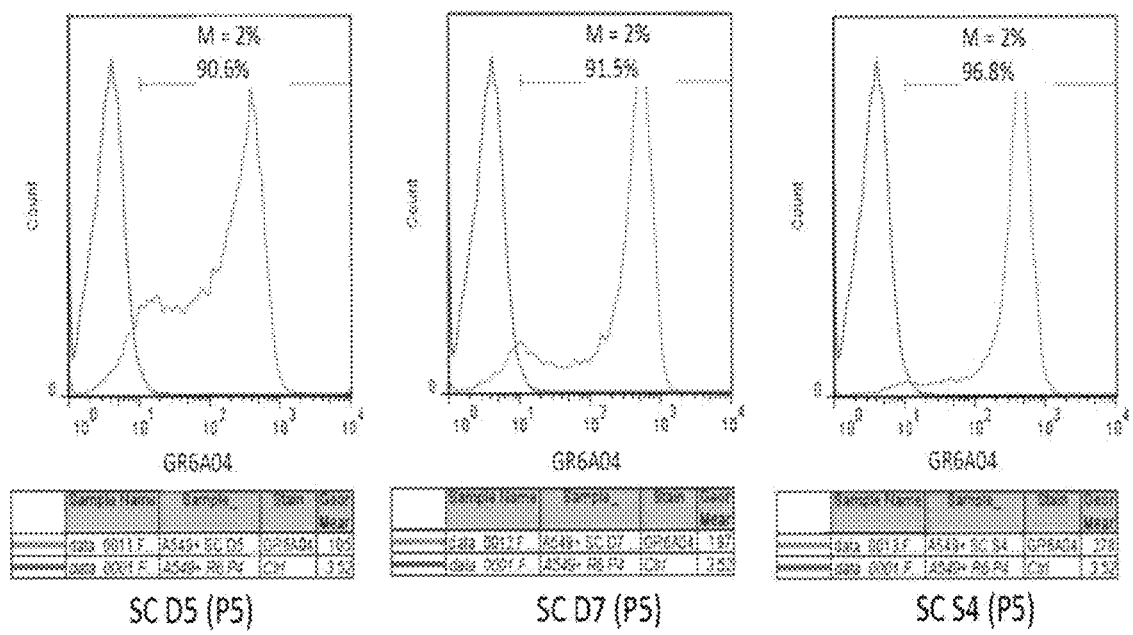
Figure 17E:
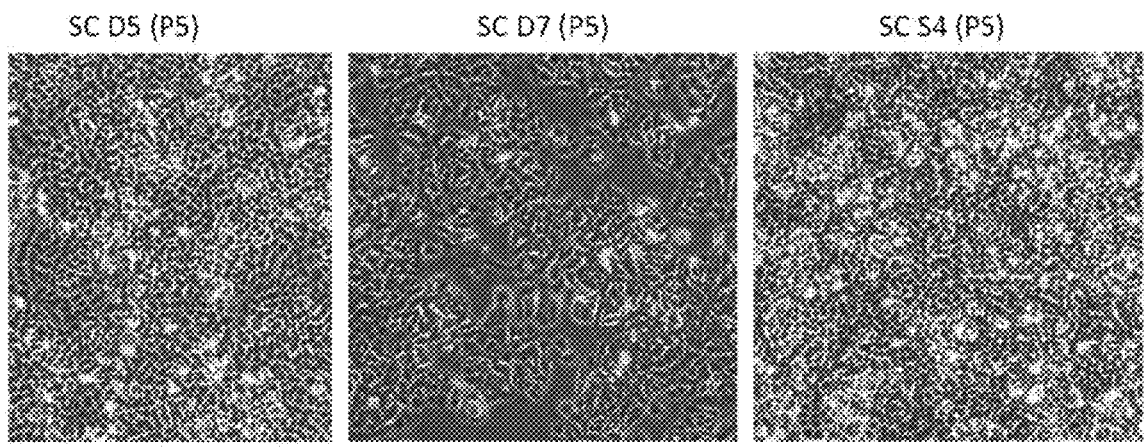

The lung adenocarcinoma cell line, A549, is a good biological model to investigate the role of glycosylated CEACAM6 expression in cancer due to heterogeneous binding for GR6A04, with only a small 15-30% GR6A04$^+$ population (FIG. 17A). Through the use of magnetic sorting with CELLection™ Pan Mouse IgG Kit, both the GR6A04$^-$ and GR6A04$^+$ could be enriched for. Although it must be noted that reduction of GR6A04 binding was observed with increasing passages in culture. Multiple rounds of consecutive sorting mitigates this, and after 7 rounds of isolation for GR6A04$^+$ and 5 rounds for GR6A04$^-$ cells, stable differential lines were obtained, and subsequently referred to as A549-GR6A04+ and A549-GR6A04- respectively (FIGS. 17B & C). Additionally, single cell clones from A549-GR6A04+ cultures were isolated that demonstrated strong, homogeneous binding of GR6A04 (D5, D7 and S4 clones). These were observed to have different cell morphology between clones (FIGS. 17D & E). In particular, D5 clones showed dense clusters with round morphology. D7 showed spindle-shaped cells and S4 showed SCLC-like morphology with attachment independent growth.

Figure 18A:
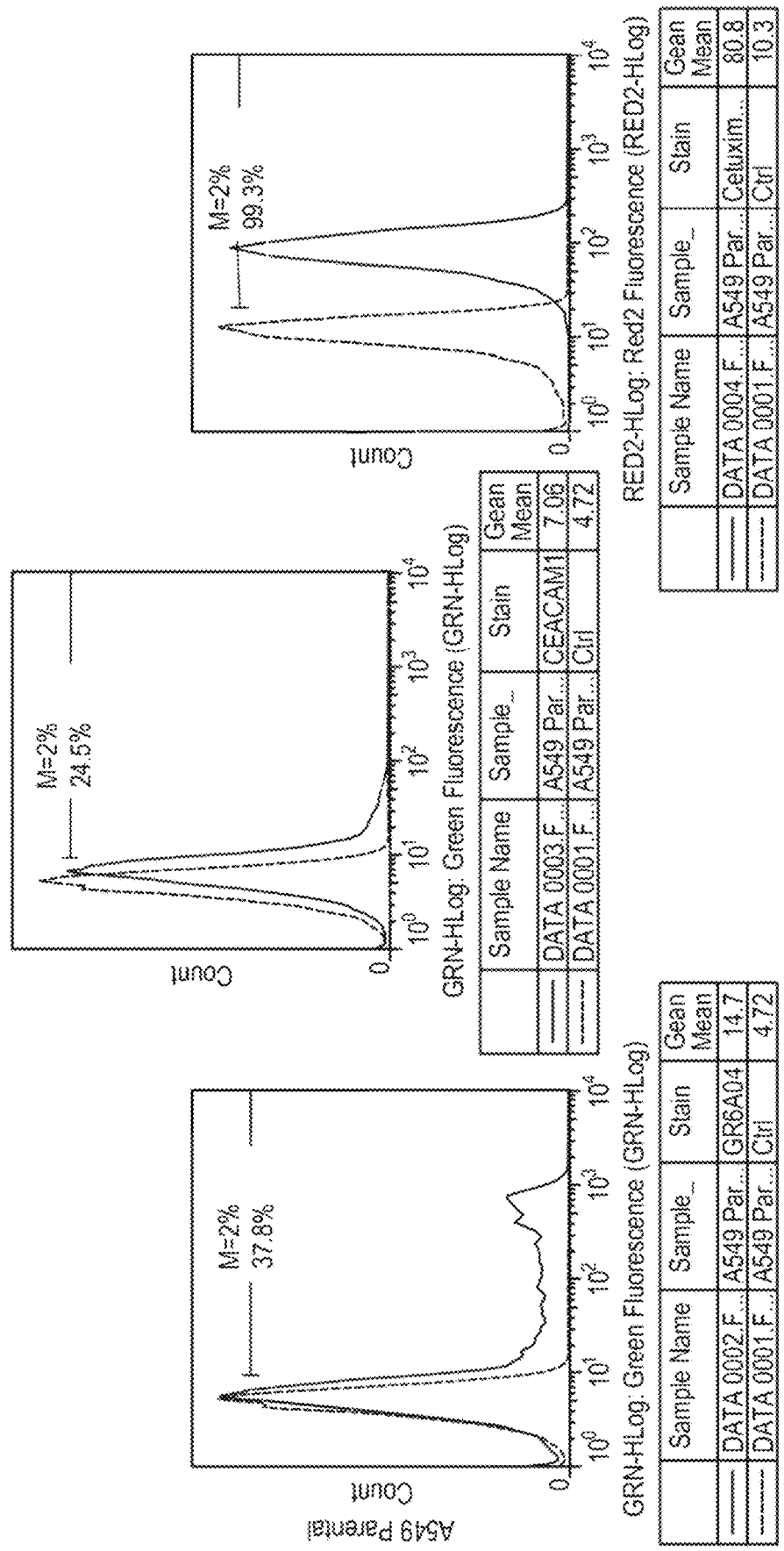
FIGS. 18A-18C show characterization of sorted populations. EGFR was down-regulated in A549-GR6A04+ cells and CEACAM1 was up-regulated in A549-GR6A04+ cells.
Figure 18B:
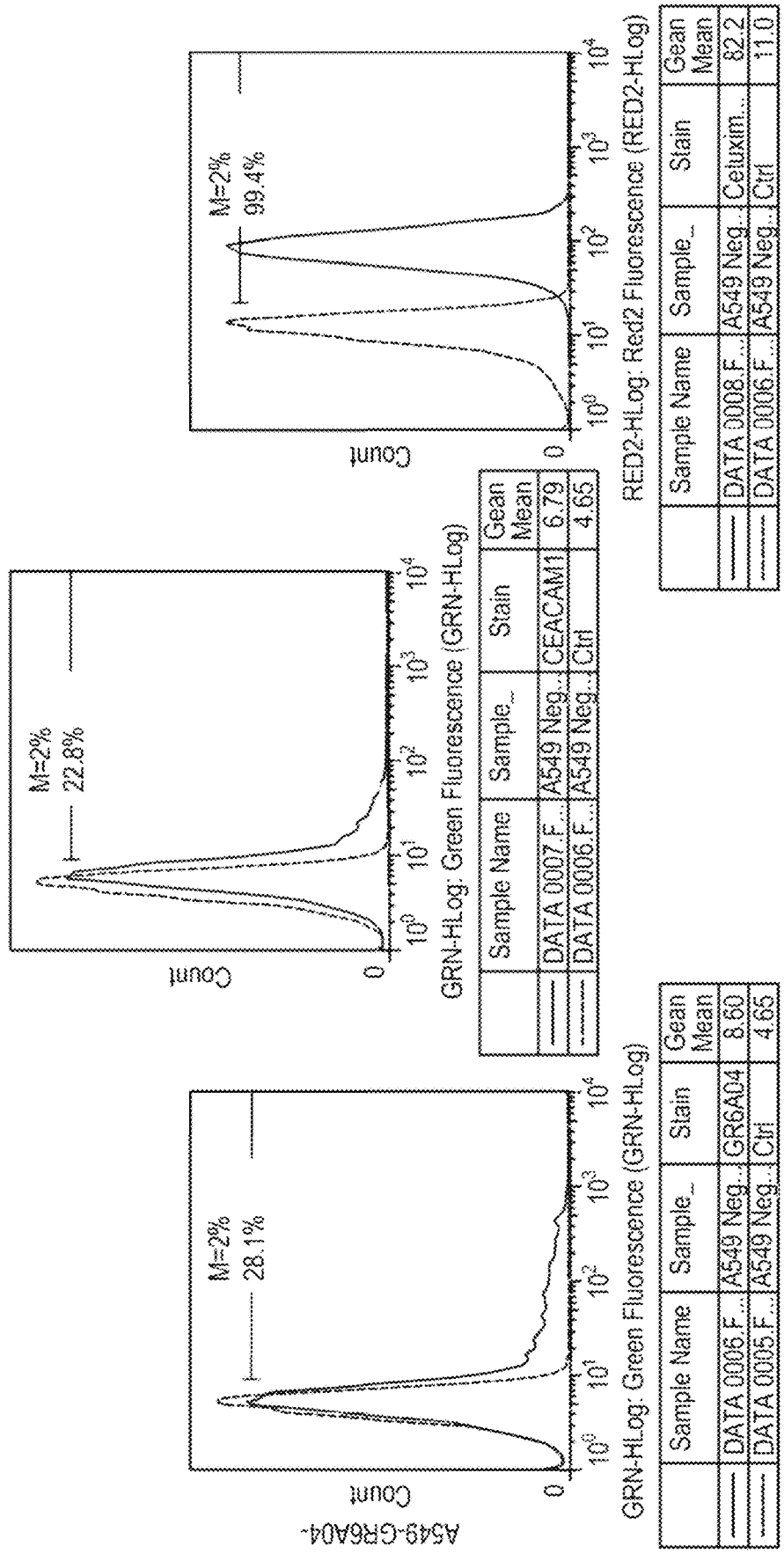
Figure 18C:
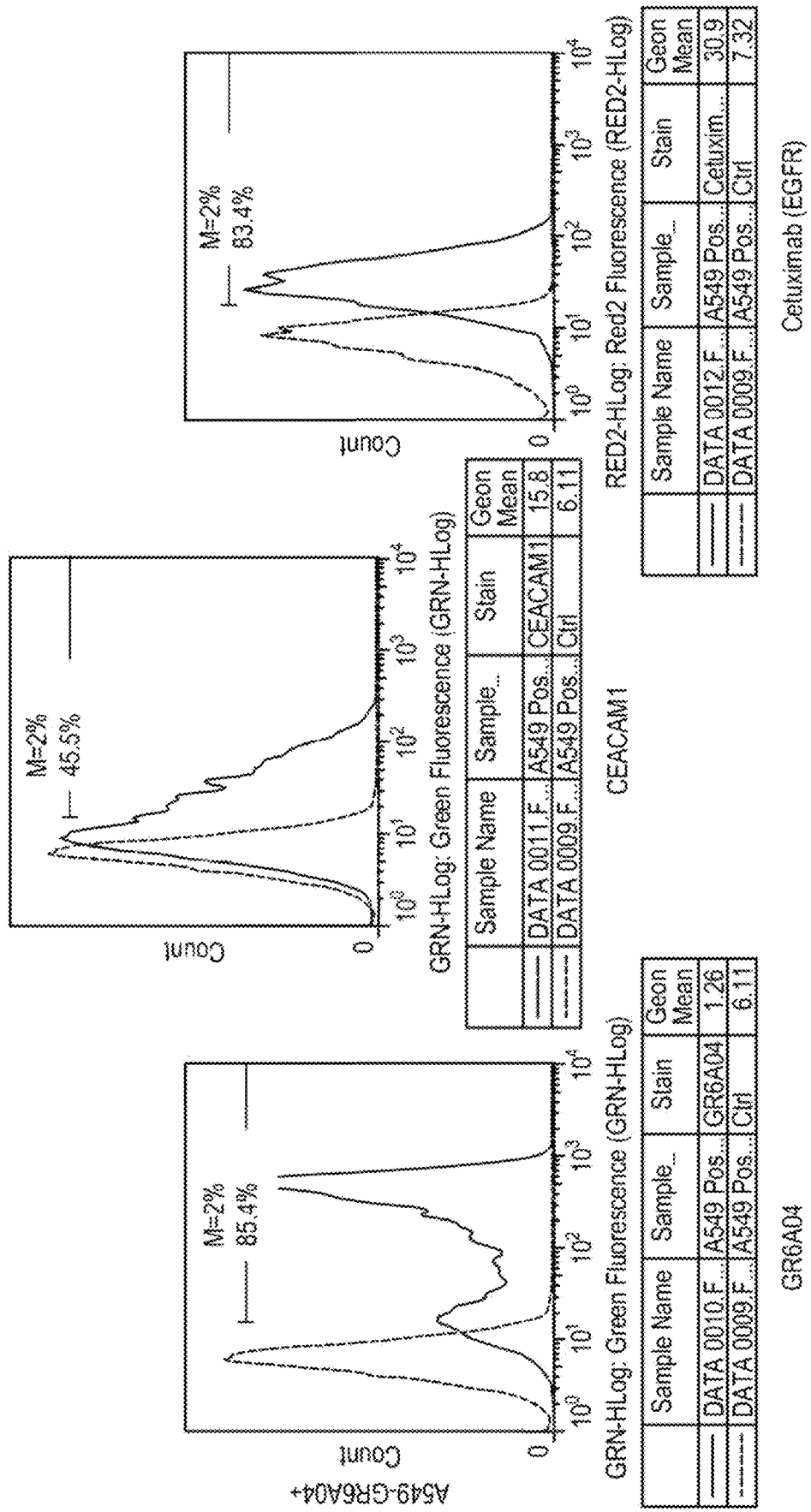

Expression of EGFR and CEACAM1 was measured by flow cytometry on these sub-populations, and also the parental line. While expression of these two markers in A549-GR6A04- cells and the parental A549 were similar, A549-GR6A04+ cells had a much lower expression of EGFR (25% decrease in MFI), and an increase in CEACAM1 binding was also observed (FIGS. 18A-C).

Figure 19A:
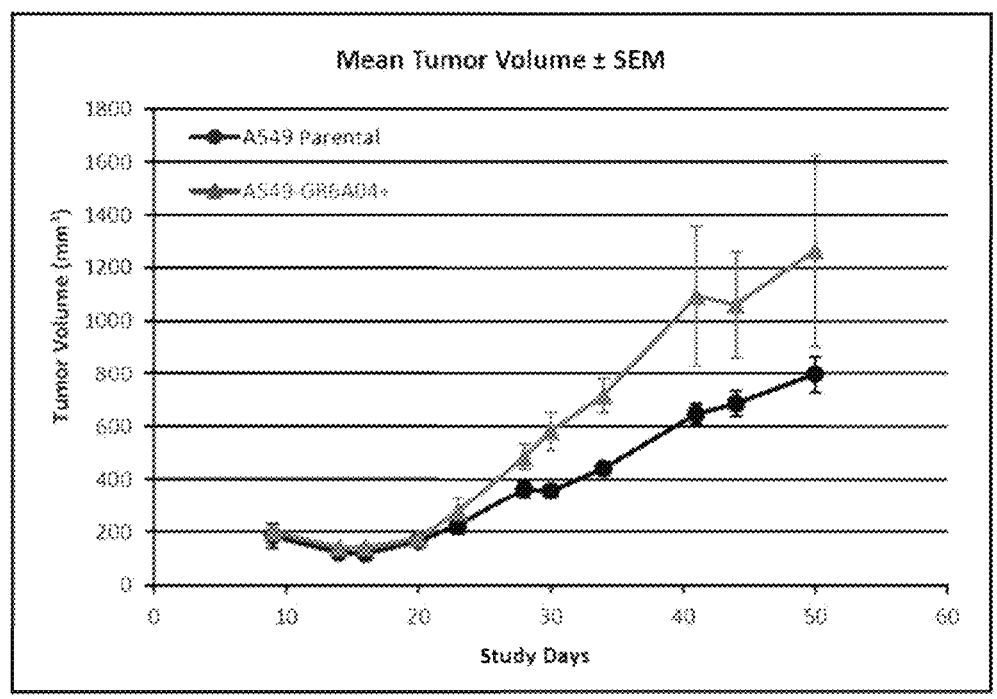
FIGS. 19A-19B show the in vivo functionality of GR6A04, using xenograft models of A549 lung adenocarcinoma; A549-GR6A04+ and A549 parental, A) A549-GR6A04+ cells have increased tumorigenicity. B) A549 parental, and Retention of GR6A04 binding at end-point where A549 parental was selected for GR6A04+ cells in xenograft (20% to >70%).
Figure 19B:
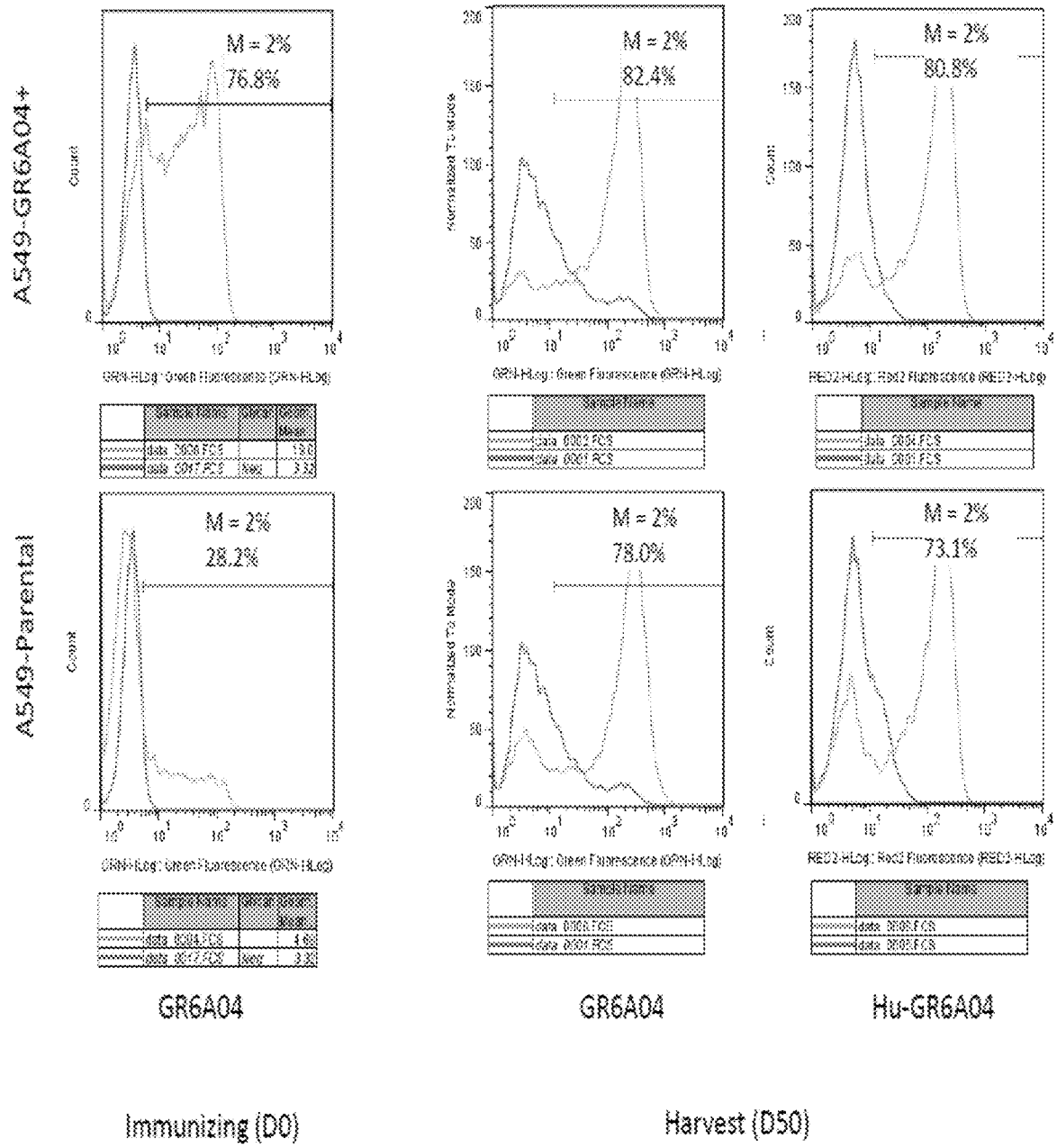

GR6A04 expression was also found to affect tumorigenicity in vivo. In an A549 xenograft model in Nude mice, whereby the same initial cell numbers were injected subcutaneously, A549-GR6A04+ cells formed larger xenografts than the A549 parental cells (FIG. 19A). When the xenograft was dissociated at the end of the 50 day study, it was also found that percentage of GR6A04 in the xenografts obtained from A549 parental cells increased from around 20% at the point of injection, to >70% by Day 50 (FIG. 19B).

Figure 20:
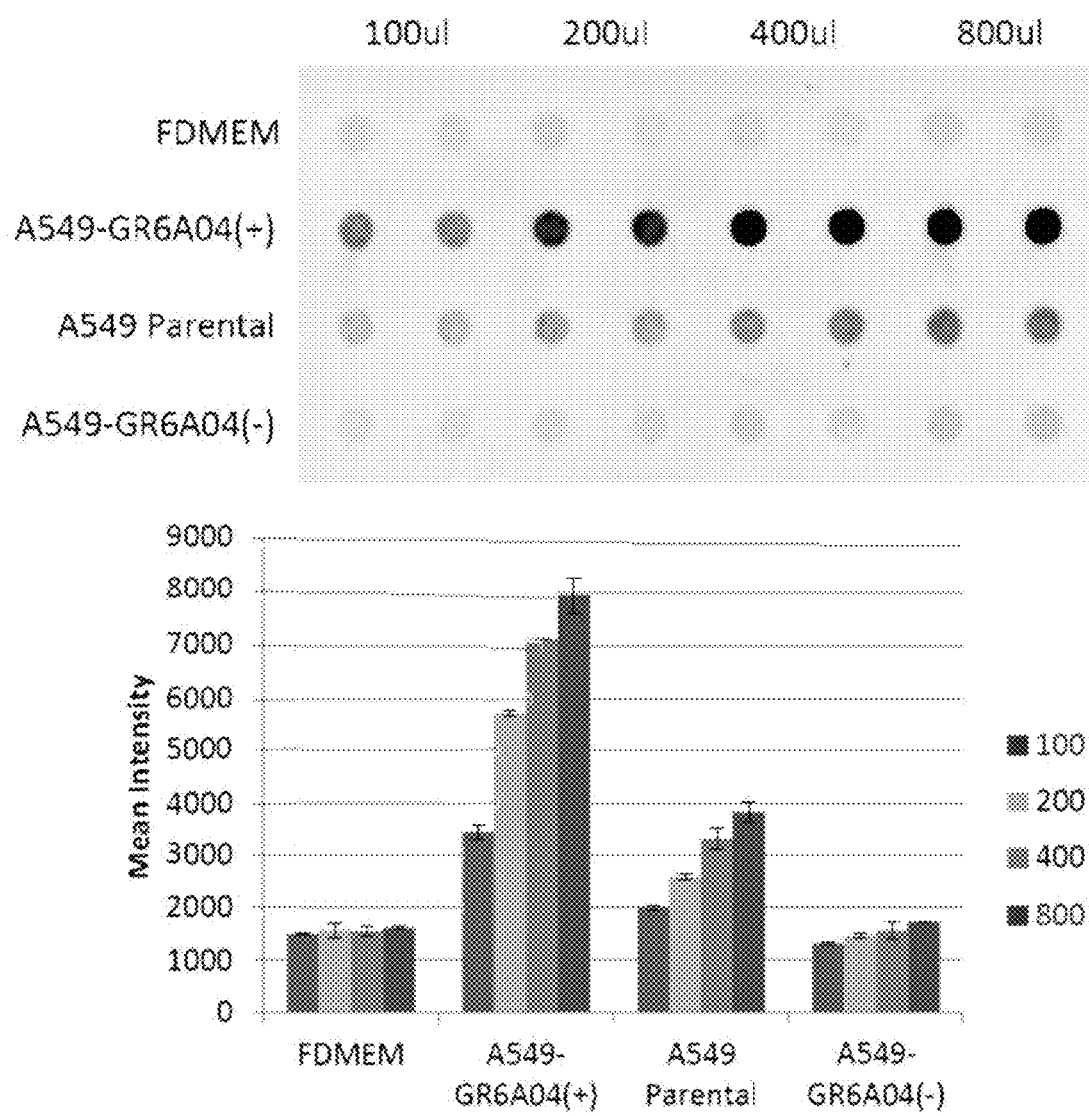
FIG. 20 shows that the antigen of GR 6A04 is leached into conditioned media. Media was conditioned for 5 days with cultured cells, known volumes were blotted onto membranes in duplicates and probed with Hu-GR6A04. The results showed that higher antigen levels could be found in the conditioned media from GR 6A04(+) cells than from A549 parental cells and GR6A04 (−) cells.

To establish if GR6A04 could have potential application as a serum biomarker for lung cancer, conditioned media from A549 subpopulations were spotted on a membrane and immunoblotted with GR6A04. The antigen is detectable in the conditioned media from the A549-GR6A04+ and A549 parental cell cultures, but not in the A549-GR6A04- cultures, and intensity is proportional to the volume of media spotted (FIG. 20). The results show that GR6A04 may be used for antigen quantification in patient serum samples.

In Vitro and in Vivo Functional Assays

Figure 21A:
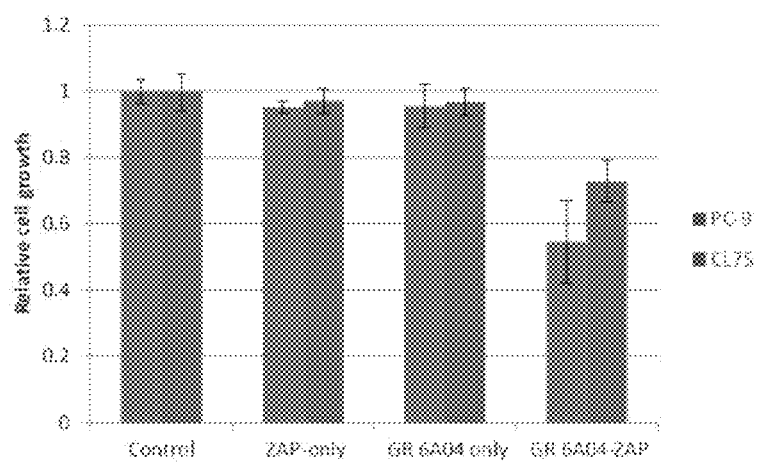
FIGS. 21A-21B show characterization of the antibody drug conjugate of GR 6A04. A) The Mab-ZAP Antibody Internalization Kit as was used as proof of concept. GR 6A04 was indirectly conjugated with saporin using an anti-mouse secondary antibody linked with the toxin. B) GR 6A04 was internalized in PC-9 cells. Pre-incubation of GR 6A04, 10 μg/mL at 4° C. for 20 min was performed. Cells were fixed at time points and probed with anti-Ms AlexaFluor 488. Images were taken at 40×. The results showed that GR 6A04 localised as a ring (solid arrows) on the cell periphery/membrane at T=0 min and as a ring (solid arrows) and also intracellularly (dashed arrows) at T=120 min.
Figure 21B:
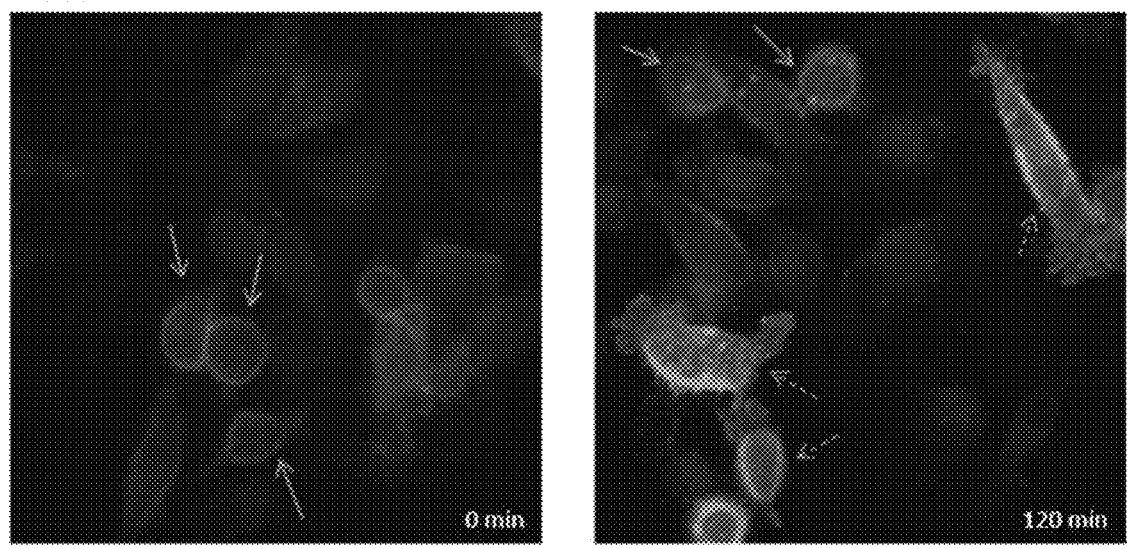

Having established GR6A04's specificity and its possible roles in cancer biology in the previous sections, this section focuses primarily on the functionality of the mAb as a cancer therapeutic. As an early test for function as an antibody-drug conjugate (ADC), GR6A04 was indirectly conjugated with saporin (ribosome inactivating protein) using an anti-mouse antibody conjugated with the toxin. Cell growth was inhibited in both the PC-9 sensitive parental line, and CL75 GR clone by 43% and 28% respectively (FIG. 21A). GR6A04 was also observed to be able to internalise within 120 min at 37° C., with the mAb being localised to the cell periphery after binding at 0 min, and subsequently found distributed within the cell cytoplasm (dashed arrows) at 120 min. A proportion of cells, however, has not internalised the mAb at 120 min, and the mAb was still localised on the surface (solid arrows) (FIG. 21B).

Figure 22A:
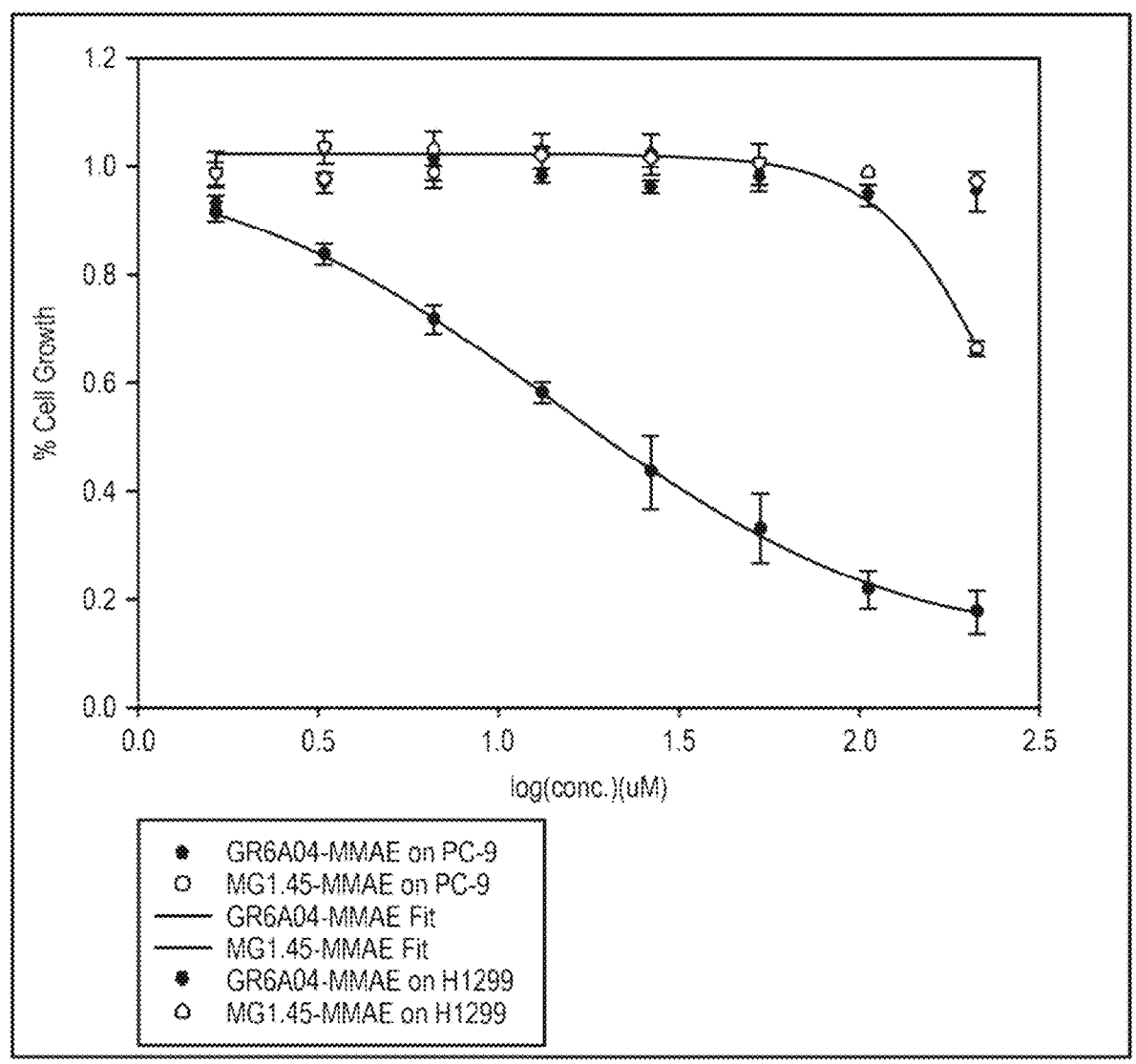
FIGS. 22A-22B show in vitro functionality of GR6A04-MMAE (direct conjugation of toxin), with dose-response curves estimating EC50 @ 19.58 nM against PC-9; EC50 @ 3.33 nM against A549-GR6A04+ cells.
Figure 22B:
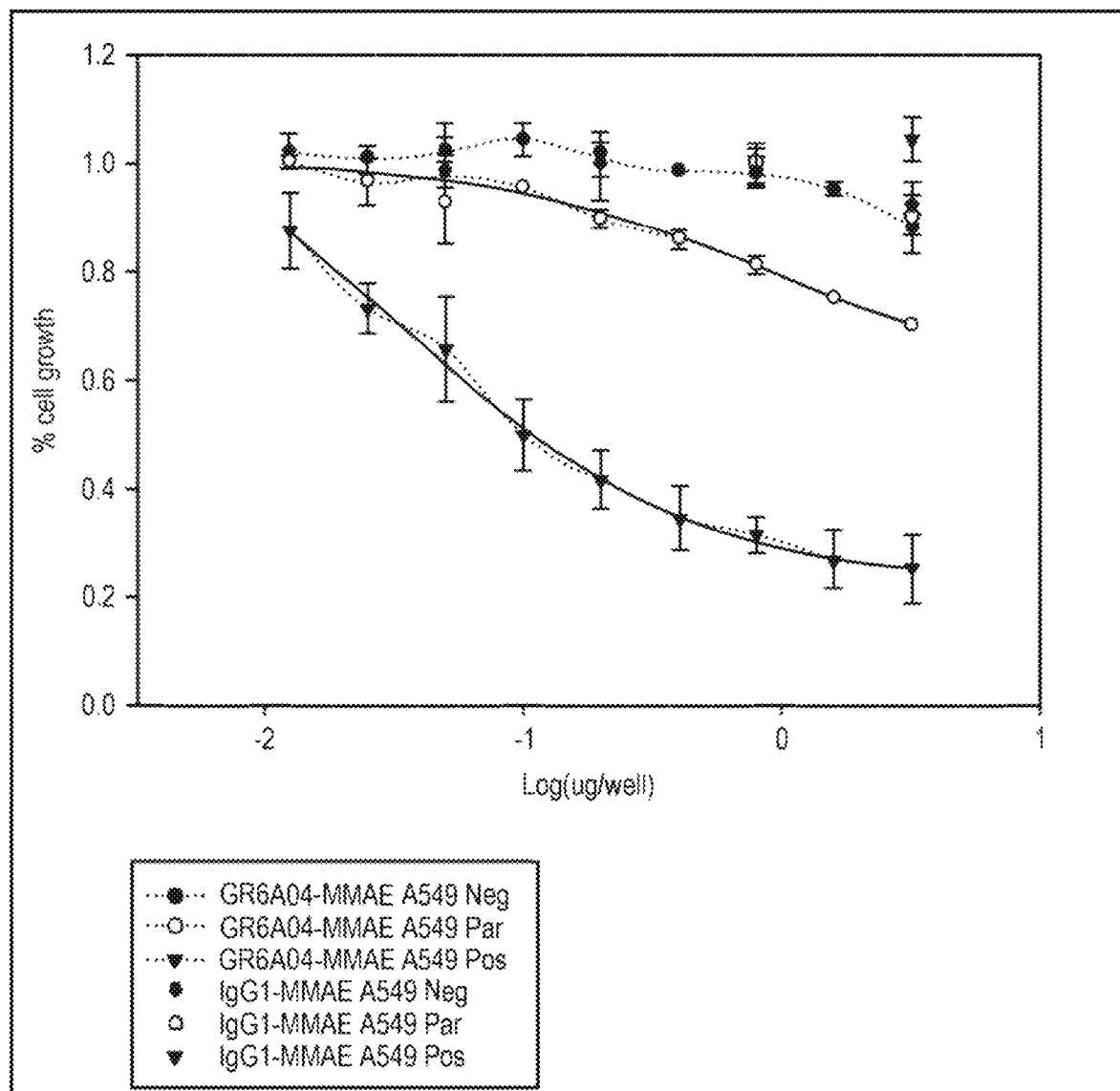

GR6A04 was subsequently directly conjugated to MMAE (FIG. 4C) for a more robust assay. A dose response curve was conducted on PC-9 and A549 binding cells, and H1299 non-binding cells (FIGS. 22A-B). EC50 was established to be 19.8 nM for PC-9 cells and 3.33 nM for A549A549-GR6A04+ cells. GR6A04-MMAE did not have an effect on cell growth for non-binding cells, H1299 and A549A549-GR6A04- populations, demonstrating specificity to GR6A04 binding cells only.

Figure 4D:
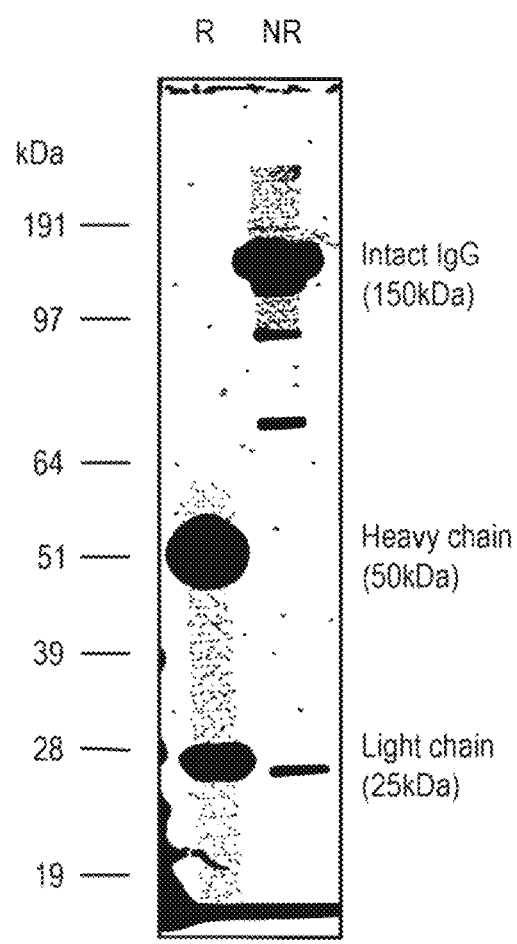
Figure 23:
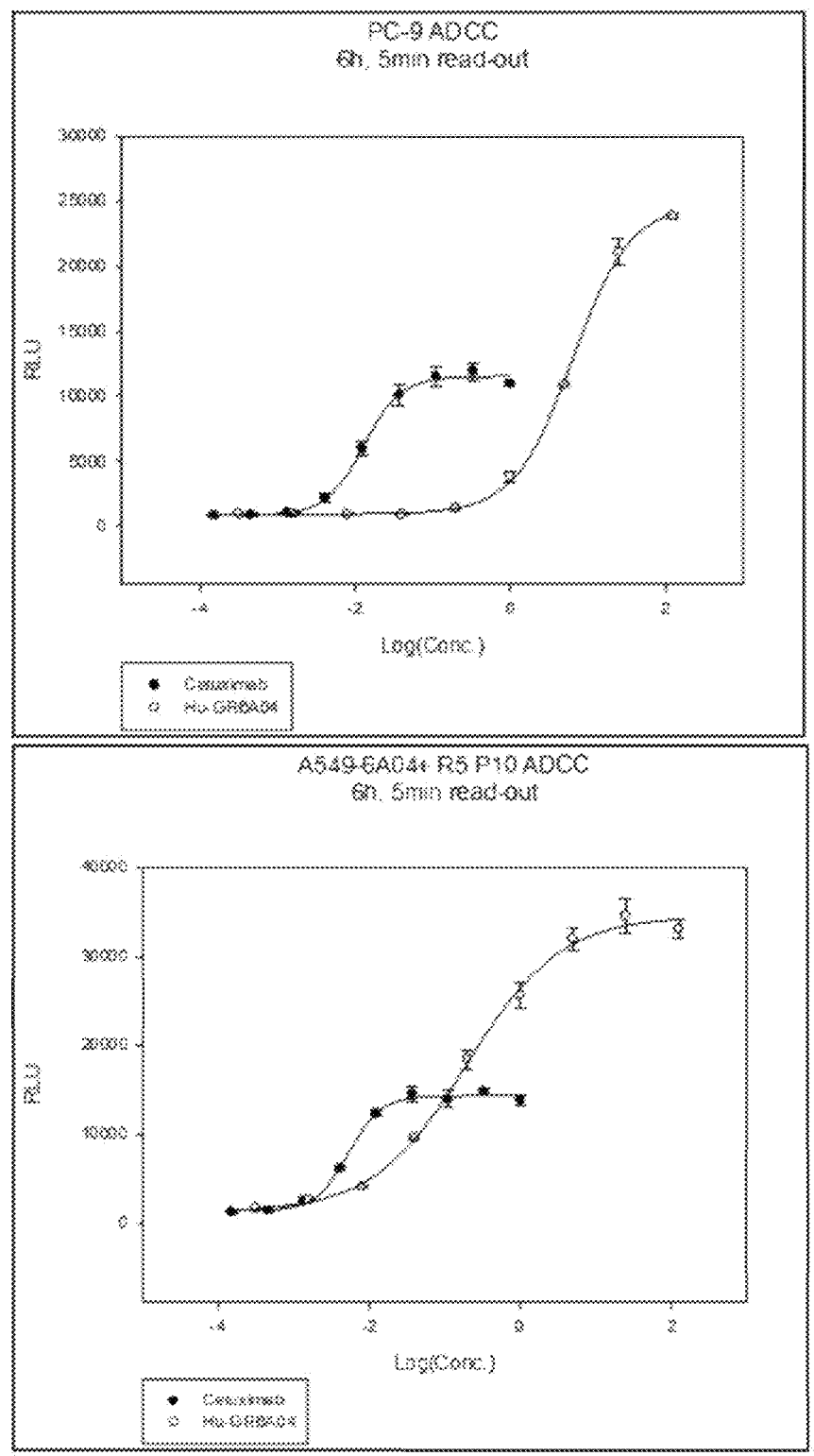
FIG. 23 shows antibody dependent cell cytotoxicity of GR 6A04. Promea ADCC kit was used with the Luciferase reporter for FcγR and Cetuximab as a positive ADCC control. EC50 for PC-9: 39.6 nM; EC50 for A549-GR6A04+: 1.33 nM.

GR6A04 was also developed as a chimeric mAb with a human IgG constant backbone (FIGS. 4D-E). Hu-GR6A04 was tested for antibody-dependent cell cytotoxicity (ADCC) using a Promega ADCC kit, which as a Luciferase reporter for FcγR binding (FIG. 23). A dose-response curve on PC-9 and A549-GR6A04+ was done, and the EC50 established to be 39.6 nM and 1.33 nM respectively.

Hence, GR6A04 has demonstrated in vitro functionality on two lung cancer cell lines, PC-9 (gefitinib sensitive) and A549 (gefitinib-resistant), as a naked human chimeric mAb with ADCC activity, and as an ADC conjugated with MMAE.

Figure 24:
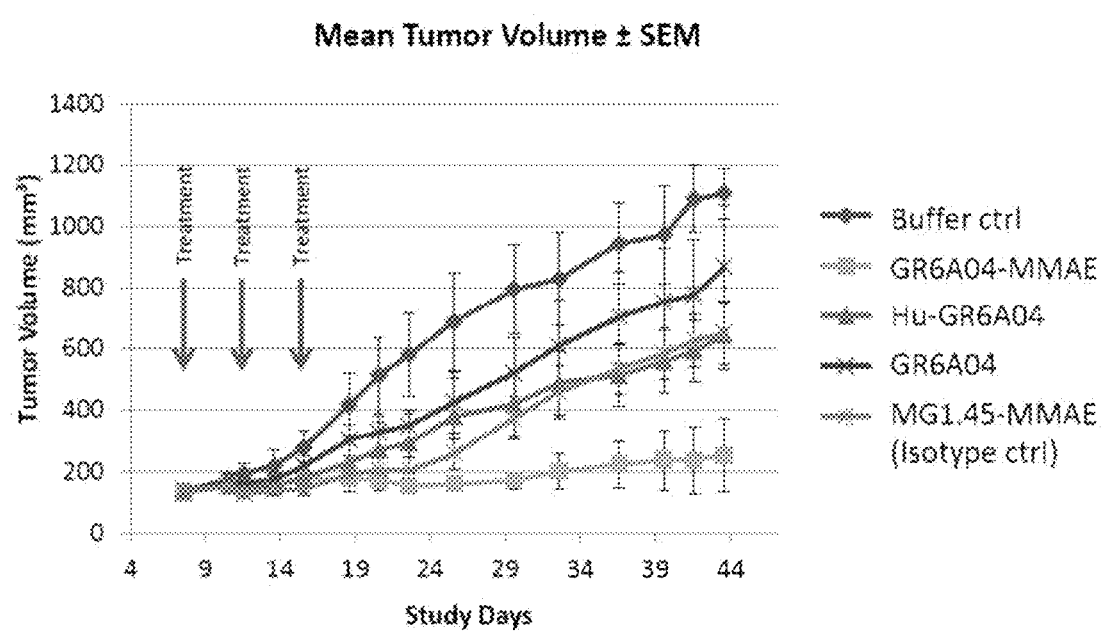
FIG. 24 shows GR 6A04 proof of concept as ADC in a xenograft model. Conditions used were GR6A04-MMAE; MG1.45-MMAE isotype Ctrl; Buffer Ctrl; GR6A04 (unconjugated); Hu-GR6A04 (unconjugated). Treatment regime was 10 mg/kg (~200 μg/mouse) and 3 doses, on D0, D4 and D8 (starting at tumor size>150 mm3). The results indicated that xenografts treated with GR6A04-MMAE showed little tumour growth which demonstrated excellent in vivo functionality as an ADC. Xenografts treated with unconjugated GR6A04 and Hu-GR6A04 showed slower growth compared to the buffer control, which indicated some in vivo tumour growth inhibition via ADCC mechanisms.

Finally, in vivo functionality was tested using A549-GR6A04+ cells in a subcutaneous xenograft model (FIG. 24). Treatment with GR6A04 and their derivatives was initiated when the tumour reaches 150 mm³, with I.V. mAb injection at 10 mg/kg, every 4 days for 3 doses. Both the naked mAbs, Gr6A04 and Hu-GR6A04 showed repression of tumour growth for the buffer control, attributed to ADCC mechanisms. Importantly, GR6A04-MMAE was extremely effective in controlling tumour size, with little tumour growth (<2-fold) throughout the 45 days of study. Hence, GR6A04 has demonstrated good in vivo functionality with a gefitinib-resistant A549 xenograft model, congruent with the in vitro results.

What is claimed is:

1. An antigen-binding protein, or an antigen-binding fragment thereof, comprising (i) a heavy chain variable domain comprising a VHCDR1 having the amino acid sequence GNTFTSYVMH (SEQ ID NO: 3); a VHCDR2 having the amino acid sequence YINPYNDGTKYNEKFKG (SEQ ID NO: 4); and a VHCDR3 having the amino acid sequence STARATPYFYAMDY (SEQ ID NO: 5); and (ii) a light chain variable domain comprising a VLCDR1 having the amino acid sequence KSSQSLLWSVNQNSYLS (SEQ ID NO: 6), a VLCDR2 having the amino acid sequence GASIRES (SEQ ID NO: 7), and a VLCDR3 having the amino acid sequence QHNHGSFLPYT (SEQ ID NO: 8), wherein the antigen-binding protein, or an antigen-binding fragment thereof, comprises a monomethyl auristatin E (MMAE) conjugated thereto.

2. The antigen-binding protein, or antigen-binding fragment thereof, as claimed in claim 1, wherein the heavy chain variable region comprises an amino acid sequence having about 90%, about 95%, about 96%, about 97%, about 98% or about 99% identity to the amino acid sequence SGPELVKPGASVKMSCKASGNTFTSYVMHWVKQKPGQGLEWIGYINPYNDG TKYNEKFKGKATLTSDKSS STAYMELS SLTSEDSAVYYCARSTARATPYFYAMDYWGQGTSVTVSS as set forth in SEQ ID NO: 1.

3. The antigen-binding protein, or antigen-binding fragment thereof, as claimed in claim 1, wherein the light chain variable region comprises an amino acid sequence having about 90%, about 95%, about 96%, about 97%, about 98% or about 99% identity to the amino acid sequence DILMTQSPSSLAVTAGEKVTMRCKS SQSLLWSVNQNSYLSWYQLKQGQPPKLLLYGASIRESWVPDRFTGSGSGTDFTLTIS NVHVEDLAVYYCQHNHGSFLPYTFGGGTKLEIK as set forth in SEQ ID NO:2.

4. The antigen-binding protein, or antigen-binding fragment thereof, as claimed in claim 1, wherein the antigen binding protein is selected from the group consisting of monoclonal, recombinant, polyclonal, chimeric, humanised, bispecific and heteroconjugate antibodies; a chimeric antigen receptor (CAR), a domain antibody, antigen binding fragments, immunologically effective fragments, single chain Fv, a single chain antibody, a univalent antibody lacking a hinge region, a minibody, diabodies, and tandem diabodies.

5. The antigen-binding protein, or antigen-binding fragment thereof as claimed in claim 1, wherein the antigen-binding protein, or an antigen-binding fragment is internalized into a cell upon binding to CEACAM6.

6. The antigen-binding protein, or antigen-binding fragment thereof as claimed in claim 1, wherein the antigen-binding protein, or an antigen-binding fragment is not internalized into a cell upon binding to CEACAM6.

7. A composition comprising a physiologically acceptable carrier and a therapeutically effective amount of an antigen-binding protein, or an antigen-binding fragment thereof, comprising (i) a heavy chain variable domain comprising a VHCDR1 having the amino acid sequence GNTFTSYVMH (SEQ ID NO: 3); a VHCDR2 having the amino acid sequence YINPYNDGTKYNEKFKG (SEQ ID NO: 4); and a VHCDR3 having the amino acid sequence STARATPYFYAMDY (SEQ ID NO: 5); and (ii) a light chain variable domain comprising a VLCDR1 having the amino acid sequence KSSQSLLWSVNQNSYLS (SEQ ID NO: 6), a VLCDR2 having the amino acid sequence GASIRES (SEQ ID NO: 7), and a VLCDR3 having the amino acid sequence QHNHGSFLPYT (SEQ ID NO: 8), wherein the antigen-binding protein, or an antigen-binding fragment thereof, comprises a monomethyl auristatin E (MMAE) conjugated thereto.

8. The composition as claimed in claim 7, comprising one or more further therapeutic compounds.

9. A method for treating cancer in a subject in need thereof comprising administering to the subject an antigen-binding protein or an antigen-binding fragment thereof, comprising (i) a heavy chain variable domain comprising a VHCDR1 having the amino acid sequence GNTFTSYVMH (SEQ ID NO: 3); a VHCDR2 having the amino acid sequence YINPYNDGTKYNEKFKG (SEQ ID NO: 4); and a VHCDR3 having the amino acid sequence STARATPYFYAMDY (SEQ ID NO: 5); and (ii) a light chain variable domain comprising a VLCDR1 having the amino acid sequence KSSQSLLWSVNQNSYLS (SEQ ID NO: 6), a VLCDR2 having the amino acid sequence GASIRES (SEQ ID NO: 7), and a VLCDR3 having the amino acid sequence QHNHGSFLPYT (SEQ ID NO: 8), wherein the antigen-binding protein, or an antigen-binding fragment thereof, comprises a monomethyl auristatin E (MMAE) conjugated thereto.

10. The method of claim 9, wherein the cancer is selected from the group consisting of gefitinib resistant lung cancer, non-small cell lung cancer, breast cancer, stomach cancer, small intestine cancer, esophageal cancer, and colorectal cancer.

11. The method of claim 9, further comprising administering one or more further active pharmaceutical ingredients or chemotherapy.

12. The method of claim 11, wherein the one or more further active pharmaceutical ingredients or chemotherapy is administered separately, simultaneously, or sequentially with said antigen-binding protein or antigen-binding fragment thereof.

\* \* \* \* \*

```
                             SEQUENCE LISTING

Sequence total quantity: 8
SEQ ID NO: 1            moltype = AA  length = 117
FEATURE                 Location/Qualifiers
REGION                  1..117
                        note = Isolated antibody fragment
source                  1..117
                        mol_type = protein
                        organism = synthetic construct
SEQUENCE: 1
SGPELVKPGA SVKMSCKASG NTFTSYVMHW VKQKPGQGLE WIGYINPYND GTKYNEKFKG  60
KATLTSDKSS STAYMELSSL TSEDSAVYYC ARSTARATPY FYAMDYWGQG TSVTVSS    117

SEQ ID NO: 2            moltype = AA  length = 115
FEATURE                 Location/Qualifiers
REGION                  1..115
                        note = Isolated antibody fragment
source                  1..115
                        mol_type = protein
                        organism = synthetic construct
SEQUENCE: 2
DILMTQSPSS LAVTAGEKVT MRCKSSQSLL WSVNQNSYLS WYQLKQGQPP KLLLYGASIR  60
ESWVPDRFTG SGSGTDFTLT ISNVHVEDLA VYYCQHNHGS FLPYTFGGGT KLEIK      115

SEQ ID NO: 3            moltype = AA  length = 10
FEATURE                 Location/Qualifiers
REGION                  1..10
                        note = Isolated antibody fragment
source                  1..10
                        mol_type = protein
                        organism = synthetic construct
SEQUENCE: 3
GNTFTSYVMH                                                         10

SEQ ID NO: 4            moltype = AA  length = 17
FEATURE                 Location/Qualifiers
REGION                  1..17
                        note = Isolated antibody fragment
source                  1..17
                        mol_type = protein
                        organism = synthetic construct
SEQUENCE: 4
YINPYNDGTK YNEKFKG                                                 17

SEQ ID NO: 5            moltype = AA  length = 14
FEATURE                 Location/Qualifiers
REGION                  1..14
                        note = Isolated antibody fragment
source                  1..14
                        mol_type = protein
                        organism = synthetic construct
SEQUENCE: 5
STARATPYFY AMDY                                                    14

SEQ ID NO: 6            moltype = AA  length = 16
FEATURE                 Location/Qualifiers
REGION                  1..16
                        note = Isolated antibody fragment
source                  1..16
                        mol_type = protein
                        organism = synthetic construct
SEQUENCE: 6
SSQSLLWSVN QNSYLS                                                  16

SEQ ID NO: 7            moltype = AA  length = 7
FEATURE                 Location/Qualifiers
REGION                  1..7
                        note = Isolated antibody fragment
source                  1..7
                        mol_type = protein
                        organism = synthetic construct
SEQUENCE: 7
```

```
GASIRES                                                      7
SEQ ID NO: 8           moltype = AA  length = 11
FEATURE                Location/Qualifiers
REGION                 1..11
                       note = Isolated antibody fragment
source                 1..11
                       mol_type = protein
                       organism = synthetic construct
SEQUENCE: 8
QHNHGSFLPY T                                                 11
```